US007639855B2

(12) United States Patent
Matsumoto

(10) Patent No.: US 7,639,855 B2
(45) Date of Patent: Dec. 29, 2009

(54) MEDICAL IMAGE PROCESSING APPARATUS, AND MEDICAL IMAGE PROCESSING METHOD

(75) Inventor: Kazuhiko Matsumoto, Tokyo (JP)

(73) Assignee: Ziosoft, Inc., Tokyo (JP)

( * ) Notice: Subject to any disclaimer, the term of this patent is extended or adjusted under 35 U.S.C. 154(b) by 813 days.

(21) Appl. No.: 10/816,978

(22) Filed: Apr. 2, 2004

(65) Prior Publication Data
US 2004/0220466 A1 Nov. 4, 2004

(30) Foreign Application Priority Data

| Apr. 2, 2003 | (JP) | ............................. 2003-099649 |
| Jun. 5, 2003 | (JP) | ............................. 2003-161241 |
| Jul. 4, 2003 | (JP) | ............................. 2003-270923 |

(51) Int. Cl.
G06K 9/00 (2006.01)
(52) U.S. Cl. ...................... 382/131; 600/407
(58) Field of Classification Search ................. 382/131; 600/407
See application file for complete search history.

(56) References Cited

U.S. PATENT DOCUMENTS

| 5,891,030 | A | * | 4/1999 | Johnson et al. ............. 600/407 |
| 6,331,116 | B1 | * | 12/2001 | Kaufman et al. ............. 434/262 |
| 6,424,732 | B1 | | 7/2002 | Shiffman et al. |
| 6,501,848 | B1 | | 12/2002 | Carroll et al. |
| 6,628,743 | B1 | | 9/2003 | Drummond et al. |
| 6,643,533 | B2 | | 11/2003 | Knoplioch et al. |
| 6,668,083 | B1 | | 12/2003 | Verdonck et al. |
| 6,678,399 | B2 | | 1/2004 | Doi et al. |
| 6,728,566 | B1 | * | 4/2004 | Subramanyan et al. ...... 600/407 |
| 6,829,379 | B1 | * | 12/2004 | Knoplioch et al. .......... 382/131 |

(Continued)

FOREIGN PATENT DOCUMENTS

JP 06-309426 11/1994

(Continued)

OTHER PUBLICATIONS

Stanislav L. Stoev, et al., Extracting Regions of Interest Applying a Local Watershed Transformation; University of Tubingen; Oct. 8-13, 2000.

(Continued)

Primary Examiner—Brian P Werner
Assistant Examiner—Katrina Fujita
(74) Attorney, Agent, or Firm—Howard & Howard Attorneys PLLC

(57) ABSTRACT

An image processing apparatus acquires three-dimensional volume data from a modality, and a start point, end point, etc. of an extraction target vessel. The image processing apparatus specifies cross sectional regions of the vessel sequentially from the designated start point. The image processing apparatus sequentially obtains the area of images appearing in each specified cross sectional region in accordance with changes in threshold. The image processing apparatus clarifies the cross section of the vessel in each region based on rate of change in the obtained area. The image processing apparatus obtains a center position of the clarified cross section of the vessel, and obtains a three-dimensional path representing a center line of the vessel in its longitudinal direction. The image processing apparatus generates plural kinds of images representing the vessel based on the obtained three-dimensional path, and displays them together on a display device.

36 Claims, 44 Drawing Sheets

U.S. PATENT DOCUMENTS 6,842,638 B1 * 1/2005 Suri et al. .................. 600/425

FOREIGN PATENT DOCUMENTS

| JP | 07-129751 | 5/1995 |
| JP | 08-089501 | 4/1996 |
| JP | 09-327455 | 12/1997 |
| JP | 2001-079097 | 3/2001 |
| JP | 2001-145614 | 5/2001 |
| JP | 2002-282235 | 10/2002 |
| JP | 2003-010172 | 1/2003 |
| WO | WO 01/37219 A1 | 5/2001 |
| WO | WO 02/084594 A2 | 10/2002 |
| WO | WO 03/046835 A1 | 6/2003 |

OTHER PUBLICATIONS

Office Action dated Oct. 4, 2005 for Japanese Patent Application No. 2003-161241.

Office Action dated Nov. 24, 2005 for Japanese Patent Application No. 2003-270923.

* cited by examiner

SLICE IMAGE

MPR

CPR

MARCHING (ADVANCING, PROGRESSING) DIRECTION SETTLING FORMULAE

---

$n1$ : UNIT VECTOR PARALLEL TO TEMPORARY MARCHING DIRECTION DirA
$n2$ : UNIT VECTOR PERPENDICULAR TO REGION PR1
$n3$ : UNIT VECTOR PERPENDICULAR TO REGION PR2
$v2$ : POSITION VECTOR OF CENTER POSITION ON REGION PR1
$v3$ : POSITION VECTOR OF CENTER POSITION ON REGION PR2

---

IN CASE OF $v2 \cdot n1 > v3 \cdot n1$

VECTOR TO NEXT POSITION = $v2' \cdot n1 * n1 + v2' \cdot n3 * n3 + v3 \cdot n2 * n2$ WHERE $v2' = v3 \cdot n1 / v2 \cdot n1 * v2$ IN CASE OF $v2 \cdot n1 \leq v3 \cdot n1$ VECTOR TO NEXT POSITION = $v2 \cdot n1 * n1 + v2 \cdot n3 * n3 + v3' \cdot n2 * n2$ WHERE $v3' = v2 \cdot n1 / v3 \cdot n1 * v3$ $$\left( \begin{array}{l} \cdot \text{ REPRESENTS INNER PRODUCT OF VECTORS} \\ * \text{ REPRESENTS OUTER PRODUCT OF VECTORS} \end{array} \right)$$

FIG.13

THRESHOLD ATTRIBUTE TABLE

| THRESHOLD | WITHIN REGION ? | AREA VALUE |
|---|---|---|
| th_min | NO | 1000 |
| th_min+1 | NO | 900 |
| th_min+2 | NO | 800 |
| th_min+3 | NO | 700 |
| ⋮ | ⋮ | ⋮ |
| th_max-3 | YES | 30 |
| th_max-2 | YES | 20 |
| th_max-1 | YES | 10 |
| th_max | YES | 0 |

FIG.20

IN CASE OF
THRESHOLD th_a

IN CASE OF
THRESHOLD th_b

IN CASE OF
THRESHOLD th_b+1

MEDICAL IMAGE PROCESSING APPARATUS, AND MEDICAL IMAGE PROCESSING METHOD

This application claims priority to Japanese Patent Application No. 2003-99649 filed on Apr. 2, 2003, Japanese Patent Application No. 2003-161241 filed on Jun. 5, 2003, and Japanese Patent Application No. 2003-270923 filed on Jul. 4, 2003 and incorporated herein by reference in its entirety.

BACKGROUND OF THE INVENTION

1. Field of the Invention

The present invention relates to a medial image processing apparatus and a medical image processing method for generating a three-dimensional medical image used in image diagnosis, etc. and particularly relates to a medical image processing apparatus, and a medical image processing method suitable for displaying a tubular tissue such as a vessel.

2. Description of the Related Art

Conventionally, there has been conducted image diagnosis for diagnosing diseases, etc. by acquiring a tomographic (slice) image of an organ, etc. of a human body using a modality (image acquiring apparatus) such as a CT scanner, an MRI apparatus, etc. Further, a method of conducting diagnosis by generating a three-dimensional image of a predetermined organ, etc. based on an acquired tomographic image has been established, contributing to a precise and accurate diagnosis. Especially, diagnosis by a three-dimensional image of a coronary vessel around a heart is helpful for an early detection of a heart disease.

In such three-dimensional image diagnosis, it is often the case that an image of an observation target part is extracted from an original three-dimensional image and then diagnosed by an observation. However, in general, it was difficult to extract an image of an elongated tubular tissue such as a vessel (particularly, a coronary vessel around a heart), in the past.

To solve such a problem, a method for an extraction of an image of a vessel tissue is disclosed in the Unexamined Japanese Patent Application KOKAI Publication No. 2002-282235 (pp. 4-5). According to this document, a "binary mask" which separates picture element values indicating a concerned area (i.e. a target vessel tissue) from picture element values indicating areas other than the concerned area is generated. By using this "binary mask", the vessel tissue is distinguished from other tissues. The picture element value indicates the gradation of a picture element. Further, picture elements include two-dimensional picture elements (pixels) and three-dimensional picture elements (voxels). Hereinafter, these will be denoted by "picture element".

In a method using a binary mask described above, once a picture element value for indicating a target tissue is set, it is determined whether a given part belongs to the target tissue or not based on whether each value of the picture element in the area subjected to the determination is the value indicating the target tissue. In this case, if only the target vessel for the extraction exists in the area subjected to the determination, the image of the target vessel can be extracted without any trouble. However, in general, other tissues (a vessel, an organ, etc.) exist closely to the target vessel. In particular, in a case where the target is a coronary vessel around a heart, the heart and many other vessels exist near the coronary vessel. Since the compositional elements of those close organs are almost the same as those of the target vessel, the picture element values indicating the close organs are similar to the picture element values indicating the target vessel. Because of this, the target vessel can not be extracted accurately by using a method disclosed in the Unexamined Japanese Patent Application KOKAI Publication No. H8-89501 (p. 6), for the target vessel can not be distinguished from the other tissues.

In a case where a coronary vessel extending from a heart is imaged (visualized) based on CT values obtained by an image acquiring apparatus such as a CT scanner, the generated image is normally reduced in brightness gradually as the coronary vessel extends away from its originating position. That is, it can be said that approximation is established such that picture element values change generally linearly in accordance with the distances from the originating position of the coronary vessel. By utilizing this characteristic, U.S. Pat. No. 6,424,732 discloses a method for extracting a target vessel by using a "multi-value mask" which allocates picture element values to the vessel by changing the values linearly from the originating position of the vessel to the extraction end position. However, in a case where a heart or other vessels exist closely to the target vessel or in a case where the target vessel has an abnormal part, the picture element values indicating the target vessel do not change simply linearly. Consequently, if an image is generated by changing picture element values simply linearly, the resulting image might be such that the target vessel and its close organ are combined or the target vessel is discontinuous. Therefore, it is difficult to obtain an image that can contribute to an accurate diagnosis.

A patent document 2 discloses a method of detecting a vessel part by detecting the average density around the attention point. However, in a case where a heart or other vessels exist closely to the target vessel, an effective density value can not be obtained. Therefore, this method can not extract the vessel part accurately, either.

SUMMARY OF THE INVENTION

The present invention was made in view of the above circumstance, and an object of the present invention is to provide a medical image processing apparatus, and a medical image processing method capable of accurately extracting a tubular tissue such as a vessel.

To achieve the above object, a medical image processing apparatus according to a first aspect of the present invention is a medical image processing apparatus for generating a medical image using three-dimensional volume data representing an internal portion of a biological body, and comprises:

a volume data obtaining unit which obtains predetermined three-dimensional volume data including a tubular tissue;

a region specifying unit which specifies a region including a position on the tubular tissue in the three-dimensional volume data, at each of a plurality of such positions;

an extraction unit which extracts information on the tubular tissue in each of the specified regions; and a medical image generating unit which generates a medical image representing the tubular tissue, based on the information extracted by said extraction unit.

It is preferred that extraction unit includes:

a center specifying unit which specifies a center position of a cross section of the tubular tissue in each of the plurality of regions specified by said region specifying unit, based on the three-dimensional volume data obtained by the volume data obtaining unit; and a center line specifying unit which specifies a center line of the tubular tissue in a longitudinal direction of the tubular tissue, based on the plurality of center positions specified by said center specifying unit.

It is preferred that said region specifying unit sequentially specifies regions along the tubular tissue; and said center specifying unit specifies a center of a cross section of the tubular tissue in each of the regions sequentially specified by said region specifying unit.

It is preferred that said region specifying unit specifies a planar region which orthogonally intersects with the longitudinal direction of the tubular tissue; and said center specifying unit specifies a center position of a cross section of the tubular tissue in the planar region specified by said region specifying unit.

It is preferred that extraction unit includes:

a unit which obtains a median point represented by the three-dimensional volume data, of the tubular tissue in each of the plurality of regions specified by said region specifying unit;

a cross sectional image generation unit which generates a cross sectional image representing a cross section of the tubular tissue at a position of the median point obtained by said unit for obtaining a median point; and a center specifying unit which specifies a center position of the cross section in the three-dimensional volume data, based on the generated cross sectional image.

It is preferred that further comprising a designation reception unit which receives designation for two arbitrary points on the tubular tissue represented by the three-dimensional volume data, wherein:

said region specifying unit sequentially specifies planar regions which orthogonally intersect with the longitudinal direction of the tubular tissue, at a plurality of positions between the two points along the tubular tissue; and said center specifying unit specifies a center of a cross section of the tubular tissue in each of the plurality of planar regions specified by said region specifying unit.

It is preferred that said designation reception unit receives designation for a planar region which orthogonally intersects with the longitudinal direction of the tubular tissue, at one of the two designated points;

said region specifying unit sequentially specifies points which are apart from one another by a predetermined distance in a direction heading from the one point to the other point of the two points along the tubular tissue, and sequentially specifies planar regions orthogonally intersecting with the longitudinal direction of the tubular tissue at each of the specified points;

said center specifying unit specifies a center position of a cross section of the tubular tissue in each of the plurality of planar regions specified by said region specifying unit; and said center line specifying unit specifies a center line of the tubular tissue in the longitudinal direction of the tubular tissue, based on the plurality of center positions specified by said center specifying unit.

It is preferred that the three-dimensional volume data includes three-dimensional coordinate information and characteristic information representing a characteristic unique to a substance at each position represented by the three-dimensional coordinate information; and said cross sectional image generation unit generates an image based on information representing a three-dimensional coordinate position having the characteristic information which satisfies a predetermined condition in the three-dimensional volume data, and clarifies the cross section of the tubular tissue in the image.

It is preferred that wherein said imaging unit comprises:

a condition changing unit which changes the predetermined condition;

an image attribute detecting unit which detects an image attribute which changes in accordance with changes in the predetermined condition; and a clarification determining unit which determines whether or not the cross section of the tubular tissue is clarified in an image, based on detected changes in the image attribute.

It is preferred that the image attribute represents an area of an image (image area);

said image attribute detecting unit detects an image area which changes in accordance with changes in the predetermined condition, and detects a change in the image area corresponding to the changes in the predetermined condition; and said clarification determining unit determines whether or not the cross section of the tubular tissue is clarified, based on the detected change in the image area.

It is preferred that wherein said clarification determining unit determines that the cross section of the tubular tissue is clarified in the image, when an image appearing in a center of the region including the cross section become fit inside the region, and the change in the image area becomes the largest.

It is preferred that wherein said region specifying unit determines a position of a three-dimensional region to be specified next, based on the three-dimensional volume data which is specified by said center line specifying unit and which represents the center line of the tubular tissue.

It is preferred that said center line specifying unit specifies the center line of the tubular tissue as three-dimensional path data; and said medical image processing apparatus further comprises an image generating unit which generates an image representing the tubular tissue based on the three-dimensional path data specified by said center line specifying unit.

It is preferred that wherein said image generating unit comprises:

an image calculating unit which generates plural kinds of images each representing the tubular tissue, and calculates relative positional relationships between the images; and a display control unit which displays the generated plural kinds of images all at once on a predetermined display device, and displays positional relationships on the displayed images by associating the relations based on the relative positional relationships between the images calculated by said image calculating unit.

It is preferred that said region specifying unit specifies a predetermined three-dimensional region whose center is an arbitrary point on the predetermined tubular tissue represented by the three-dimensional volume data;

said medical image processing apparatus further comprises an image clarifying unit which clarifies a three-dimensional image representing only the predetermined tubular tissue in the specified three-dimensional region, by changing predetermined characteristic information included in the three-dimensional volume data which constitutes a three-dimensional image obtained by data-conversion of said imaging unit; and said medical image generating unit generates a predetermined medical image representing the predetermined tubular tissue, by using the three-dimensional image clarified by said image clarifying unit.

It is preferred that said image clarifying unit comprises a closed region detecting unit which detects a closed region which constitutes the three-dimensional image obtained by data-conversion of said imaging unit and which includes a center of the three-dimensional region, and a clarification determining unit which determines based on the closed region detected by said closed region detecting unit and the three-dimensional region whether or not the closed region represents only the predetermined tubular tissue; and the closed region which is determined by said clarification determining unit as representing only the predetermined tubular tissue is regarded as the clarified three-dimensional image.

It is preferred that said closed region detecting unit detects a change in the closed region corresponding to changes in the characteristic information; and said clarification determining unit determines whether or not the closed region represents only the predetermined tubular tissue, based on changes in the closed region.

It is preferred that said region specifying unit specifies a plurality of three-dimensional regions by setting a center of a three-dimensional region to be specified next based on the arbitrary point and/or the clarified three-dimensional image; and said medical image generating unit generates the predetermined medical image representing the predetermined tubular tissue, by using three-dimensional images clarified in the plurality of three-dimensional regions.

To achieve the above object, a medical image processing method according to a second aspect of the present invention is a medical image processing method for generating an image representing a tubular tissue in a living body by using a computer, said method comprising:

a step of obtaining predetermined three-dimensional volume data including a tubular tissue;

a step of specifying a region including a position on the tubular tissue in the three-dimensional volume data, at a plurality of such positions;

a step of extracting information on the tubular tissue in each of the plurality of specified regions; and a step of generating a medical image representing the tubular tissue, based on the extracted information.

It is preferred that said step of extracting information on the tubular tissue includes:

a step of specifying a center position of a cross section of the tubular tissue in each of the plurality of specified regions; and a step of specifying a center line of the tubular tissue in a longitudinal direction of the tubular tissue, based on the plurality of specified center positions.

It is preferred that in said step of specifying a region, regions are sequentially specified along the tubular tissue; and In said step of specifying a center position, a center position of a cross section of the tubular tissue in each of the regions sequentially specified is specified.

It is preferred that in said step of specifying a region, a planar region which orthogonally intersects with the longitudinal direction of the tubular tissue is specified; and In said step of specifying a center position, a center position of a cross section of the tubular tissue in the specified planar region is specified.

It is preferred that step of extracting information includes:

a step of obtaining a median point of the tubular tissue represented by the three-dimensional volume data in each of the plurality of specified regions;

a step of generating a cross sectional image representing a cross section of the tubular tissue at a position of the median point obtained in said step of obtaining a median point; and a step of specifying a center position of the cross section in the three-dimensional volume data, based on the generated cross sectional image.

It is preferred that further comprising a step of receiving designation for two arbitrary points on the tubular tissue represented by the three-dimensional volume data, wherein:

in said step of specifying a region, planar regions orthogonally intersecting with the longitudinal direction of the tubular tissue are sequentially specified at a plurality of positions between the two points along the tubular tissue; and in said step of specifying a center position, a center position of a cross section of the tubular tissue in each of the plurality of specified planar regions is specified.

It is preferred that in said step of receiving designation, designation for a planar region orthogonally intersecting with the longitudinal direction of the tubular tissue at one of the two designated points is received;

in said step of specifying a region, points apart from one another by a predetermined distance are sequentially specified along the tubular tissue in a direction heading from the one point to the other point of the two points, and planar regions orthogonally intersecting with the longitudinal direction of the tubular tissue at the specified points are sequentially specified;

in said step of specifying a center position, a center position of a cross section of the tubular tissue in each of the specified planar regions is specified; and in said step of specifying a center line, a center line of the tubular tissue in the longitudinal direction of the tubular tissue is specified based on the specified center positions.

It is preferred that the three-dimensional volume data includes three-dimensional coordinate information and characteristic information representing a characteristic unique to a substance at each position represented by the three-dimensional coordinate information; and in said step of generating a cross sectional image, an image is generated based on information representing a three-dimensional coordinate position having the characteristic information satisfying a predetermined condition in the three-dimensional volume data, and the cross section of the tubular tissue is clarified in the image.

It is preferred that said step of generating a cross sectional image includes:

a step of changing the predetermined condition;

a step of detecting an image attribute which changes in accordance with changes in the predetermined condition; and a step of determining whether or not the cross section of the tubular issue is clarified in an image, based on detected changes in the image attribute.

It is preferred that the image attribute represents an area of an image (image area);

in said step of detecting an image area which changes in accordance with changes in the predetermined condition, and detects a change in the image area corresponding to the changes in the predetermined condition; and in said step of determining whether or not the cross section of the tubular tissue is clarified, based on the detected change in the image area.

It is preferred that wherein said step of determining that the cross section of the tubular tissue is clarified in the image, when an image appearing in a center of the region including the cross section become fit inside the region, and the change in the image area becomes the largest.

It is preferred that said step of determining a position of a three-dimensional region to be specified next, based on the three-dimensional volume data which is specified in said step of specifying the center line of the tubular tissue.

It is preferred that said step of specifying the center line of the tubular tissue as three-dimensional path data; and said step of generating an image representing the tubular tissue based on the three-dimensional path data specified in said step of specifying the center line of the tubular tissue.

It is preferred that said step of generating an image comprises:

a step of generating plural kinds of images each representing the tubular tissue, and calculates relative positional relationships between the images; and a step of displaying the generated plural kinds of images all at once on a predetermined display device, and displays positional relationships on the displayed images by associating the relations based on the relative positional relationships between the images calculated in said step of generating plural kinds of images.

It is preferred that said step of specifying a predetermined three-dimensional region whose center is an arbitrary point on the predetermined tubular tissue represented by the three-dimensional volume data;

said step of clarifying a three-dimensional image representing only the predetermined tubular tissue in the specified three-dimensional region, by changing predetermined characteristic information included in the three-dimensional volume data which constitutes a three-dimensional image obtained by data-conversion; and said step of generating a predetermined medical image representing the predetermined tubular tissue, by using the three-dimensional image clarified in said step of clarifying an image.

It is preferred that said step of clarifying an image a step of detecting a closed region which constitutes the three-dimensional image obtained by data-conversion and which includes a center of the three-dimensional region, and a step of determining based on the detected closed region and the three-dimensional region whether or not the closed region represents only the predetermined tubular tissue; and the closed region which is determined as representing only the predetermined tubular tissue is regarded as the clarified three-dimensional image.

It is preferred that said step of detecting a change in the closed region corresponding to changes in the characteristic information; and said step of determining whether or not the closed region represents only the predetermined tubular tissue, based on changes in the closed region.

It is preferred that said step of specifying a plurality of three-dimensional regions by setting a center of a three-dimensional region to be specified next based on the arbitrary point and/or the clarified three-dimensional image; and said step of generating the predetermined medical image representing the predetermined tubular tissue, by using three-dimensional images clarified in the plurality of three-dimensional regions.

BRIEF DESCRIPTION OF THE DRAWINGS

These objects and other objects and advantages of the present invention will become more apparent upon reading of the following detailed description and the accompanying drawings in which:

FIG. 4 are diagrams for explaining method for specifying an arbitrary region in three-dimensional volume data, where

FIG. 12 are diagrams showing examples of longitudinal direction images obtained in the marching (advancing, progressing) direction settling process shown in FIG. 10, where

FIG. 13 is a diagram showing examples of formulae used for calculating a vector in the marching (advancing, progressing) direction settling process shown in FIG. 10;

FIG. 16 are diagrams exemplarily showing examples of converted data obtained by data-converting the orthogonal cross sectional regions shown in FIG. 15, where

FIG. 18 are diagrams for explaining the vessel center detecting process shown in FIG. 17, where

FIG. 19 are diagrams for explaining the vessel center detecting process shown in FIG. 17, where

FIG. 20 is a diagram showing an example of a "threshold attribute table" generated in the vessel center detecting process shown in FIG. 17;

FIG. 23 are diagrams for explaining change of an image in the cross section clarifying process shown in FIG. 21, where

FIG. 24 are diagrams for explaining change of an image in the cross section clarifying process shown in FIG. 21, where

FIG. 25 are diagrams for explaining change of an image in the cross section clarifying process shown in FIG. 21, where

FIG. 26 are diagrams for explaining change of an image in the cross section clarifying process shown in FIG. 21, where

FIG. 32 are diagrams for explaining a process included in the "vessel image extracting process" shown in FIG. 30, where

FIG. 35 are diagrams for explaining an example of a case where a target vessel and a heart are close to each other, where

FIG. 38 are diagrams for explaining changes in the volume of a continuous region appearing in the graph shown in FIG. 37, where

FIG. 39 are diagrams for explaining a "next center position determining process" in the "vessel image extracting process" shown in FIG. 30, where

FIG. 40 are diagrams for explaining a case where a "three-dimensional region" is used for specifying a cross sectional region according to an embodiment of the present invention, where

FIG. 42 are diagrams for explaining another method of specifying a cubic region shown in FIG. 40, where

FIG. 43 are diagrams showing other examples of the three-dimensional region shown in FIG. 40, where FIG. 44 are diagrams showing other examples of the three-dimensional region shown in FIG. 40, where

DETAILED DESCRIPTION OF THE PREFERRED EMBODIMENT

An embodiment of the present invention will now be explained with reference to the drawings. In the embodiment to be described below, explanation will be made by taking a case where the present invention is applied to three-dimensional image diagnosis in a predetermined medical facility (hereinafter referred to as "medical facility H") as an example.

Figure 1:
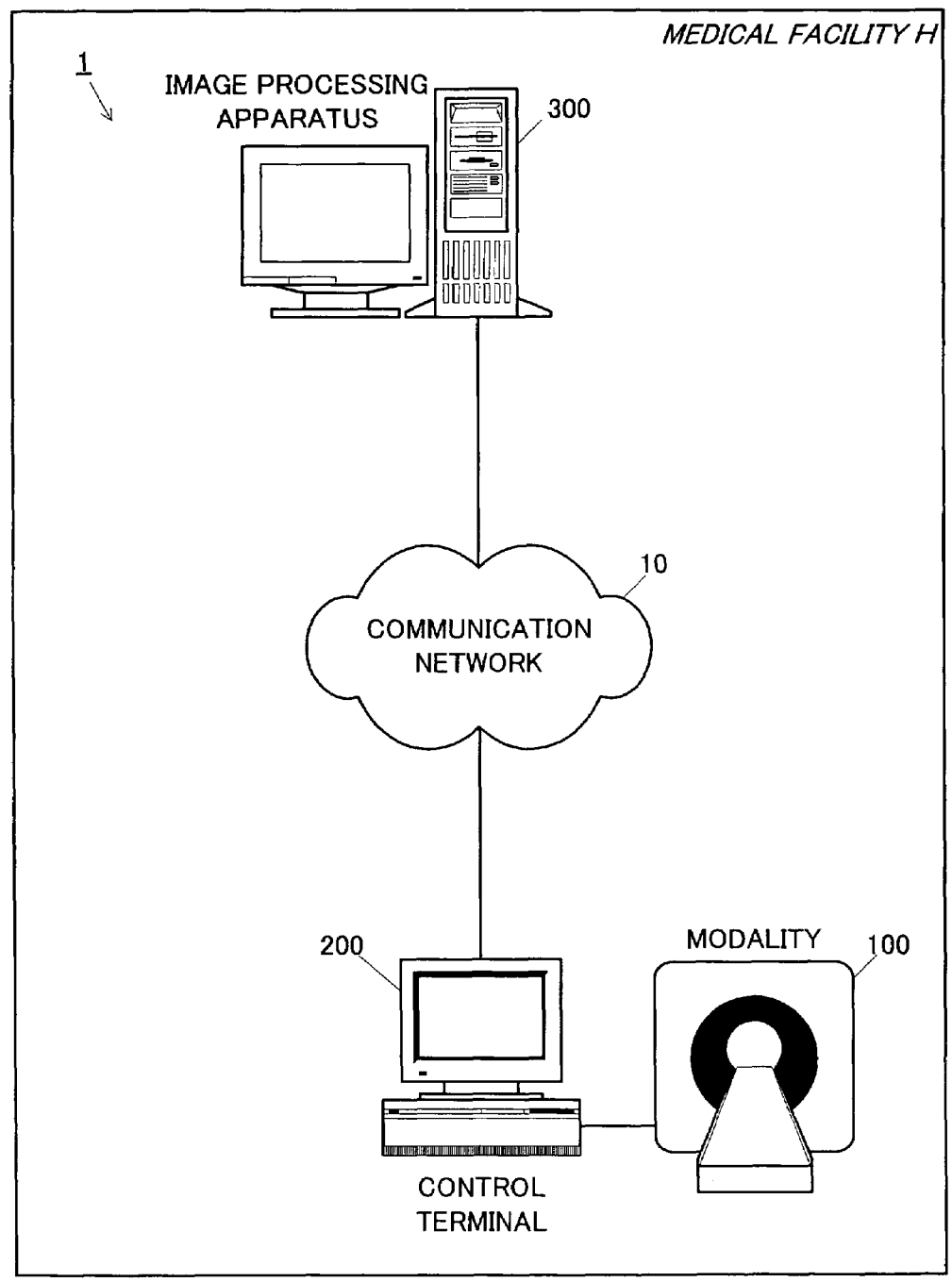
FIG. 1 is a diagram exemplarily showing a structure of an "image diagnosis system" according to an embodiment of the present invention.

FIG. 1 is a diagram showing a structure of an image diagnosis system according to an embodiment of the present invention. As shown in FIG. 1, the image diagnosis system 1 according to the present embodiment comprises a communication network 10, a modality 100, a control terminal 200, and an image processing apparatus 300.

The communication network 10 is a communication network that mutually connects the control terminal 200 and the image processing apparatus 300 in the medical facility H, and intermediates information transmission between them. The communication network 10 intermediates information transmission which is based on a predetermined communication protocol, such as DICOM (Digital Imaging and Communications in Medicine).

Next, the modality 100 will be explained. The modality 100 is an image acquiring apparatus for acquiring an image of the inside of a human body, and may be, for example, a CT scanner (Computerized Tomography apparatus), a helical CT, an MRI (Magnetic Resonance Imaging apparatus), a PET (Positron Emission Tomography apparatus), etc. In the present embodiment, a CT scanner for acquiring a tomographic image of the inside of a human body using X-rays is employed as the modality 100.

According to the present embodiment, the modality 100 (CT scanner) is controlled by the control terminal 200 to be described later, and acquires a tomographic (slice) image of the inside (inside of a biological body) of a patient or a medical examinee (hereinafter referred to as "medical examinee, etc."). Since in the present embodiment, a CT scanner is employed as the modality 100, information representing a tomographic image includes CT values which are X-ray absorption factors. The modality 100 and the control terminal 200 are connected to each other based on a predetermined medical image communication standard such as DICOM (Digital Imaging and Communications in Medicine).

Next, the control terminal 200 will be explained. The control terminal 200 is constituted by a predetermined information processing apparatus such as a workstation. The control terminal 200 controls the operation of the modality 100 connected thereto, and receives acquired image data (original data) obtained by image acquiring by the modality 100. The structure of the control terminal 200 will be explained with reference to FIG. 2.

Figure 2:
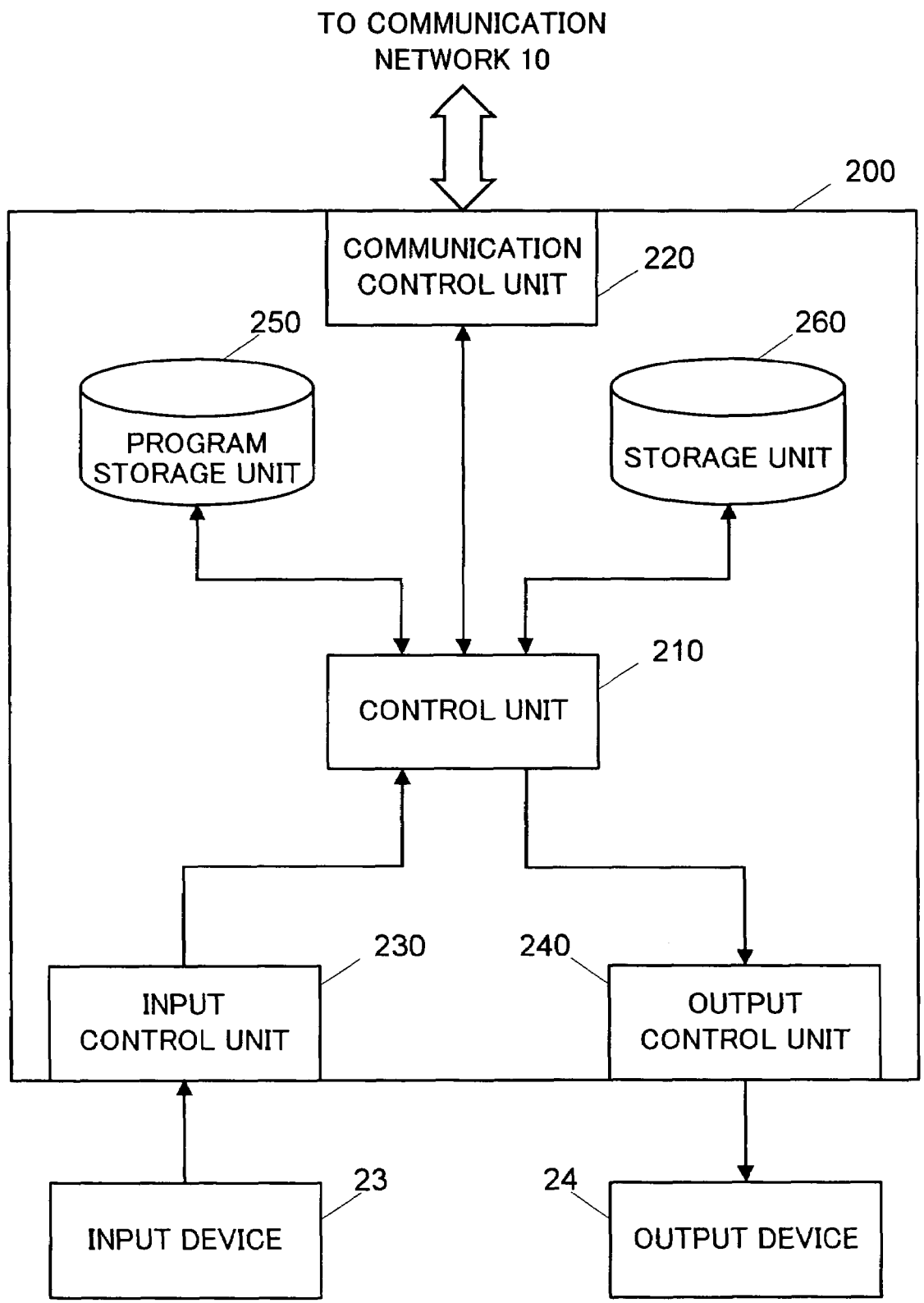
FIG. 2 is a block diagram showing a structure of a "control terminal" shown in FIG. 1.

FIG. 2 is a block diagram showing the structure of the control terminal 200. As shown in FIG. 2, the control terminal 200 comprises a control unit 210, a communication control unit 220, an input control unit 230, an output control unit 240, a program storage unit 250, and a storage unit 260.

The control unit 210 is constituted by, for example, a CPU (Central processing Unit) and a predetermined storage device (RAM (Random Access Memory) or the like) that serves as a work area. The control unit 210 controls each unit of the control terminal 200, and executes each process to be described below based on a predetermined operational program stored in the program storage unit 250.

The communication control unit 220 is constituted by, for example, a predetermined communication device such as a predetermined NIC (Network Interface Card). The communication control unit 220 connects the control terminal 200 to the modality 100 and the communication network 10, for performing communications with the modality 100 and the image processing apparatus 300.

The input control unit 230 is connected to a predetermined input device 23 such as, for example, a keyboard and a pointing device, etc. The input control unit 230 receives instructions, etc. to the control unit 210 which is input from the input device 23, and transmits the received instructions to the control unit 210.

The output control unit 240 is connected to a predetermined output device 24 such as, for example, a display device, a printer, etc. The output control unit 240 outputs a process result of the control unit 210 to the output device 24 if necessity arises.

The program storage unit 250 is constituted by a predetermined storage device such as a hard disk device, a ROM (Read Only Memory), etc. The program storage unit 250 stores various operational programs executed by the control unit 210. The program storage unit 250 stores an arbitrary OS (Operating System) that controls the basic operation of the control terminal 200, and operational programs shown in the following (1) and (2) for realizing each process to be described below in cooperation with the OS. The processes to be described below which are performed by the control terminal 200 are realized by the control unit 210 executing these operational programs.

"Modality control program": a program for controlling the modality 100.

Communication program": a program for controlling the communication control unit 220 and performing communications with the modality 100 and communications via the communication network 10.

The storage unit 260 is constituted by a storage device such as a RAM (Random Access Memory), a hard disk device, etc. The storage unit 260 stores acquired image data obtained from the modality 100, etc.

"Acquired image data" (original data) obtained from the modality 100 is "three-dimensional volume data" representing an image-acquired area. The three-dimensional volume data contains coordinate information of the area and characteristic information of each coordinate position. "Characteristic information" is information representing, when used in generating an image, characteristics (for example, brightness, chromaticness, color scheme, etc.) of picture elements (pixels, voxels) composing the image. Since in the present embodiment, a "CT scanner" is used as the modality 100, "CT values" are used as the characteristic information. "CT values" are values representing X-ray absorption factors. When an image is generated by using the CT values as picture element values, differences in the CT values are expressed as differences in the brightness in the image. Accordingly, by using "acquired image data" obtained from the modality 100, a tomographic image (slice image) shown in FIG. 3 can be acquired.

Figure 3:
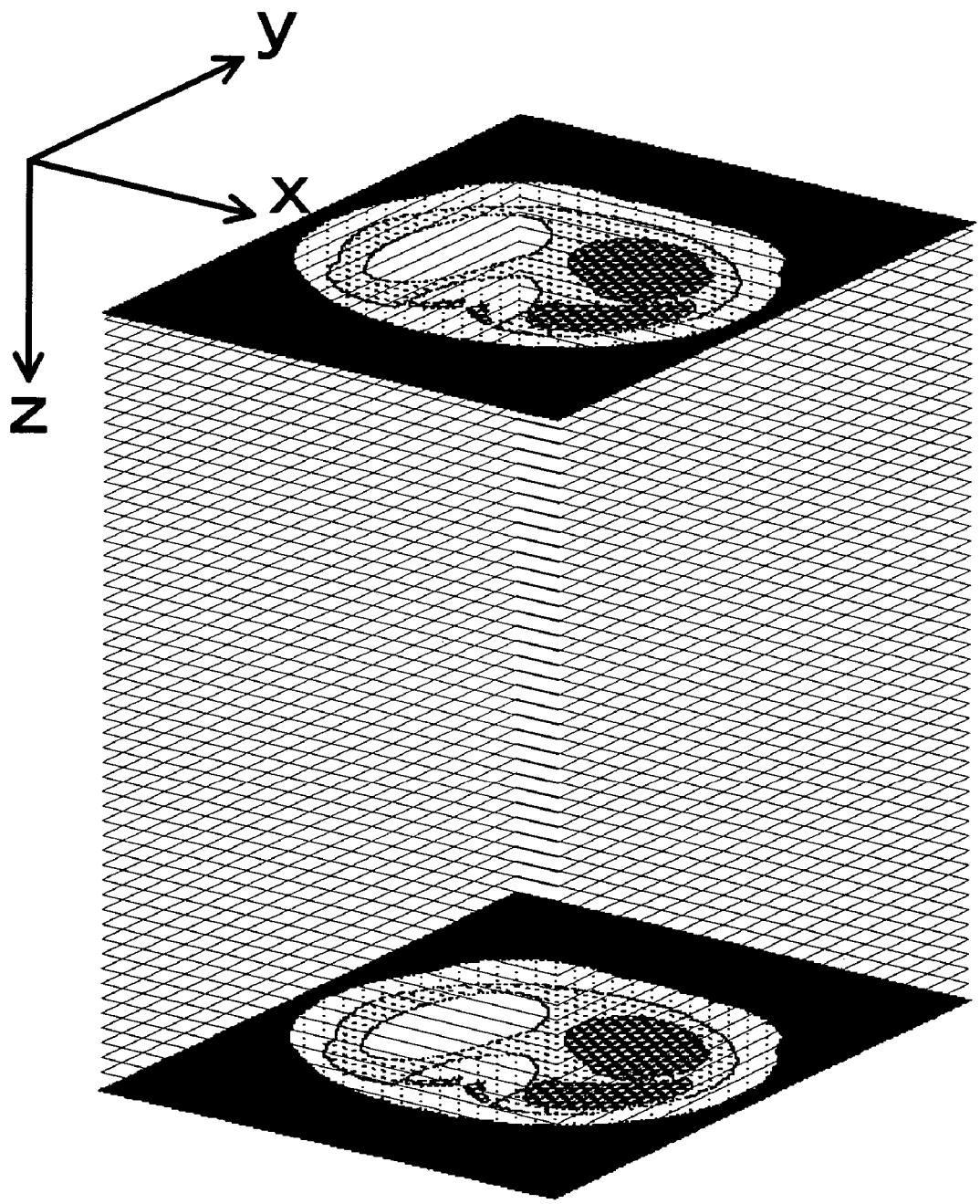
FIG. 3 is a diagram for explaining a tomographic image (slice) obtained by the control terminal shown in FIG. 2.
Figure 4A:
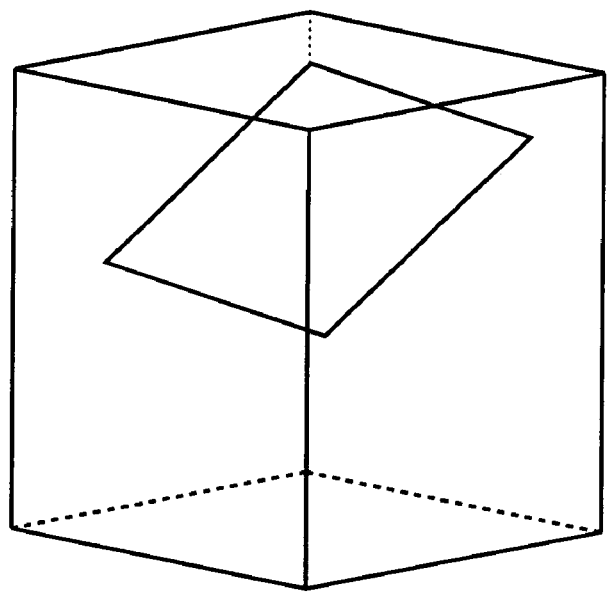
FIG. 4A shows an example of "MPR" and FIG. 4B shows an example of "CPR"
Figure 4B:
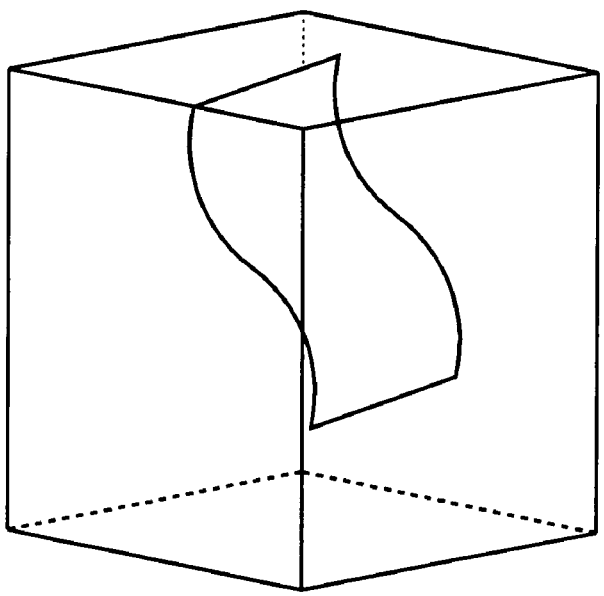

This tomographic image can be seen as a plurality of stacked two-dimensional images which are parallel, as shown in FIG. 3. This tomographic image can also be seen as a three-dimensional image wherein these stacked two-dimensional images are combined. That is, not only each of the stacked two-dimensional images can be extracted, but also an image of an arbitrary area or a plane can be designated from the entire three-dimensional image. A method called MPR (Multi Planer Reconstruction) has been known as a method of designating an arbitrary plane. According to this method, an arbitrary plane in the three-dimensional volume data can be designated, as shown in FIG. 4A. Further, a method called CPR (Curved Planer Reconstruction) has been known as a method of designating an arbitrary curved plane. According to this method, an arbitrary curved plane in the three-dimensional volume data can be designated, as shown in FIG. 4B.

The image processing apparatus 300 will be explained next. The image processing apparatus 300 is constituted by a predetermined information processing apparatus such as a workstation. The image processing apparatus 300 generates a three-dimensional diagnosis image (medical image) by using acquired image data (three-dimensional volume data) obtained from the control terminal 200. The structure of the image processing apparatus 300 will be explained with reference to FIG. 5.

Figure 5:
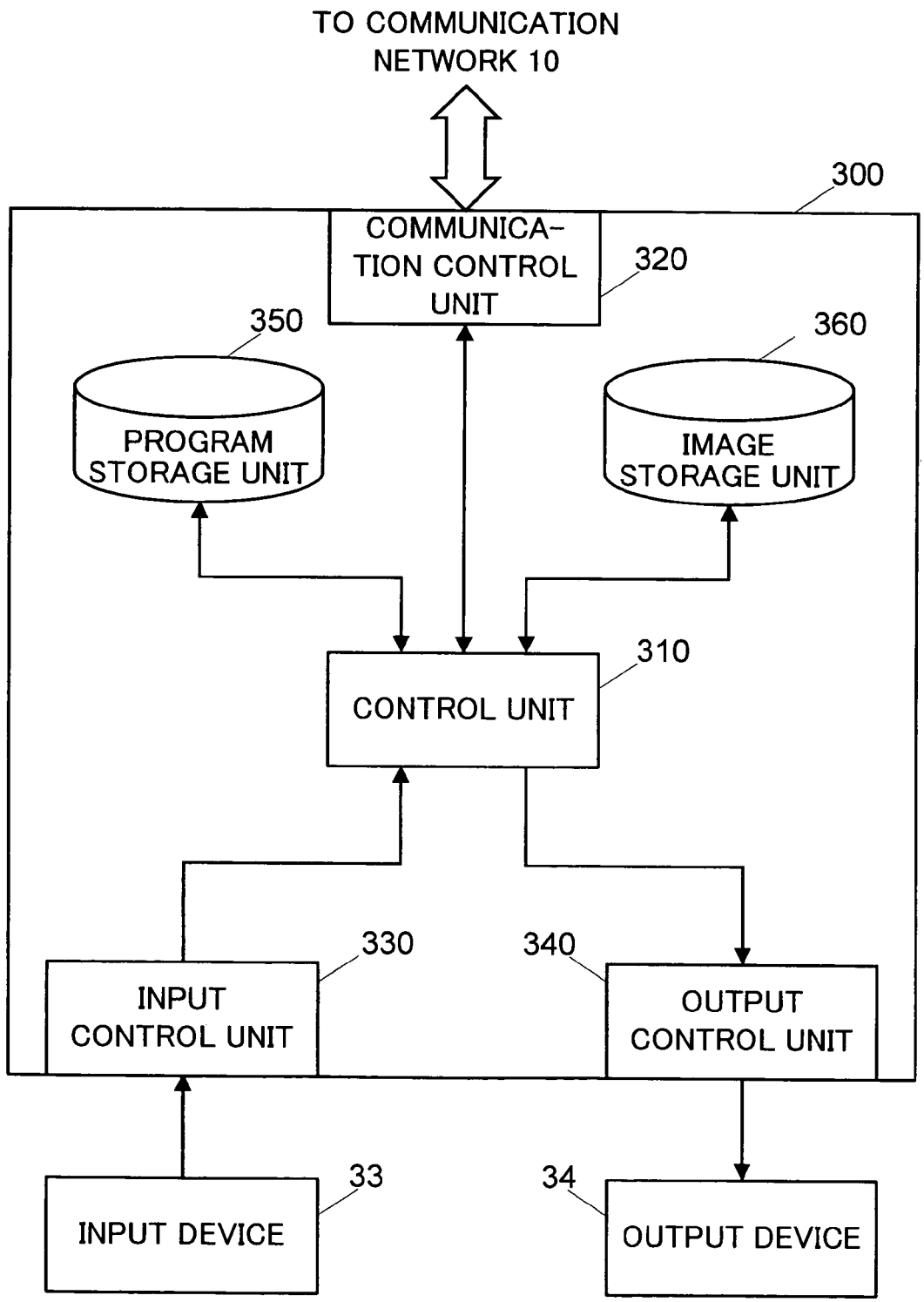
FIG. 5 is a block diagram showing a structure of an "image processing apparatus" shown in FIG. 1.

FIG. 5 is a block diagram showing the structure of the image processing apparatus 300. As shown in FIG. 5, the image processing apparatus 300 comprises a control unit 310, a communication control unit 320, an input control unit 330, an output control unit 340, a program storage unit 350, and an image storage unit 360.

The control unit 310 is constituted by, for example, a CPU (Central Processing Unit) and a predetermined storage device (RAM (Random Access Memory), etc.) used as a work area. The control unit 310 controls each unit of the image processing apparatus 300, and performs each process to be described below based on predetermined operational programs stored in the program storage unit 350.

The communication control unit 320 is constituted by a predetermined communication device such as a predetermined NIC (Network Interface Card). The communication control unit 320 connects the image processing apparatus 300 to the communication network 10, for performing communications with the control terminal 200, etc.

The input control unit 330 is connected to a predetermined input device 33 such as, for example, a keyboard, a pointing device, etc. The input control unit 330 receives instructions to the control unit 310, information to be stored in each database, etc which are input from the input device 33, and transmits them to the control unit 310.

The output control unit 340 is connected to a predetermined output device 34 such as, for example, a display device, a printer, etc. The output control unit 340 outputs a process result of the control unit 310, etc. to the output device 34 in accordance with necessity.

The program storage unit 350 is constituted by a predetermined storage device such as a hard disk device, a ROM (Read Only Memory), etc. The program storage unit 350 stores various operational programs executed by the control unit 310. The operational programs stored in the program storage unit 350 includes, other than an arbitrary OS (Operating System) that controls the basic operation of the image processing apparatus 300, operational programs shown in the following (1) to (3) for realizing each process to be described below in cooperation with the OS. The processes to be described below which are performed by the image processing apparatus 300 are realized by the control unit 310 executing these operational programs.

"Communication program": a program for controlling the communication control unit 320 and performing communications with the control terminal 200 via the communication network 10.

"DB control program": a program for controlling the image storage unit 360.

"Image processing program": a program for applying image processing to acquired image data obtained from the control terminal 200.

The image storage unit 360 is constituted by a rewritable storage device such as, for example, a semiconductor storage device, a hard disk device, etc. The image storage unit 360 stores data acquired from each process to be described below and three-dimensional diagnosis image to be generated in each process to be described below.

Each process in the present embodiment will now be explained with reference to the drawings. In the present embodiment, an image diagnosis system 1 to which the present invention is applied will generate a medical image to be used in image diagnosis, by extracting only a desired vessel (a vessel to be medically examined, diagnosed, or observed, and referred to as "target vessel" hereinafter) from three-dimensional volume data acquired by the modality 100.

Figure 6:
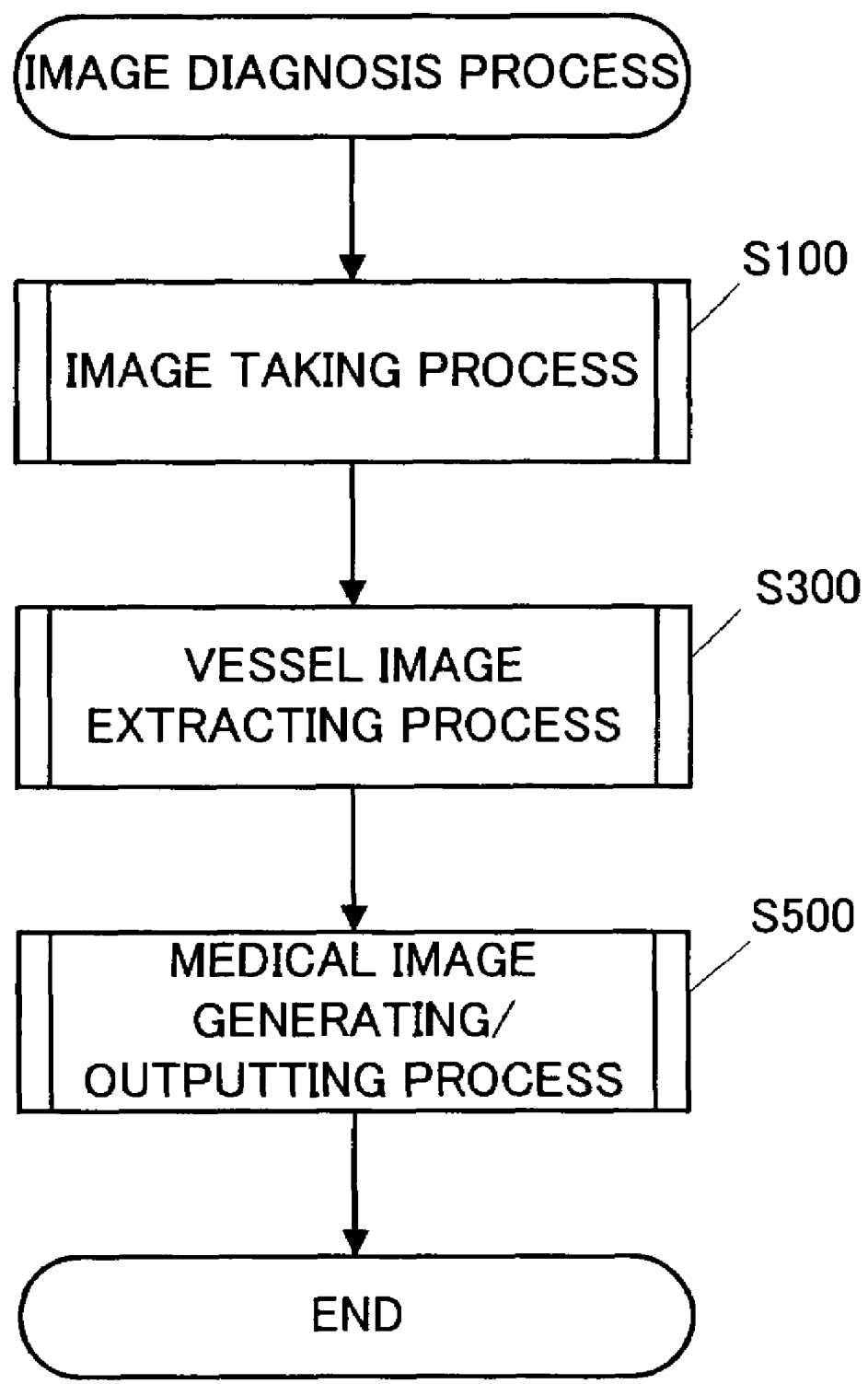
FIG. 6 is a flowchart for explaining an "image diagnosis process" according to an embodiment of the present invention.

FIG. 6 is a flowchart for explaining an "image diagnosis process" for conducting image diagnosis by the image diagnosis system 1 to which the present invention is applied. As shown in FIG. 6, for the image diagnosis system 1 to perform image diagnosis, an "image acquiring process" (step S100), a "vessel image extracting process" (step S300), and a "medical image generating/outputting process" (step S500) will be sequentially performed. The detail of each of these processes will now be explained with reference to the drawings.

Figure 7:
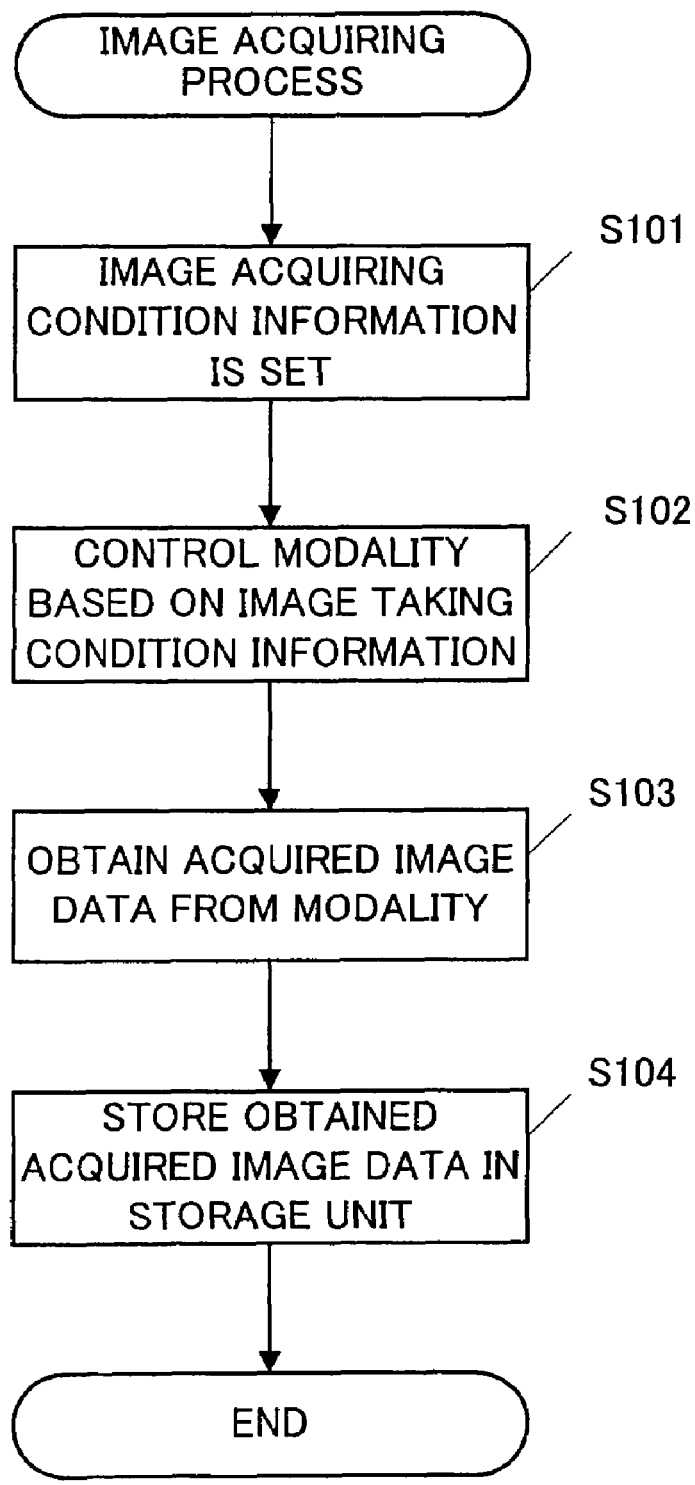
FIG. 7 is a flowchart for explaining an "image taking process" shown in FIG. 6.

The "image acquiring process" according to the present embodiment will first be explained with reference to a flowchart in FIG. 7. This process is for acquiring a tomographic image (slice) of the inside of a medical examinee, etc. by cooperation of the modality 100 and the control terminal 200. The operation of the control terminal 200 will be mainly explained below. The control terminal 200 performs the following process by executing the "modality control program" in the program storage unit 250.

In performing the image acquiring operation, predetermined image acquiring condition information is set at the control terminal 200 (step S101). In this step, various conditions for image acquiring, such as designation of an image acquiring target area, use or non-use of a contrast medium, etc. are set.

The control terminal 200 controls the modality 100 in accordance with the image acquiring conditions set in step S101 (step S102). That is, the modality 100 performs an image acquiring operation based on the above image acquiring conditions under the control of the control terminal 200. As a result, the modality 100 obtains acquired image data (three-dimensional volume data) of the set image acquiring target area.

When the image acquiring operation of the modality 100 is completed, the control terminal 200 receives the obtained acquired image data from the modality 100 (step S103). Then, the control terminal 200 stores the received acquired image data in the storage unit 260 (step S104), and finishes this process.

In the "image diagnosis process" (FIG. 6) according to the present embodiment, the "vessel image extracting process" for generating a three-dimensional image representing a vessel is performed by using the thusly obtained data (three-dimensional volume data). This "vessel image extracting process" employs roughly two process methods, namely (1) a vessel center line extracting method, and (2) a continuous region specifying method. These methods will be referred to as "first process method" and "second process method". The vessel image extracting process using each of the methods, and the medical image generating/outputting process will now be sequentially explained. The processes to be described below are performed by the control unit 310 of the image processing apparatus 300 executing the "image processing program" in the program storage unit 350.

(First Process Method)

The vessel image extracting process employing the vessel center line extracting method will be explained with reference to a flowchart shown in FIG. 8. In this process, the center line of a desired vessel is extracted as three-dimensional path data by using the acquired image data obtained in the "image acquiring process". In the present embodiment, explanation will be made by employing a case where a coronary vessel around a heart is the target of extraction as an example.

First, the image processing apparatus 300 obtains the process target acquired image data (three dimensional volume data) from the control terminal 200 via the communication network 10 (step S301).

Then, the control unit 310 displays a two-dimensional image based on the acquired image data (three-dimensional volume data) obtained in step S301 on the output device 34 (display device). The control unit 310 receives designation of an extraction start point and extraction end point of the extraction target vessel (hereinafter referred to as "target vessel Vt") (step S302). Here, an operator such as a doctor operates the input device 33 and designates the extraction start point and extraction end point on the displayed two-dimensional image.

Figure 9A:
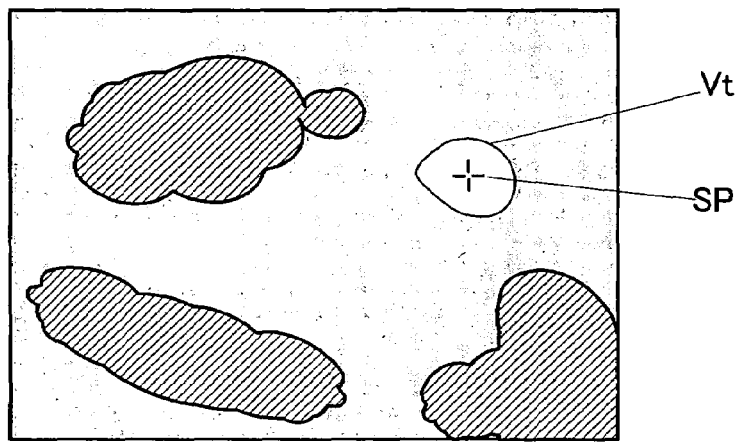
FIG. 9A shows an example of a cross sectional image displayed for designation of a start point, FIG. 9B exemplarily shows a positional relationship between an obtained cross sectional region and a target vessel, etc.

FIG. 9A shows an example of the two-dimensional image displayed in this step. An image representing an arbitrary two-dimensional plane in the image-acquired area that is obtained by the above mentioned MPR or the like is displayed on the output device 34. That is, the corresponding area is imaged (turned into an image) by expressing darkness and brightness based on the differences in the CT values included in the three-dimensional volume data. The image processing apparatus 300 arbitrarily changes the display such that the position or angle of display is changed, by data-converting the three-dimensional volume data corresponding to a position or direction designated by the operator by operating the input device 33. In a case where a vessel is the target of image acquiring, a contrast medium is usually used to raise the CT values of the blood. Due to this, the vessel portion is displayed relatively brightly, as shown in FIG. 9A. The operator operates the input device 33 and changes the display screen so that a cross sectional view of the target vessel Vt at the extraction start point will be displayed. The operator designates the center of the displayed cross sectional view (the center will hereinafter be referred to as "start point SP"), by using the input device 33. Further, the operator likewise designates the center of a cross sectional view at the extraction end point (the center will hereinafter be referred to as "end point EP").

When the start point SP is designated in step S302, the control unit 310 of the image processing apparatus 300 specifies the three-dimensional coordinates (x, y, z) of the start point SP. Then, the control unit 310 specifies a region (surface) (hereinafter referred to as "orthogonal cross sectional region SR) in whose enter the start point SP is positioned and which is orthogonal to the longitudinal direction of the target vessel Vt passing through this center position, based on the specified coordinates (step S303). This orthogonal cross sectional region SR is a quadrilateral plane which has a certain width and a certain length. An operator designates the orientation of the orthogonal cross sectional region to be orthogonal to the vessel Vt.

Figure 9B:
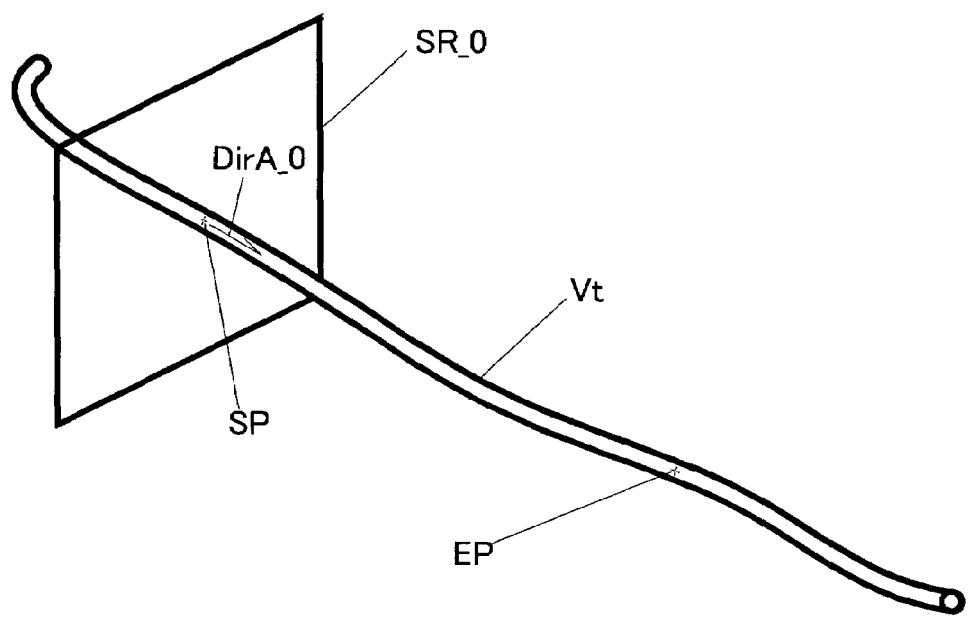
FIG. 9 are diagrams for explaining cross sectional regions obtained by the vessel image extracting process shown in FIG. 8, where
FIG. 9C exemplarily shows a positional relationship between an obtained cross sectional region and a cross section of a vessel.
Figure 9C:
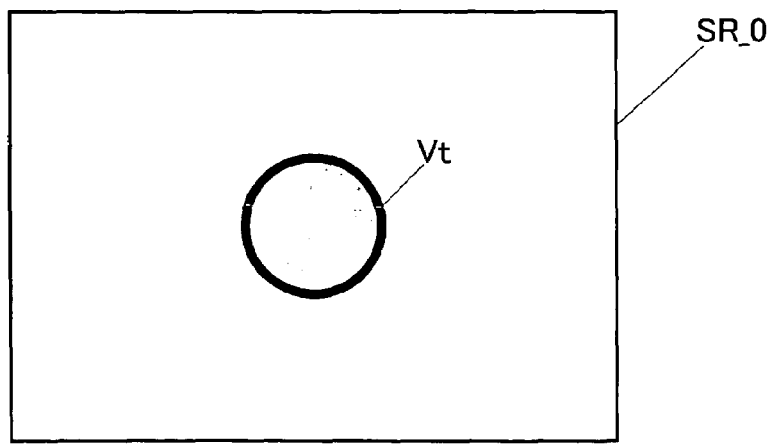

FIG. 9B and FIG. 9C show examples of the positional relationship among the points designated in step S302, the target vessel Vt, and the orthogonal cross sectional region SR specified in step S303. FIG. 9B is a diagram exemplarily showing the positional relationship among the target vessel Vt, the designated start point SP and end point EP, and an orthogonal cross sectional region SR_0 specified at the start point SP. FIG. 9C is an exemplary diagram showing the position of the target vessel Vt in the orthogonal cross sectional region SR_0. When the start point SP and end point EP are designated on the target vessel Vt (FIG. 9B), the orthogonal cross sectional region SR_0 in whose center the start point SP is positioned is specified (FIG. 9C).

In the present embodiment, the orthogonal cross sectional region SR is sequentially specified from the start point SP to the end point EP, by a later-described process. Accordingly, the orthogonal cross sectional region specified at the position of the start point SP will hereinafter be referred to as "orthogonal cross sectional region SR_0", and the orthogonal cross sectional region specified at the position of the end point EP will hereinafter be referred to as "orthogonal cross sectional region SR_n". That is, the orthogonal cross sectional regions SR_0 to SR_n will be sequentially specified in the process to be described later.

The control unit 310 retains the coordinates of the start point SP and end point EP designated in step S302 in a predetermined storage area such as a work area. After this, the control unit 310 determines in which direction the target vessel Vt is to be extracted, based on the positions of the start point SP and end point EP. Then, the control unit 310 determines which surface of the orthogonal cross sectional region SR_0 is the surface at the marching (advancing, progressing) direction side (hereinafter referred to as "principal surface"), based on the determined direction (marching (advancing, progressing) direction). The control unit 310 determines a direction that is perpendicular to the determined principal surface and almost coincides with the direction in which the determined principal surface is oriented as a "temporary marching (advancing, progressing) direction" DirA (step S304). The temporary marching (advancing, progressing) direction is determined by the following process for each of the orthogonal cross sectional regions SR_0 to SR_n. Accordingly, temporary marching (advancing, progressing) directions respectively corresponding to the orthogonal cross sectional regions SR_0 to SR_n will be represented as "temporary marching (advancing, progressing) directions DirA_0 to DirA_n" in the following explanation.

The temporary marching (advancing, progressing) direction DirA_0 shown in FIG. 9B is determined in step S304.

Figure 10:
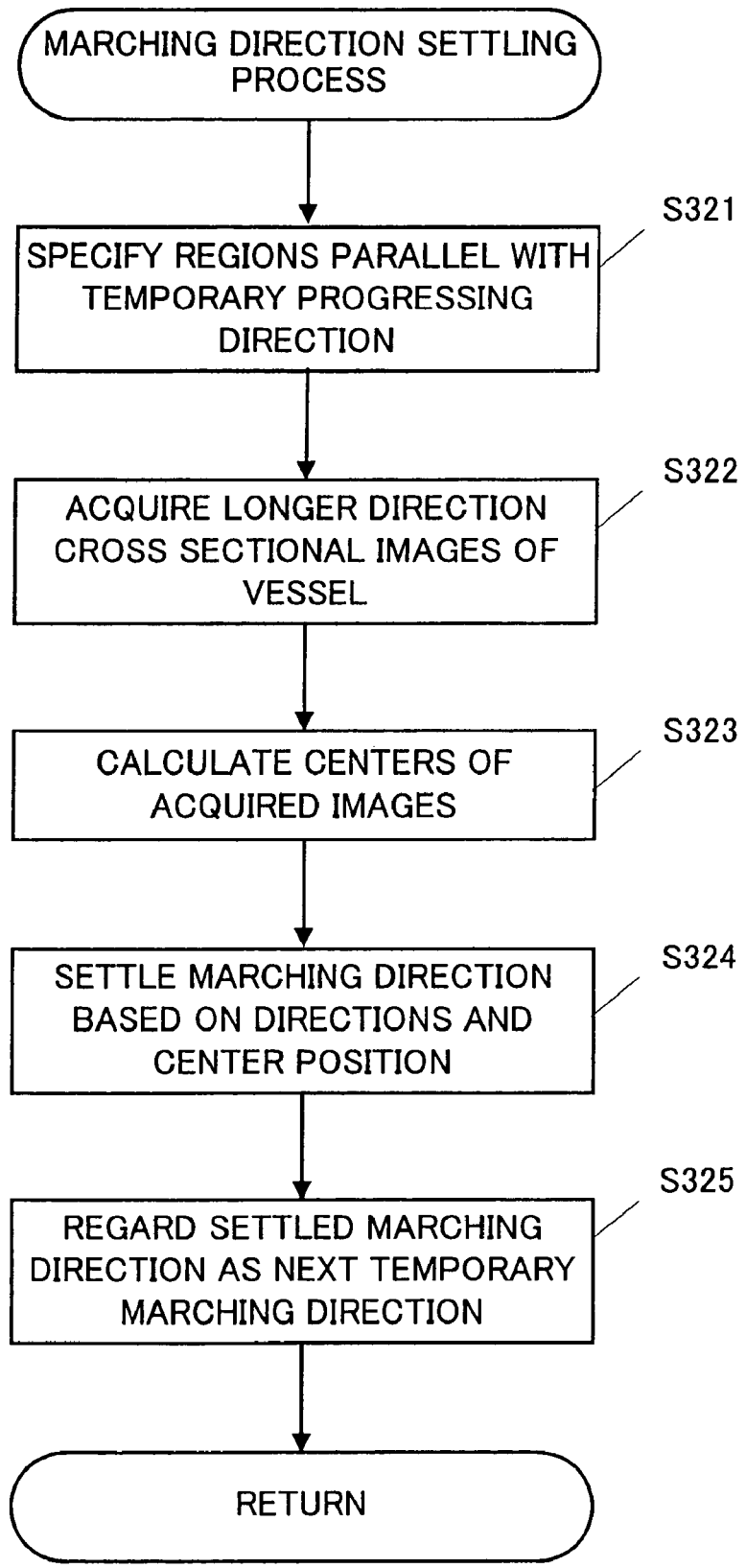
FIG. 10 is a flowchart for explaining a "marching (advancing, progressing) direction settling process" in the vessel image extracting process shown in FIG. 8.

When the temporary marching (advancing, progressing) direction is determined, the control unit 310 performs a "marching (advancing, progressing) direction settling process" (step S320) for determining the position for specifying the orthogonal cross sectional region SR to be specified next (here, an orthogonal cross sectional region SR_1 which is an area next to the orthogonal cross sectional region SR_0 based on the determined temporary marching (advancing, progressing) direction. This "marching (advancing, progressing) direction settling process" will be explained with reference to a flowchart shown in FIG. 10.

By regarding the start point SP designated in step S302 as an origin, the control unit 310 specifies two certain-sized quadrilateral regions parallel with the temporary marching (advancing, progressing) direction (here, the temporary marching (advancing, progressing) direction DirA_0) and each including a cross sectional surface of the longitudinal direction of the target vessel Vt obtained at the origin position (hereinafter, one region will be referred to as "parallel cross sectional region PR1" and the other "parallel cross sectional region PR2") (step S321). In the present embodiment, each time the orthogonal cross sectional region SR is sequentially specified, the parallel cross sectional regions PR1 and PR2 are specified. Accordingly, the parallel cross sectional regions respectively corresponding to the orthogonal cross sectional regions SR_0 to SR_n will be represented as "parallel cross sectional regions PR1_0 to PR1_$n$" and "parallel cross sectional regions PR2_0 to PR2_$n$". FIG. 11 exemplarily show the positional relationships of the parallel cross sectional regions PR1_0 and PR2_0.

Figure 11A:
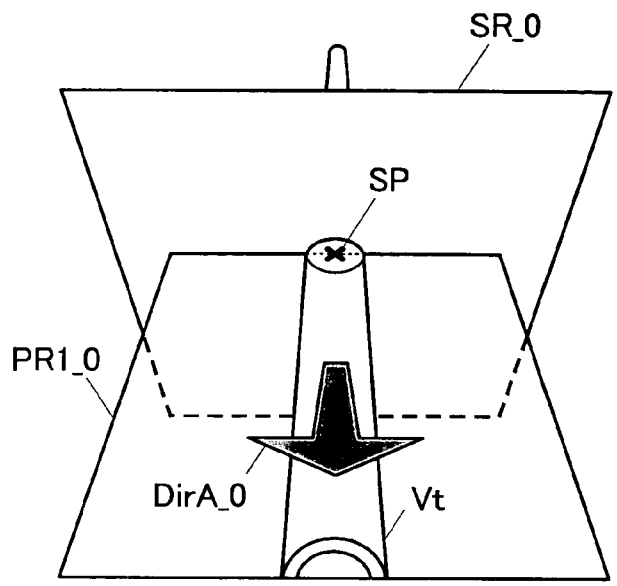
FIG. 11 are diagrams for explaining parallel cross sectional regions specified in the marching (advancing, progressing) direction settling process shown in FIG. 10, where FIG. 11A exemplarily shows a positional relationship of one of specified parallel cross sectional regions, FIG. 11B exemplarily shows a positional relationship of the other of the specified cross sectional regions, and FIG. 11C exemplarily shows a positional relationship between both of the specified parallel cross sectional regions and a orthogonal cross sectional region.
Figure 11B:
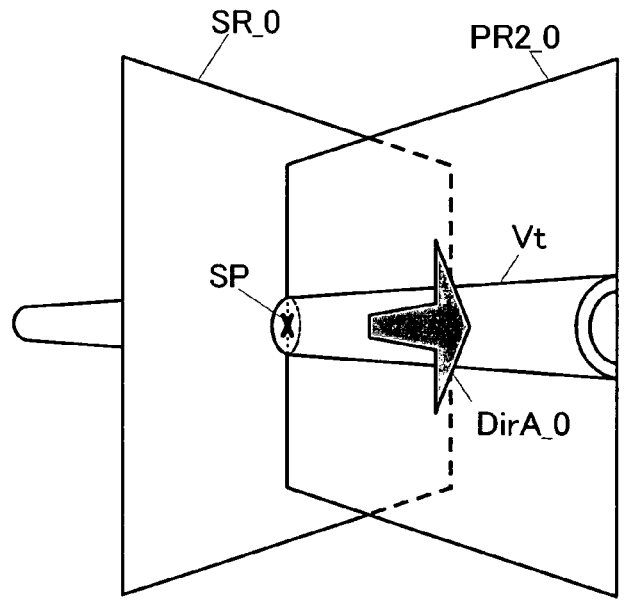
Figures 11C, 11D:
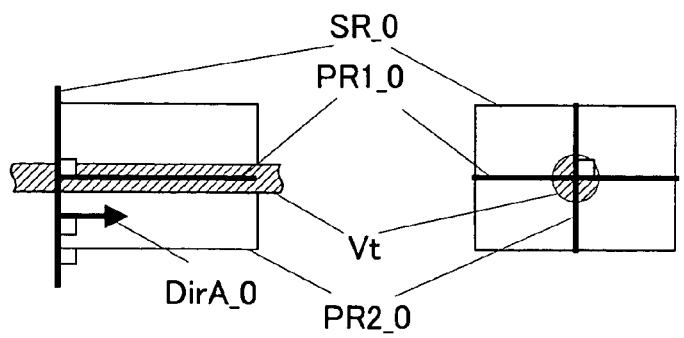

FIG. 11A exemplarily shows the positional relationship among the parallel cross sectional region PR1_0, the orthogonal cross sectional region SR_0, and the start point SP. FIG. 11B exemplarily shows the positional relationship among the parallel cross sectional region PR2_0, the orthogonal cross sectional region SR_0, and the start point SP. FIG. 11C and FIG. 11D exemplarily shows the positional relationship among the orthogonal cross sectional region SR_0, and the parallel cross sectional regions PR1_0 and PR2_0. FIG. 11C is a diagram seen from a direction perpendicular to the vessel Vt. FIG. 11D is a diagram seen from a direction parallel to the vessel Vt.

The temporary marching (advancing, progressing) direction DirA_0 is a direction perpendicular to the principal surface of the orthogonal cross sectional region SR_0. Therefore, the parallel cross sectional regions PR1_0 and PR2_0 are also perpendicular to the principal surface of the orthogonal cross sectional region SR_0, as shown in FIGS. 11A to 11D. Further, the control unit 310 specifies the regions such that the parallel cross sectional regions PR1_0 and PR2_0 are perpendicular to each other. In addition, the control unit 310 specifies the parallel cross sectional regions PR1_0 and PR2_0 such that they contact the principal surface of the orthogonal cross sectional region SR_0, and their contacting sides are on the start point SP. Due to this, each of the parallel cross sectional regions PR1_0 and PR2_0 includes a cross sectional surface of the longitudinal direction of the target vessel Vr fit inside its region.

Figure 12A:
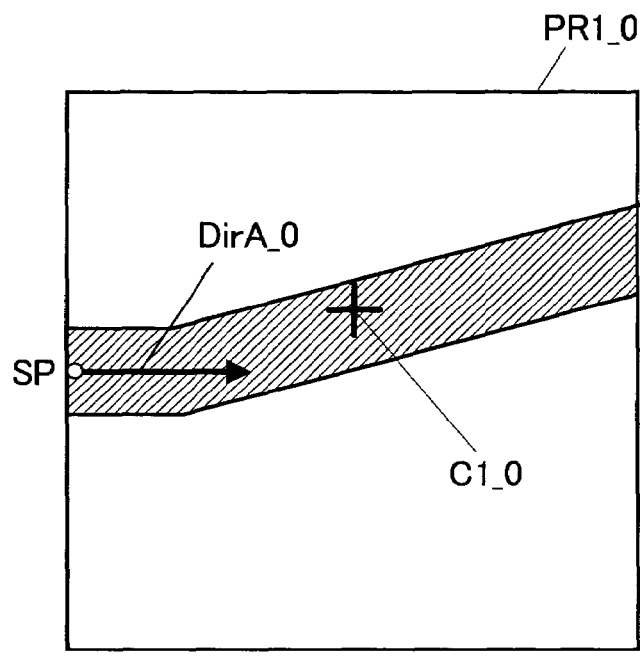
FIG. 12A shows an example of a longitudinal direction image obtained in the one parallel cross sectional region.
Figure 12B:
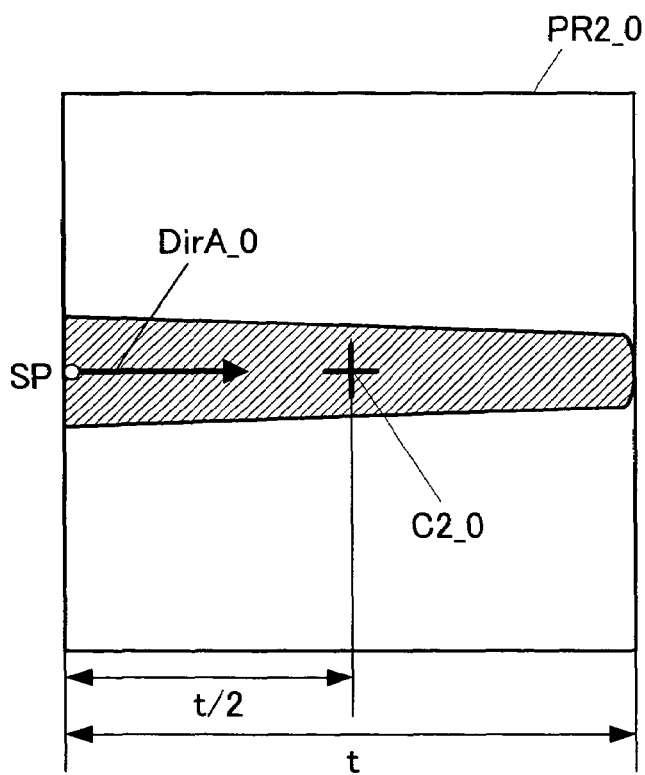
FIG. 12B shows an example of a longitudinal direction image obtained in the other parallel cross sectional region.

The control unit 310 images the specified parallel cross sectional regions PR1_0 and PR2_0 by using the volume data representing these regions (step S322). That is, the control unit 310 acquires (generates) such images as shown in FIGS. 12A and 12B representing cross sectional surfaces of the longitudinal direction of the target vessel Vt (hereinafter referred to as "longitudinal direction cross sectional images").

If it is assumed that the target vessel Vt extends linearly, image data of the vessel can be extracted by processing the image data along the temporary marching (advancing, progressing) direction DirA which is perpendicular to the principal surface of the orthogonal cross sectional region SR. However, since the vessel extends by changing its extending direction three-dimensionally, the longitudinal direction cross sectional image to be acquired is not necessarily parallel with the temporary marching (advancing, progressing) direction DirA_0, as shown in FIG. 12A. Thus, the control unit 310 corrects the temporary marching (advancing, progressing) direction DirA_0 to the actual extending direction of the vessel Vt based on the acquired longitudinal direction cross sectional image.

First, the control unit 310 obtains center positions of the respective longitudinal direction cross sectional images acquired in step S322 (step S323). That is, the control unit 310 calculates the positions of centers C1_0 and C2_0 shown in FIGS. 12A and 12B. The control unit 310 recognizes (determines) the longitudinal direction cross sectional image region (regions shown in FIG. 12A and FIG. 12B by hatching) of the vessel in the respective parallel cross sectional regions PR1_0 and PR2_0 by using "Flood Fill" method or the like, and obtains the centers C1_0 and C2_0 of the respective longitudinal direction cross sectional images. Since the center position is obtained at each of the parallel cross sectional regions PR1_0 to PR1_$n$ and parallel cross sectional regions PR2_0 to PR2_$n$ in the following process, the centers respectively corresponding to the parallel cross sectional regions PR1_0 to PR1_$n$ and parallel cross sectional regions PR2_0 to PR2_$n$ will be represented as "centers C1_0 to C1_$n$" and "centers C2_0 to C2_$n$".

Next, the control unit 310 obtains a "vector of the actual extending direction" that represents the direction of the extension of the vessel Vt by using each center position C1_0 and C2_0 obtained in step S323 (step S324). That is, this "vector of the actual extending direction" is a vector that starts from the start point SP of the target vessel to the actual position that is apart by a distance of t/2 (t is the width of the parallel cross sectional regions PR1_0 and PR2_0) from the start point SP. Here, the control unit 310 can obtain the vector of the extending direction of the target vessel Vt that starts from the orthogonal cross sectional region SR_0 by, for example, calculating numerical formulae shown in FIG. 13.

That is,
In the case V2■n1>V3■n1,
The vector parallel to the actual extending direction=v2'■n1*n1+v2'■n3*n3+v3■n2*n2
where, v2'=v3■n1/v2■n1*v2
In the case V2■n1≦V3■n1,
The vector parallel to the actual extending direction=v2■n1*n1+v2■n3*n3+v3'■n2*n2
where, v3'=v2■n1/v3■n1*v3

In the above Formulae, ■ represents inner products of vectors, and * represents outer products of vectors.

Figure 14A:
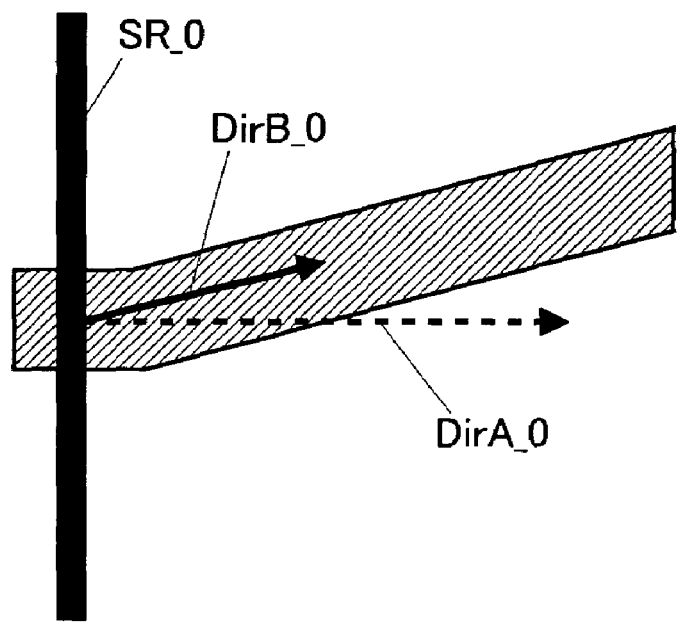
FIG. 14 are diagrams for explaining a process included in the marching (advancing, progressing) direction settling process shown in FIG. 10, where FIG. 14A exemplarily shows a relationship between a temporary marching (advancing, progressing) direction and a settled marching (advancing, progressing) direction, and FIG. 14B exemplarily shows an orthogonal cross sectional region which is specified based on the settled marching (advancing, progressing) direction.

By this vector calculation, a direction DirB_0 shown in FIG. 14A, which is the actual extending direction, can be obtained. That is, the temporary marching (advancing, progressing) direction DirA_0 is corrected to the marching (advancing, progressing) direction DirB_0. Hereinafter, a direction obtained in this manner will be represented as "settled marching (advancing, progressing) direction DirB". The settled marching (advancing, progressing) direction DirB is obtained for each of the orthogonal cross sectional regions SR_0 to SR_n in the following process. Therefore, the settled marching (advancing, progressing) directions DirB corresponding to the respective orthogonal cross sectional regions will be represented as "settled marching (advancing, progressing) directions DirB_0 to DirB_$n$".

The control unit 310 regards the thusly obtained settled marching (advancing, progressing) direction DirB_0 as a marching (advancing, progressing) direction for determining the position of a cross sectional region to be specified next to the orthogonal cross sectional region SR_0 (i.e. the orthogonal cross sectional region SR_1). Further, the control unit 310 stores the settled marching (advancing, progressing) direction DirB_0 in the work area or the like as a temporary marching (advancing, progressing) direction to be used for determining the next marching (advancing, progressing) direction (the extending direction from the orthogonal cross sectional region SR_1 to the next orthogonal cross sectional region SR_2) (step S325), and completes the "marching (advancing, progressing) direction settling process" for the orthogonal cross sectional region SR_0.

Figure 8:
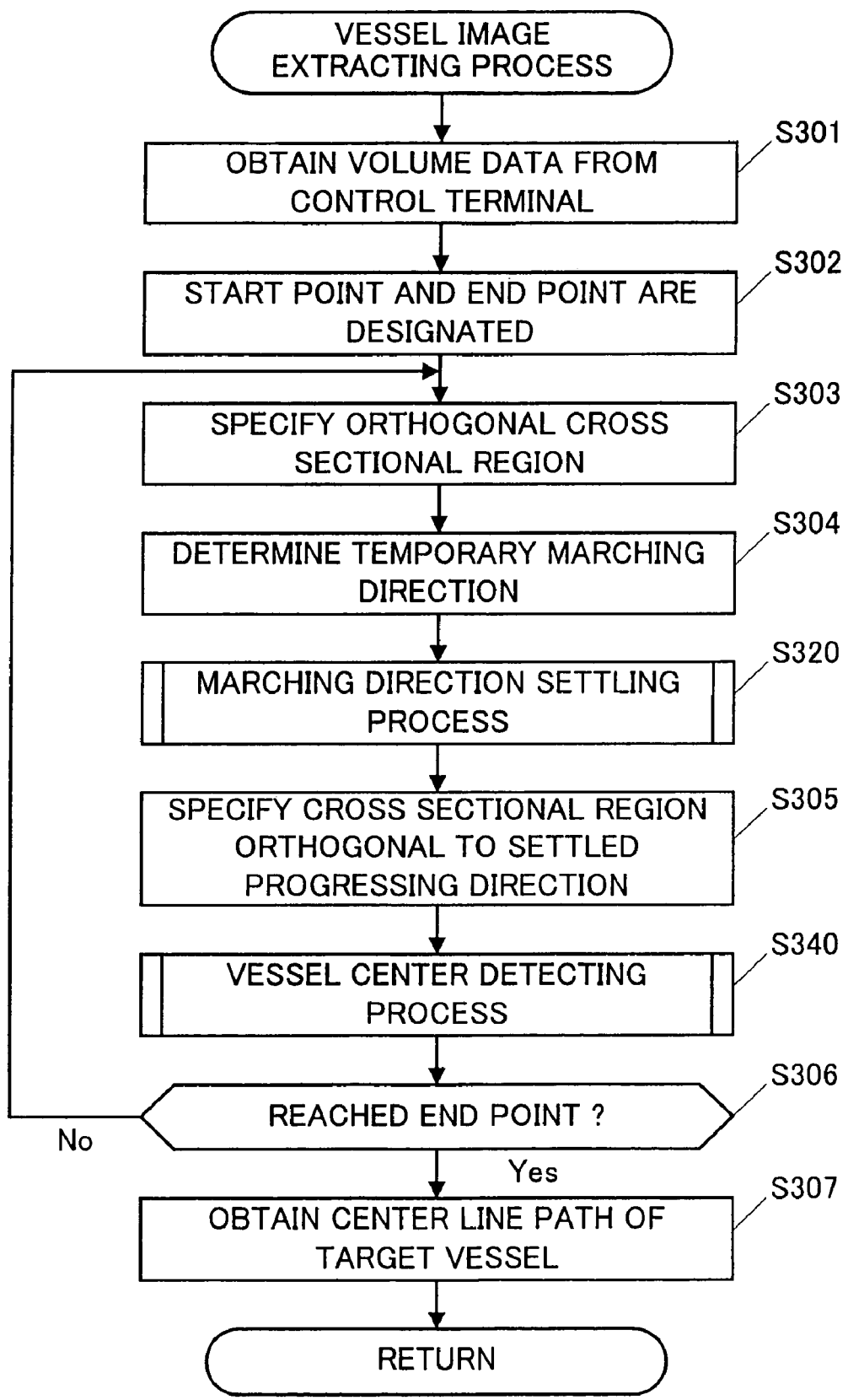
FIG. 8 is a flowchart for explaining a "vessel image extracting process" shown in FIG. 6.
Figure 14B:
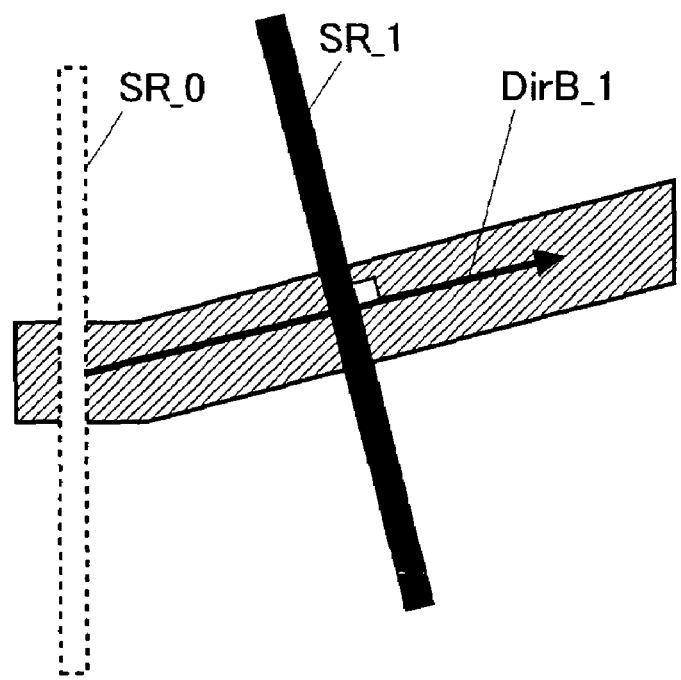

Returning to the flow of the "vessel image extracting process" shown in FIG. 8, the control unit 310 specifies the next orthogonal cross sectional region SR (in this case, the orthogonal cross sectional region SR_1) that is orthogonal to the settled marching (advancing, progressing) direction DirB_0 obtained in step S325, by the same procedure as step S303 (step S305). That is, such an orthogonal cross sectional region SR_1 as shown in FIG. 14B is specified. The distance between the formerly specified cross sectional region to the next specified cross sectional region is arbitrarily set in accordance with the process capacity of the image processing apparatus 300, a desired precision, etc.

The orthogonal cross sectional region SR_1 specified in step S305 is oriented in a direction orthogonal to the settled marching (advancing, progressing) direction DirB_0 originating from the start point SP which is the center of the orthogonal cross sectional region SR_0 immediately before the region SR_1. Therefore, the newly specified orthogonal cross sectional region SR_1 is also a region which is in a cross sectional direction of the target vessel Vt and in whose center the center of the cross section is positioned, likewise the orthogonal cross sectional region SR_0.

Figure 15A:
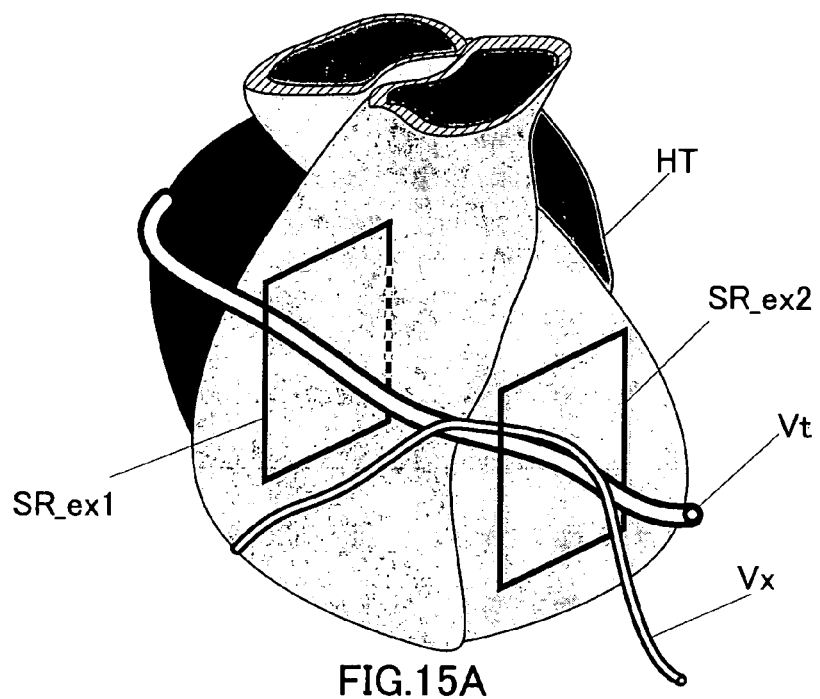
FIG. 15 are diagrams exemplarily showing a positional relationship of a target vessel, where FIG. 15A exemplarily shows a positional relationship between orthogonal cross sectional regions specified for a target vessel, and a heart and another vessel which are close to the target vessel, FIG. 15B exemplarily shows a positional relationship between the target vessel and the heart in one orthogonal cross sectional region shown in FIG. 15A, and FIG. 15C exemplarily shows a positional relationship between the target vessel and the another vessel in the other orthogonal cross sectional region shown in FIG. 15A.
Figure 15B:
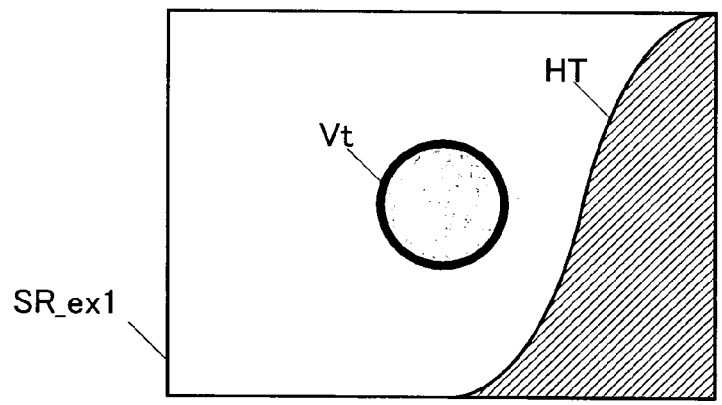
Figure 15C:
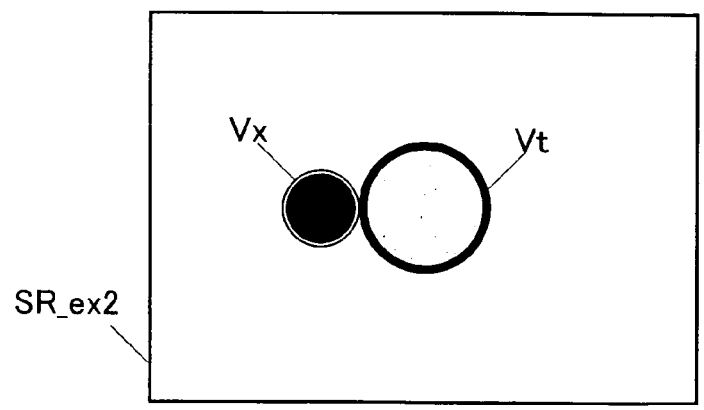

In such a case as shown in FIG. 9C where the cross section of the vessel only exists in the concerned orthogonal cross sectional region SR, the extraction of the cross section of the vessel and the center of the vessel is easy. However, as shown in FIG. 15A, in many cases, the target vessel Vt in the specified orthogonal cross sectional region SR is close to a heart HT or another vessel Vx than the target vessel Vt. For example, an orthogonal cross sectional region SR ("orthogonal cross sectional region SR_ex1" in FIG. 15A) obtained at a place where the target vessel Vt is close to the heart HT, includes portions of the heart HT in addition to the cross section of the target vessel Vt, as shown in FIG. 15B. Further, an orthogonal cross sectional region SR ("orthogonal cross sectional region SR_ex2" in FIG. 15A) obtained at a place where the target vessel Vt is close to another vessel Vx includes the cross section of the vessel Vx in addition to the cross section of the target vessel Vt, as shown in FIG. 15C.

Figure 16A:
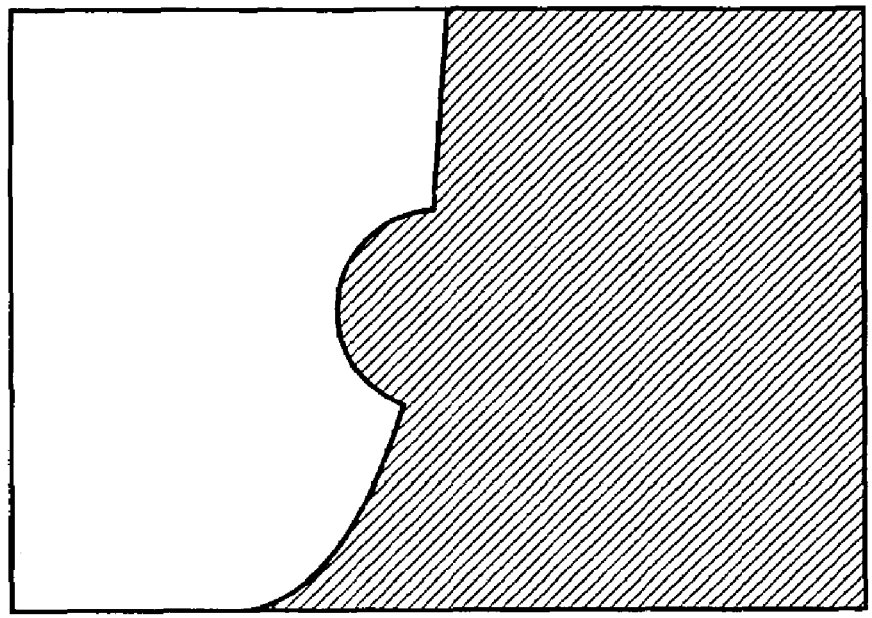
FIG. 16A shows an example of the image of the region shown in FIG. 15B.
Figure 16B:
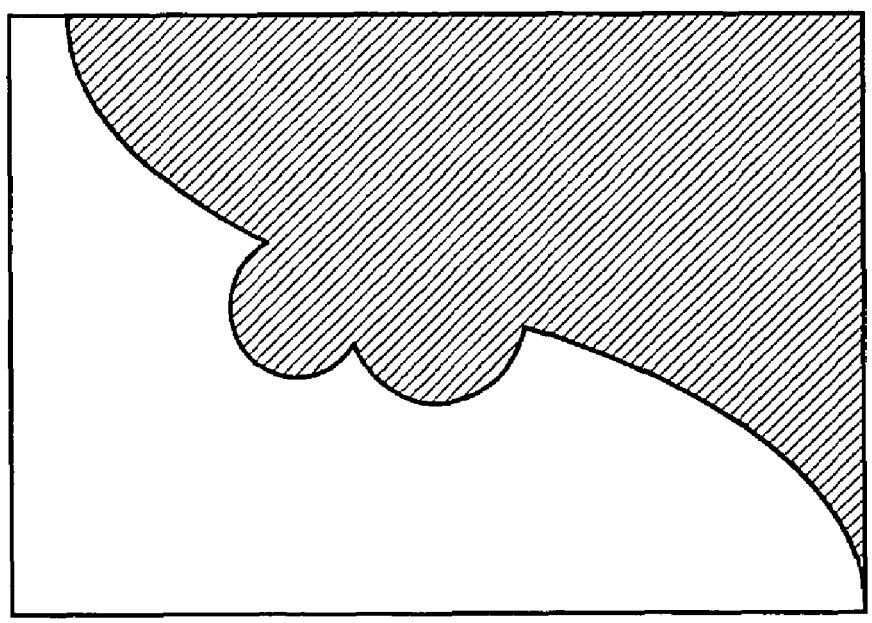
FIG. 16B shows an example of the image of the region shown in FIG. 15C.

In these cases, in order to determine the cross section and center of the target vessel Vt, the orthogonal cross sectional region may be imaged. That is, the orthogonal cross sectional region may be imaged based on the CT values indicating this orthogonal cross sectional region, and the cross section of the target vessel Vt may be extracted as an image. The CT values are X-ray absorption factors acquired by the modality 100 (CT scanner), and materials have their own fixed CT values, such as, for example, "water: 0", "air: −1000", etc. Accordingly, in a case where the cross section of the target vessel Vt is imaged, only the target vessel Vt can be imaged and extracted by data-converting the picture elements corresponding to the CT values corresponding to the materials (blood, vessel wall, contrast medium, etc.) constituting the vessel. However, in a case where a heart or other vessels are close to the target vessel, the materials constituting those are almost equal to the materials of the target vessel Vt. Therefore, differences in the CT values are small. Thus, the image obtained by data-converting such an orthogonal cross sectional region results in that the cross section of the target vessel Vt and the cross sections of the close heart HT and vessel Vx are combined, as shown in FIGS. 16A and 16B. That is, the cross section and center of the target vessel Vt can not be recognized.

Figure 17:
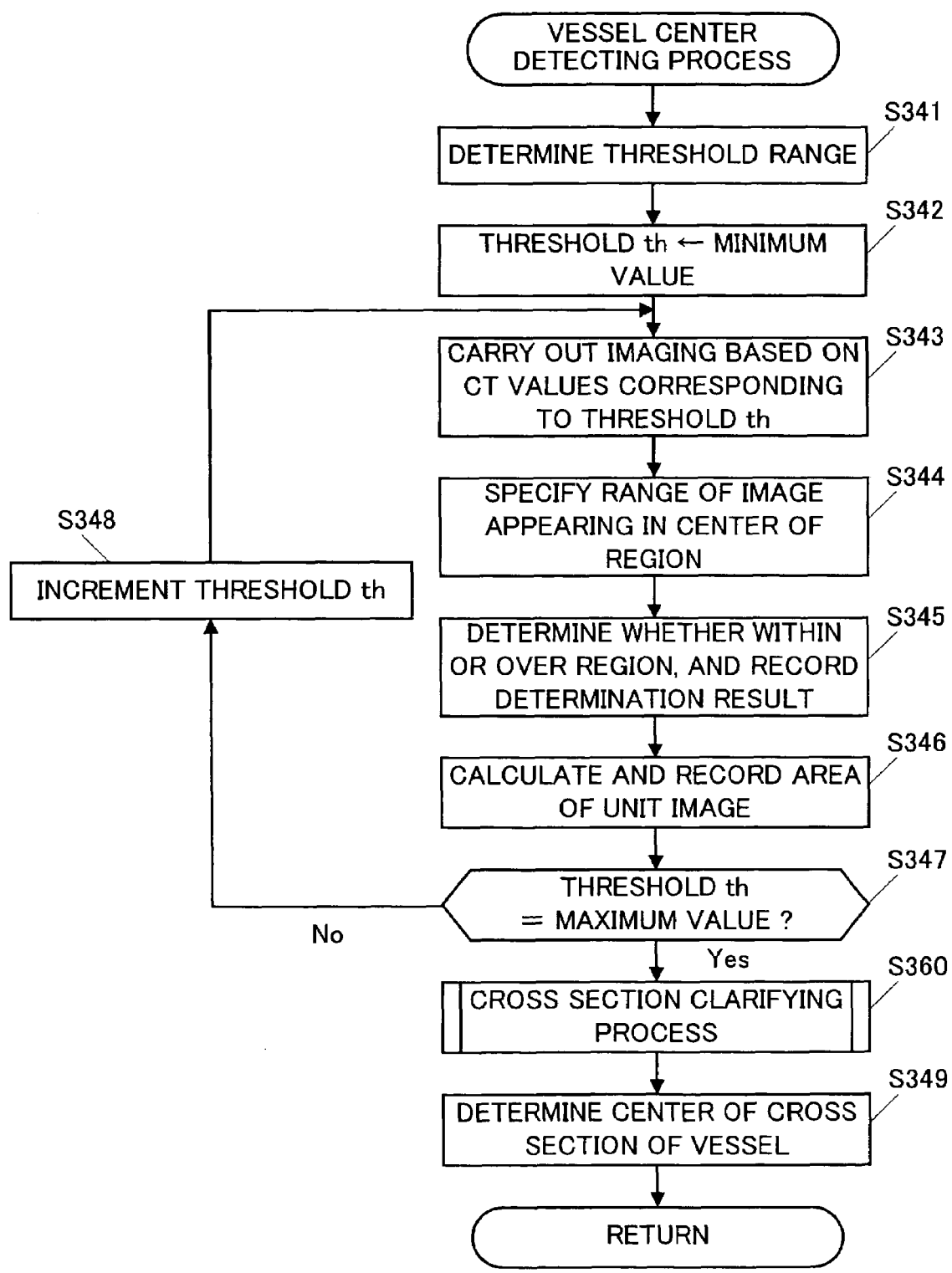
FIG. 17 is a flowchart for explaining a "vessel center detecting process" according to an embodiment of the present invention.

Thus, the control unit 310 performs a "vessel center detecting process" (step S340) for recognizing such slight differences in the CT values to clarify the cross section of the target vessel so as to be identifiable and detect the center of the cross section. This vessel center detecting process will be explained with reference to a flowchart shown in FIG. 17. In this process, the center of the cross section will be detected by changing the range of CT values (hereinafter referred to as "target CT value range") used for data-converting the target area and clarifying the image representing the cross section of the target vessel Vt.

First, the control unit 310 sets the range of "threshold" (hereinafter referred to as "threshold range") used for changing the target CT value range (step S341). In the present embodiment, the target CT value range is changed by changing a threshold indicating the lower limit of the "target CT value range" in the following process. Therefore, the control unit 310 firstly defines a change range of the threshold (minimum threshold th_min to maximum threshold th_max).

The "target CT value range" is a range of CT values which are the target when data-converting the target portion inside a biological body (human body). As described above, materials have their own fixed CT values. In a case where an internal portion of a human body is the target of data-conversion, the target of is an organ, blood (contract medium), a bone, or the like. Accordingly, a range of CT values corresponding to such an organ, etc. is predefined as the target CT value range. Then, since the threshold is changed in the thusly predefined target CT value range, the threshold range shares the same range as the target CT value range.

As described above, the "threshold" according to the present embodiment indicates the lower limit value of the CT value range that is displayed as an image (the target CT value range). That is, in a case where a certain threshold is designated, all the CT values that are equal to or larger than the CT value corresponding to this threshold are the target of displaying as an image. On the other hand, the CT values that are smaller than the CT value corresponding to this threshold are ignored for the target of the displaying (treated as a transparent color). Accordingly, coordinates having characteristic information representing the CT values included in the "target CT value range" in the three-dimensional volume data constituting the concerned region are the target of imaging. For example, in a case where the threshold range (target CT value range) is "0 to 1000" and the threshold is set to "100", coordinates whose characteristic information represents a CT value included in the range of "100 to 1000" are imaged.

Further, in a case where the CT values, which are the X-ray absorption factors, are used for imaging, the differences in the CT values are expressed as differences in brightness. In this case, imaging is carried out by using binary value data where picture elements whose characteristic information represents CT values that are the target of imaging are assigned "1", and picture elements whose characteristic information represents the other CT values are assigned "0". In the present embodiment, it is assumed that CT values representing blood are raised by using a contrast medium at the time of image acquiring. Further, it is assumed that "imaging" means data-conversion with the use of such binary value data. The following explanation will be made by employing as an example, a process performed for the orthogonal cross sectional region SR_ex2 (FIG. 15A) where another vessel Vx exists closely to the target vessel Vt.

Figure 18A:
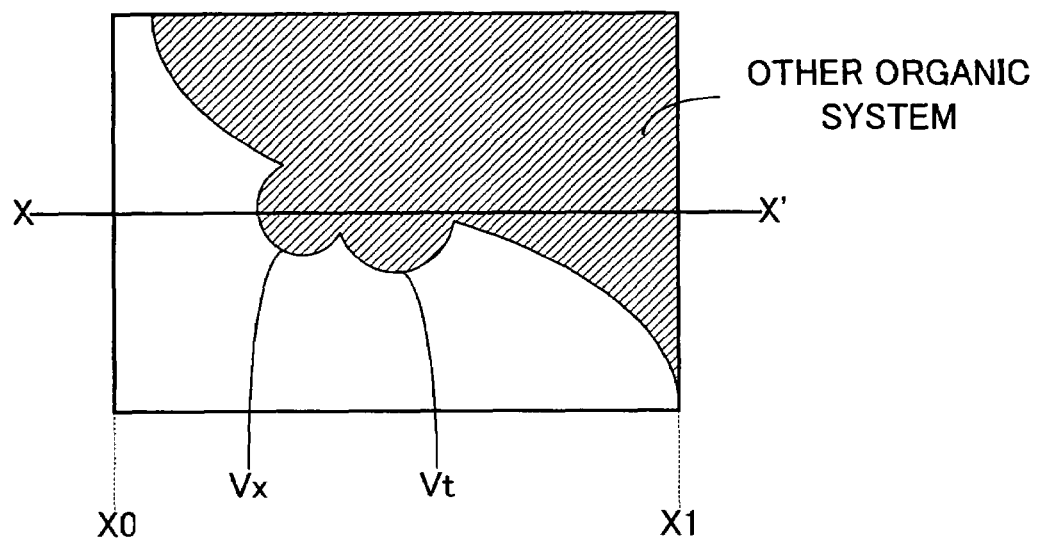
FIG. 18A shows an example of a image when a minimum threshold is set.

First, the control unit 310 sets the minimum threshold th_min set in step S341 as the threshold th (step S342), and images picture elements fit inside the orthogonal cross sectional region SR_ex2 that have, as characteristic information, CT values equal to or larger than the set threshold th (step S343). In a case where the threshold th is the minimum threshold th_min, all the CT values that are within the threshold range (minimum threshold th_min to maximum threshold th_max) are the target of data-conversion. Here, a range of CT values at which an internal portion of a biological body can be imaged is set as a threshold range. Therefore, in a case where the threshold value th is the minimum threshold th_min, by imaging picture elements in the orthogonal cross sectional region SR_ex2 shown in FIG. 15A, not only the cross section of the target vessel Vt and the cross section of the close vessel Vx, but also portions including other tissues around the target vessel Vt and close vessel Vx are imaged, as shown in FIG. 18A.

Figure 18B:
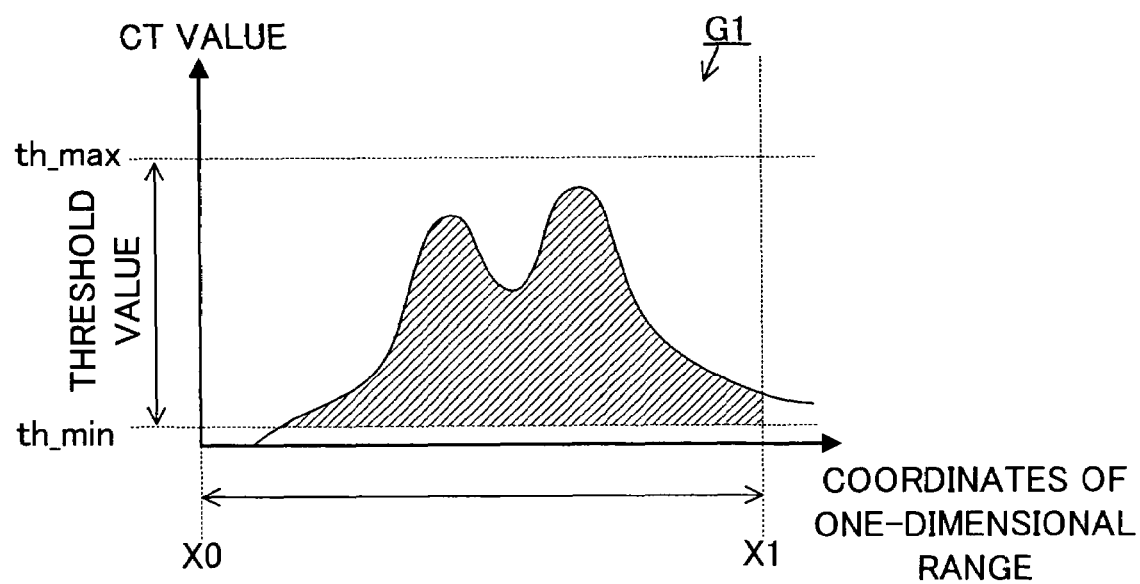
FIG. 18B shows a graph showing picture element distribution in a predetermined one-dimensional range when the minimum threshold is set.

In a one-dimensional range in an X direction that passes through the center of the region (i.e. a region "X0 to X1" on a line "X to X'" in FIG. 18A), the distribution of picture elements having CT values corresponding to the set threshold can be represented as a graph G1 shown in FIG. 18B. In FIG. 18B, the horizontal axis represents the coordinates (X0 to X1) of the one-dimensional range (x-x') in the orthogonal cross sectional region SR_ex2, and the vertical axis represents CT values. Due to the use of a contrast medium, the CT values corresponding to the target vessel Vt and close vessel Vx are relatively high. Accordingly, two peaks appear in the curved graph in the graph G1. That is, these peaks respectively show the positions of the target vessel Vt and close vessel Vx. The area covered with slanted lines in the curved graph shows the distribution of picture elements having CT values equal to or larger than the threshold th (in this case, the minimum threshold th_min). Hereinafter, the graph G1 will be timely referred to, for explaining the relationship between the threshold to be changed in the following process and picture elements which becomes the target at that time.

Next, the control unit 310 specifies a range of the image that appears in the center position of the orthogonal cross sectional region SR_ex2 in the image obtained in step S343 (step S344). In the present embodiment, data-conversion is done based on binary value data, as described above. Due to this, the area of picture elements having CT values corresponding to the set threshold appears clearly as shown in FIG. 18A (the slanted line portion in FIG. 18A).

Figure 19A:
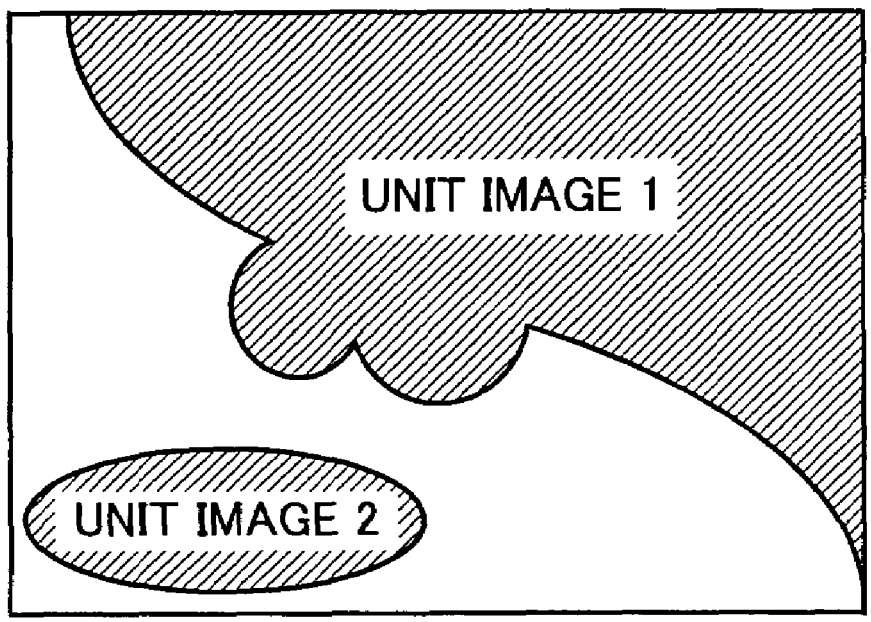
FIG. 19A is a diagram for explaining a term "unit image"

In this case, some orthogonal cross sectional regions may have a plurality of areas containing the picture elements that have CT values equal to or larger than the set threshold, as shown in FIG. 19A. In the present embodiment, an area including picture elements enclosed by the same outline is recognized (determined) by such a method as "Flood Fill" or the like, and treated as one unit (hereinafter referred to as "unit image"). In the example shown in FIG. 19A, two unit images, namely "unit image 1" and "unit image 2" appear.

Figure 19B:
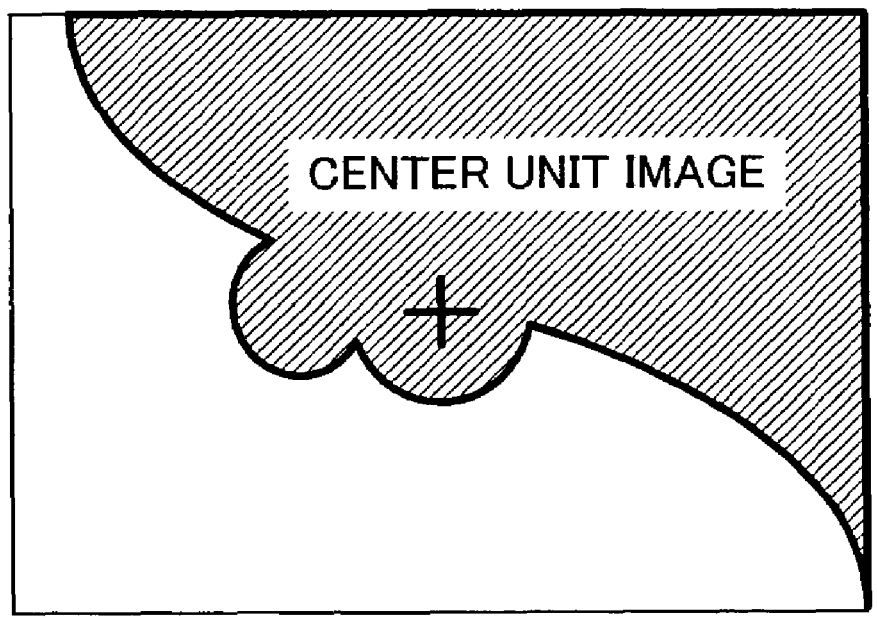
FIG. 19B is a diagram for explaining terms "center unit image" and "range of unit image"

Accordingly, the control unit 310 specifies the range of the unit image that appears in the center position of the orthogonal cross sectional region SR_ex2 in step S344. Here, the "range" corresponds to the outline of the unit image. That is, as shown in FIG. 19B, the control unit 310 specifies the outline of the unit image that includes the center of the orthogonal cross sectional region SR_ex2 (the center is indicated by "+" in FIG. 19B) (a unit image including the center will hereinafter be referred to as "center unit image"). In FIG. 19B, a line segment that is indicated by a bold line is specified as the range (outline) of the center unit image.

The control unit 310 determines whether the range of the center unit image specified in step S344 is fit inside the orthogonal cross sectional region SR_ex2 or not (step S345). In other words, the control unit 310 determines whether or not the range of the center unit image extends beyond the orthogonal cross sectional region SR_ex2. The control unit 310 determines whether the outline specified in step S344 contacts any side of the orthogonal cross sectional region SR_ex2. When it contacts, the control unit 310 determines that the center unit image extends beyond the orthogonal cross sectional region SR_ex2. In case of FIG. 19B, some parts of the outline of the center unit image contact the upper side and right side of the orthogonal cross sectional region SR_ex2. Accordingly, it is determined that the center unit image is not fit inside the orthogonal cross sectional region SR_ex2.

The control unit 310 associates the determination result with the threshold at this time, and records them as "threshold attribute information" in a predetermined storage unit (for example, the work area, the image storage unit 360, or the like) (step S345).

Next, the control unit 310 obtains the area of the center unit imaged specified in step S344. The control unit 310 associates the area value with the threshold at this time, and records them as "threshold attribute information" in a predetermined storage unit (step S346).

Afterwards, the control unit 310 sequentially changes the threshold th until it becomes the maximum threshold th_max, and performs the procedures of steps S343 to S346 at each threshold (step S346: No, S348). That is, the control unit 310 increments the threshold th from the minimum threshold th_min to the maximum threshold th_max, and performs (1) data-conversion, (2) specifying of the center unit image, (3) determining of the range of the center unit image and recording of the determination result, and (4) calculating and recording of the area of the center unit image at each threshold. Due to this, the threshold attribute information recorded in steps S345 and 346 are stored in the predetermined storage unit as a "threshold attribute table" shown in FIG. 20. The incrementing rate for the threshold th (i.e. the lower limit value of the CT value range that is the target of imaging) is arbitrary, and is therefore arbitrarily set in accordance with process capacity of the image processing apparatus 300 and a desired accuracy. In the present embodiment, the threshold th is incremented by "+1" for easier understanding.

Figure 21:
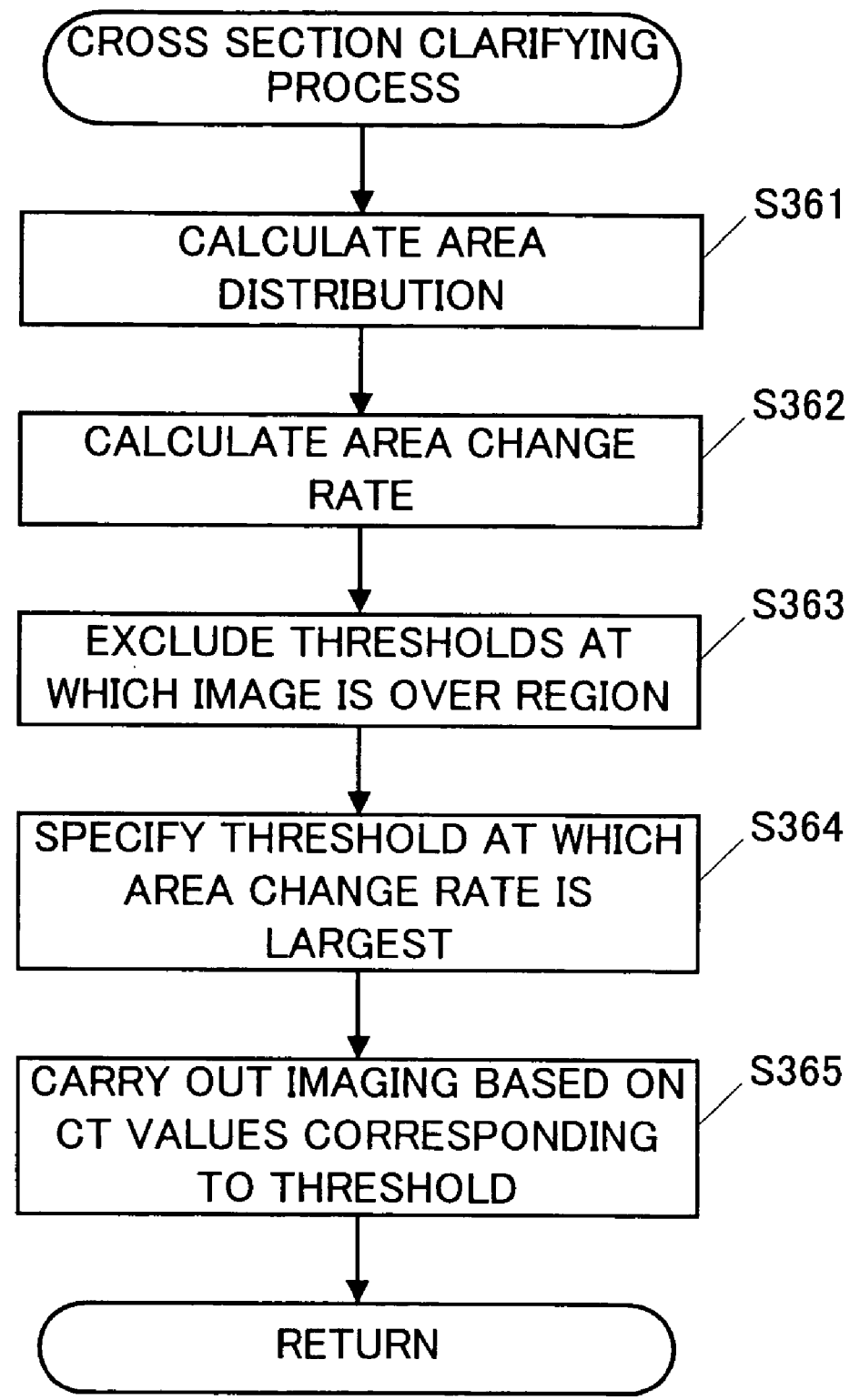
FIG. 21 is a flowchart for explaining a "cross section clarifying process" according to an embodiment of the present invention.

The control unit 310 detects the center of the target vessel Vt in the orthogonal cross sectional region SR_ex2 by using the "threshold attribute information". For this detection, the control unit 310 performs a "cross section clarifying process" (step S360) for clarifying the cross section of the target vessel Vt in the image based on the changes of the areas (image attribute). This "cross section clarifying process" will be explained with reference to a flowchart shown in FIG. 21.

Figure 22:
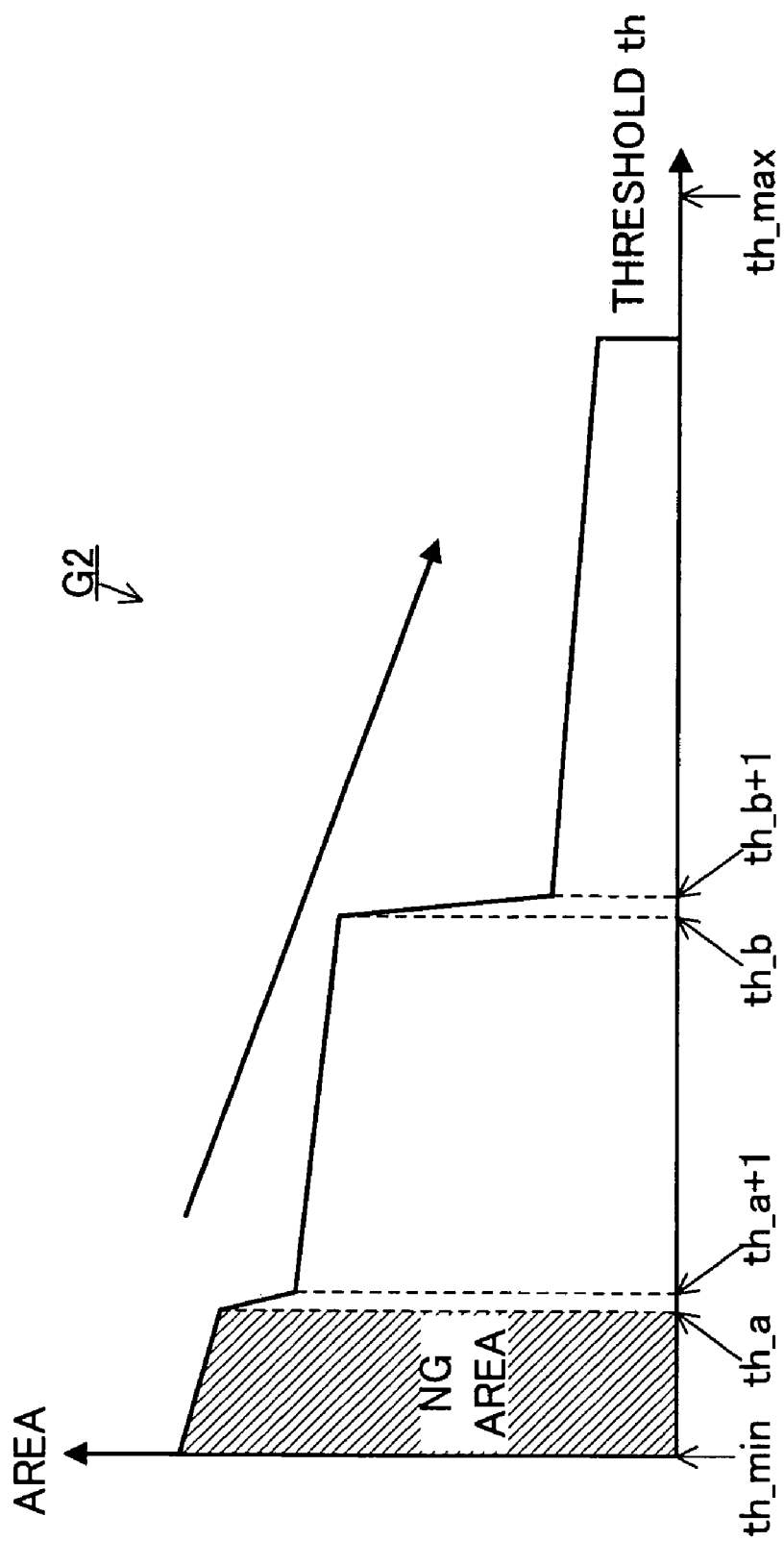
FIG. 22 is a graph showing changes in the area of a center unit image, which is detected in the cross section clarifying process shown in FIG. 21.

First, the control unit 310 acquires "area values" from the threshold attribute table shown in FIG. 20, and obtains a distribution of areas of the center unit image in the set threshold range (step S361). In this example, the control unit 310 can obtain a graph G2 representing an area distribution shown in FIG. 22, by plotting each area value. In the graph G2, the horizontal axis represents the threshold th (minimum threshold th_min to maximum threshold th_max), and the vertical axis represents the area of the center unit image. As shown in FIG. 22, as the threshold th changes from the minimum threshold th_min to the maximum threshold_max, the area value of the center unit image decreases. This is because the imaging target CT value range is narrowed in accordance with the change of the threshold th, and thereby the area of the region to be imaged is reduced.

The control unit 310 obtains area change rates of the center unit image (step S362). In this step, the control unit 310 can obtain the area change rates by defining the area distribution obtained in step S361 as a piecewise function, and differentiating this piecewise function.

Next, the control unit 310 refers to the threshold attribute table, and excludes the thresholds at which the center unit image is not fit inside the orthogonal cross sectional region SR_ex2 (step S363). This exclusion is done because in a case where the cross section of the target vessel has a generally circular shape and is positioned in the center of the orthogonal cross sectional region SR, the image of the cross section whose outline is clarified (or clarified image) can not extend beyond the orthogonal cross sectional region.

During the process of incrementing the threshold th (that is, the process of narrowing the target CT value range), there are some cases where the area of the center unit image sharply decreases, as shown by the graph G2 in FIG. 22. In the example of the graph G2, the area sharply decreases when the threshold changes from th_a to th_a+1, and from th_b to th_b+1. The change of the threshold th "from th_a to th_a+1" is when the center unit image that has been extending beyond the region so far comes fit inside the region along with the decrease of the area. The change of the threshold th "from th_b to th_b+1" is when the center unit image is clarified such that it represents the cross section of the target vessel Vt. The former, that is, an example of the case the center unit image is fit inside the region along with the decrease of the area will be explained by employing FIG. 23 and FIG. 24, and the latter, that is, an example of the case the center unit image is clarified will be explained by employing FIG. 25 and FIG. 26.

Figure 23A:
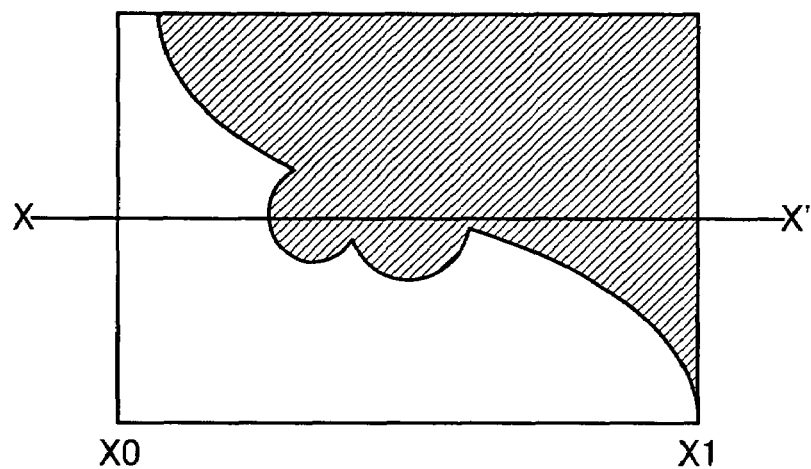
FIG. 23A shows an example of a case where a center unit image extends beyond an orthogonal cross sectional region.
Figure 23B:
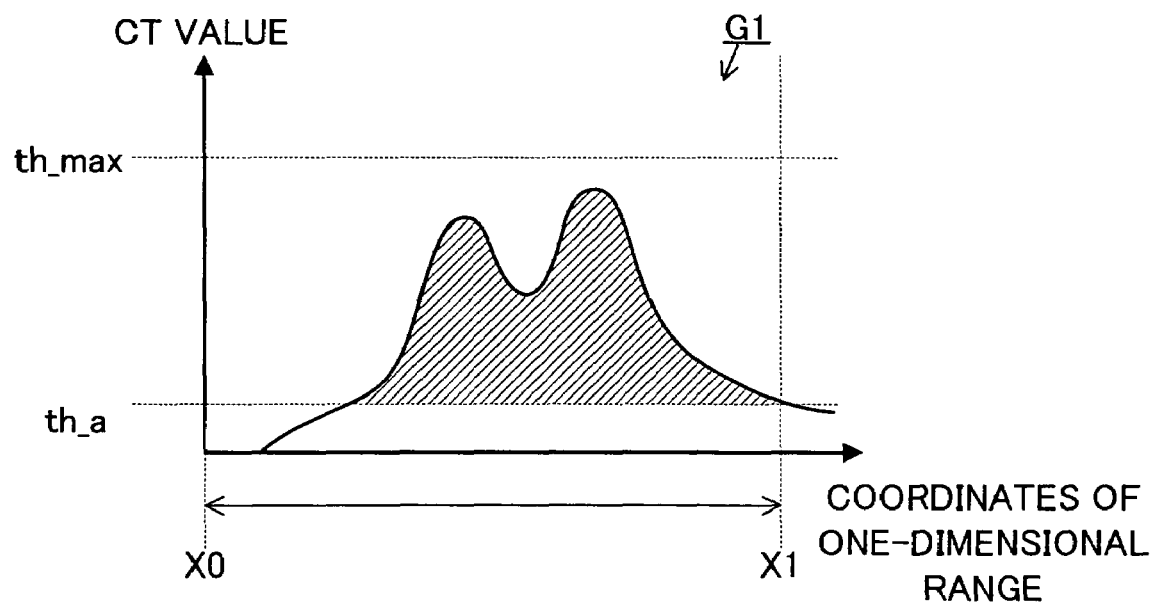
FIG. 23B is a graph showing relationship between threshold and picture element distribution in this case.
Figure 24A:
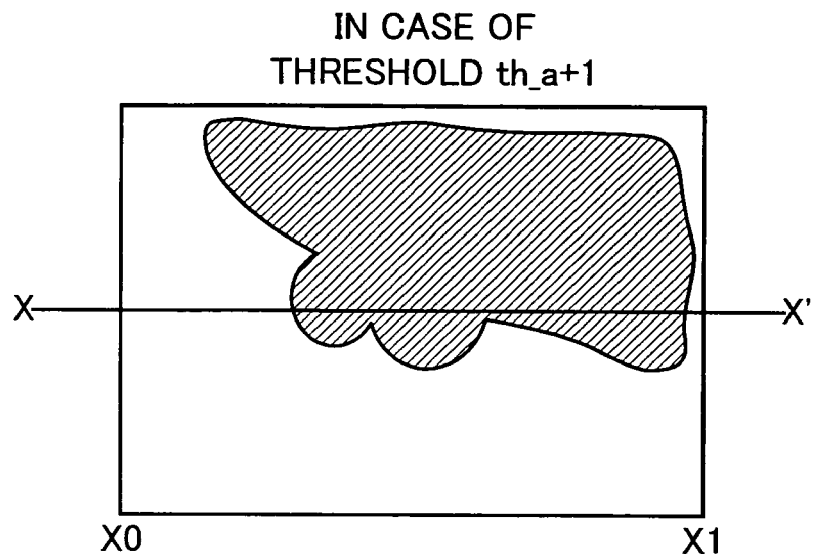
FIG. 24A shows a case where a center unit image is fit inside an orthogonal cross sectional region.
Figure 24B:
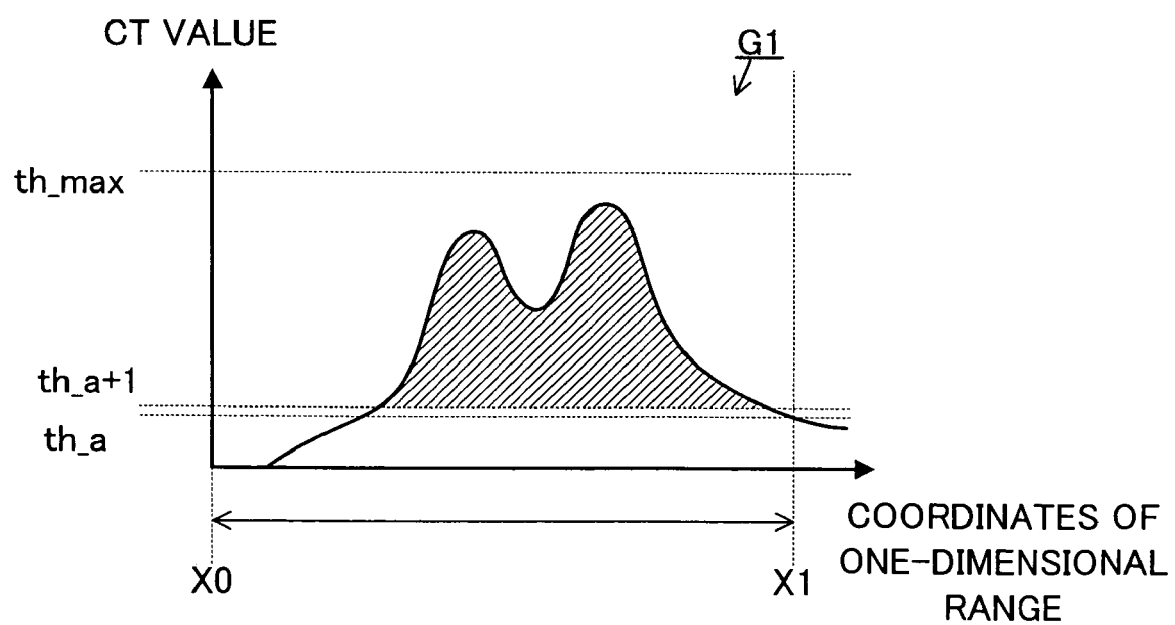
FIG. 24B is a graph showing relationship between threshold and picture element distribution in this case.

FIG. 23A shows an example of an image obtained when the threshold th is th_a. FIG. 23B shows a graph G1 representing picture element distribution in a range (X0 to X1) of a one-dimensional region (x-x') shown in FIG. 23A in case of threshold th_a. FIG. 24A shows an image obtained when the threshold th is th_a+1. FIG. 24B shows a graph G1 representing picture element distribution in a range (X0 to X1) of a one-dimensional region (x-x') shown in FIG. 24A in case of threshold th_a+1.

As shown in FIG. 23A, the outline of the center unit image contacts the sides of the orthogonal cross sectional region at the time of threshold th_a. Further, as shown in FIG. 23B, the picture elements whose CT value range is equal to or larger than the threshold (slanted line area) at the time of threshold th_a reach the position X1 which is at the end of the one-dimensional range (x-x'). Then, as shown in FIG. 24 B, when the threshold th is changed from th_a to th_a+1, the picture elements whose CT value range is equal to or larger than the threshold becomes off from the position X1 at the end of the one-dimensional range (x-x'). That is, as shown in FIG. 24A, the center unit image that has been contacting the right side and upper side of the orthogonal cross sectional region becomes fit inside the region. At this time, a clearance is produced between the outline of the center unit image and the sides of the orthogonal cross sectional region. Due to this, the area of the center unit image sharply decreases, showing such a change as shown by the graph G2 (FIG. 22).

Figure 25A:
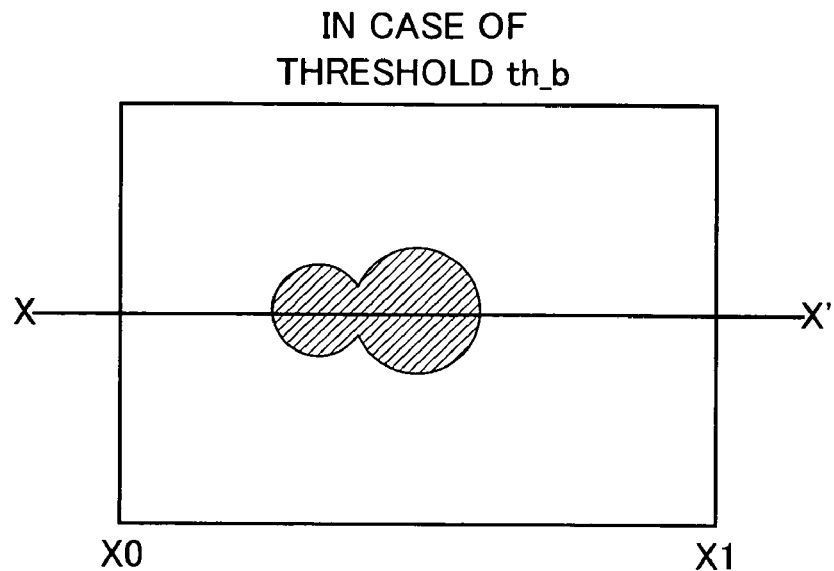
FIG. 25A shows a case where a center unit image includes cross sections of both of a target vessel and another vessel.
Figure 25B:
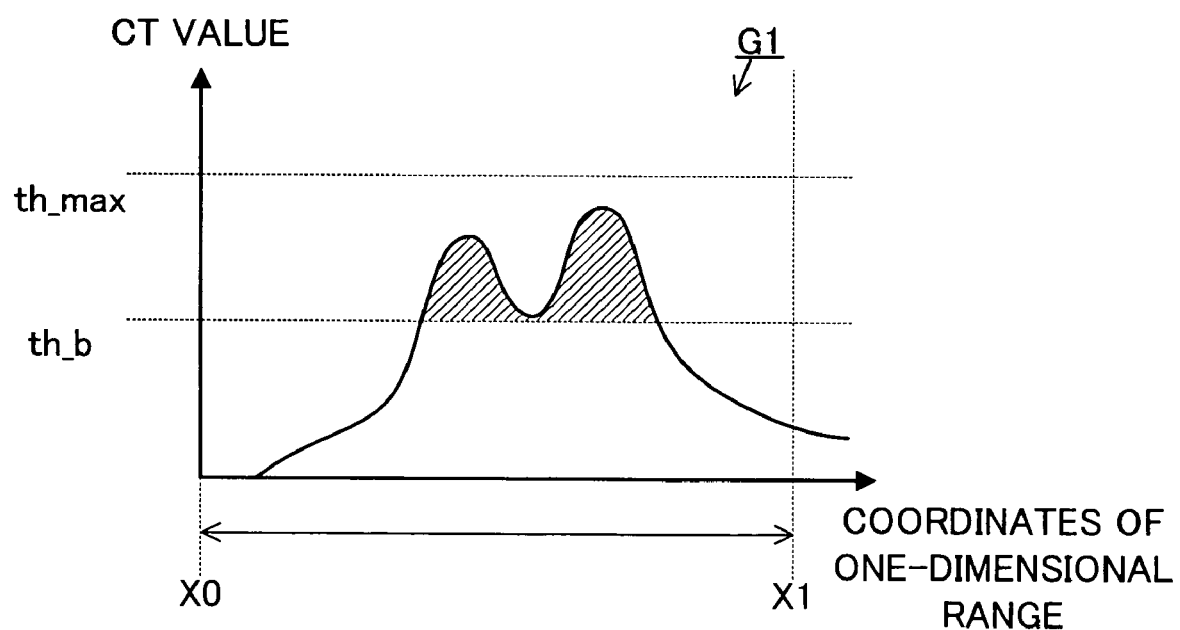
FIG. 25B is a graph showing relationship between threshold and picture element distribution in this case.
Figure 26A:
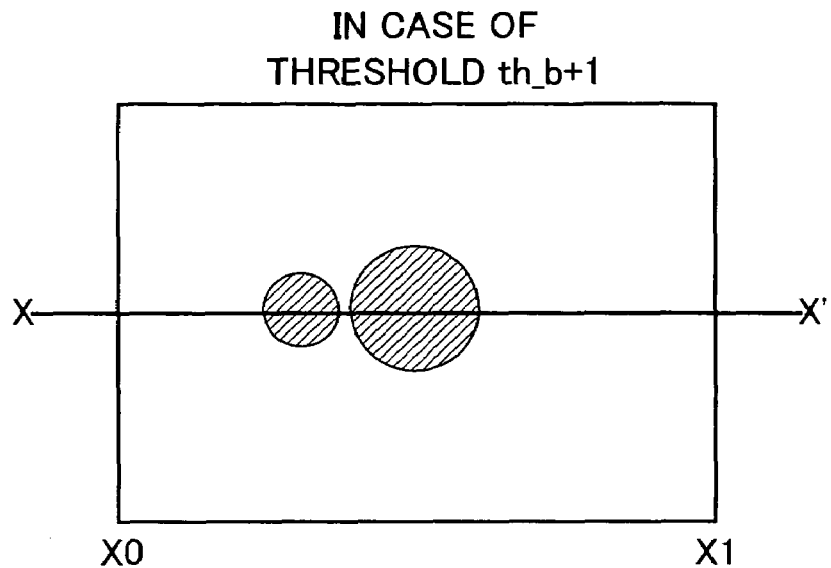
FIG. 26A shows an example of a center unit image when a cross section of a target vessel is clarified.
Figure 26B:
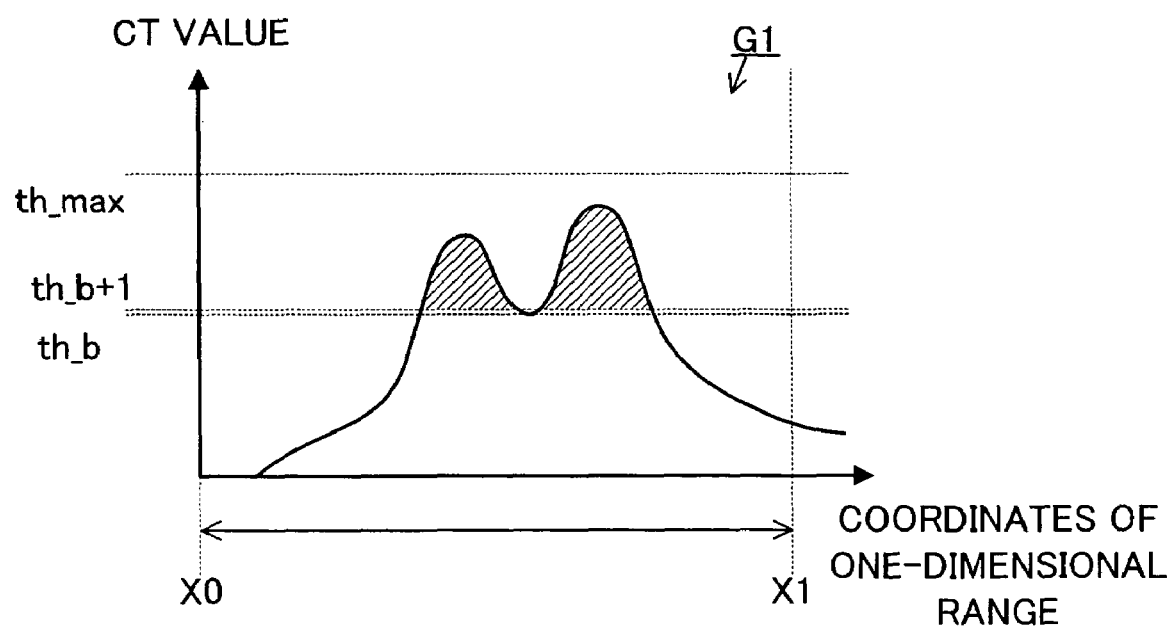
FIG. 26B is a graph showing relationship between threshold and picture element distribution in this case.

On the other hand, FIG. 25A shows an image obtained in case of threshold th being th_b. FIG. 25B shows a graph G1 representing the picture elements which are in a range of CT values is equal to or larger than the threshold in a range (X0 to X1) of a one-dimensional region (x-x') in case of threshold th_b. FIG. 26A shows an image obtained in case of threshold th being th_b+1. FIG. 26B shows a graph G1 representing picture element distribution in a range (X0 to X1) of a one-dimensional region (x-x') in case of threshold th being th_b+1.

As shown in FIG. 25A, at the time of threshold th is th_b, the center unit image is a combined image of both the cross sections of the target vessel Vt and close vessel Vx. Further, as shown in FIG. 25B, the threshold th_b corresponds to the height of the valley between two peaks appearing in the curved graph. That is, the graph G1 shows a picture element distribution including both of the two peaks. Then, as shown in FIG. 26B, when the threshold th is changed from th_b to th_b+1, the picture element distribution is divided into two areas which contain the respective peaks. That is, as shown in FIG. 26A, the center unit image that has been showing both the cross sections of the target vessel Vt and close vessel Vx integrally is divided into two parts. One part is the center unit image showing the cross section of the target vessel Vt, and the other is a unit image showing the cross section of the close vessel Vx. That is, the cross section of the target vessel Vt is clarified. Since the control unit 310 detects the area change of the center unit image, the area of the unit image representing the vessel Vx is subtracted from the area of the center unit image. Thus, a large area decrease appears in the graph G2 (FIG. 22).

As described above, it is possible to determine whether the image of the vessel Vt is clarified or not, by detecting such a sharp decrease in the area of the center unit image. However, in some case, an area change when the center unit image becomes fit inside the region might be larger than an area change when the cross section of the target vessel is clarified, depending on variation of conditions such as the location of the orthogonal cross sectional region and the shape of the center unit image. Therefore, a threshold at which the area change is the largest in the threshold range cannot necessarily be the threshold that clarifies the image of the cross section of the vessel. The control unit 310 therefore excludes thresholds at which the outline of the center unit image extends beyond the orthogonal cross sectional region by referring to the "threshold attribute table" in step S363. Then, the control unit 310 specifies a threshold at which the area change is the largest among thresholds remaining after the exclusion (step S364).

In the example of the graph G2 in FIG. 22, the range of thresholds that are excluded is represented as a non-target area (NG area). A large area change occurs when the threshold th changes from th_a to th_a+1. However, since the threshold th_a is a threshold in the NG area (since the center unit area that is contacting the right side and upper side of the region as shown in FIG. 23A), the threshold th_a is excluded from the detection target. Accordingly, a threshold at which the area change is the largest in the thresholds th_a+1 to th_max, i.e. the threshold th_b+1 is detected. In a case where the area change rates are obtained by the above-described "differentiation of a piecewise function", a threshold at which a minimum differentiation value is obtained can be regarded as a "threshold at which the area change is the largest".

The control unit 310 images picture elements whose CT value is inside a CT value range whose lower limit value is the threshold specified in step S364 and whose upper limit value is the threshold th_max. As a result, the control unit 310 acquires a clear image of the target vessel Vt as shown in FIG. 26A (step S365), and returns to the flow of the "vessel center detecting process" shown in FIG. 17.

When obtaining a center unit image representing the cross section of the target vessel Vt clarified in step S365, the control unit 310 recognizes the shape, size, etc. of the center unit image by a Flood Fill method or the like, and determines the accurate center position of the center unit image (step S349). In step S305, the control unit 310 specifies each orthogonal cross sectional region SR in whose center the cross section of the target vessel Vt is positioned. Therefore, the control unit 310 an accurately obtain the center of the target vessel Vt by obtaining the center of the imaged cross section of the vessel Vt. The orthogonal cross sectional region SR is a region in the three-dimensional volume data. Accordingly, if a specific position in the orthogonal cross sectional region SR is determined, the position can be specified as coordinate of the three-dimensional volume data. That is, the control unit 310 acquires the center position of the cross section of the vessel Vt as coordinate information (x, y, z). When determining the center of the cross section of the target vessel in the orthogonal cross sectional region, the control unit 310 returns to the flow of the "vessel image extracting process" shown in FIG. 8.

The control unit 310 performs the above processes for each of the orthogonal cross sectional regions SR_0 to SR_n (step S306: No). That is, the control unit 310 acquires coordinate information representing the center position of the target vessel in each orthogonal cross sectional region SR which is sequentially specified based on the marching (advancing, progressing) direction settled in the marching (advancing, progressing) direction settling process. In the above explanation for the marching (advancing, progressing) direction settling process, the marching (advancing, progressing) direction is corrected and settled based on the center of the orthogonal cross sectional region SR_0, because the explanation is for the process to be performed for the first round. However, in a case where the center position of the target vessel is determined in the vessel image extracting process, the marching (advancing, progressing) direction should be settled based on the determined center position of the target vessel.

Figure 27:
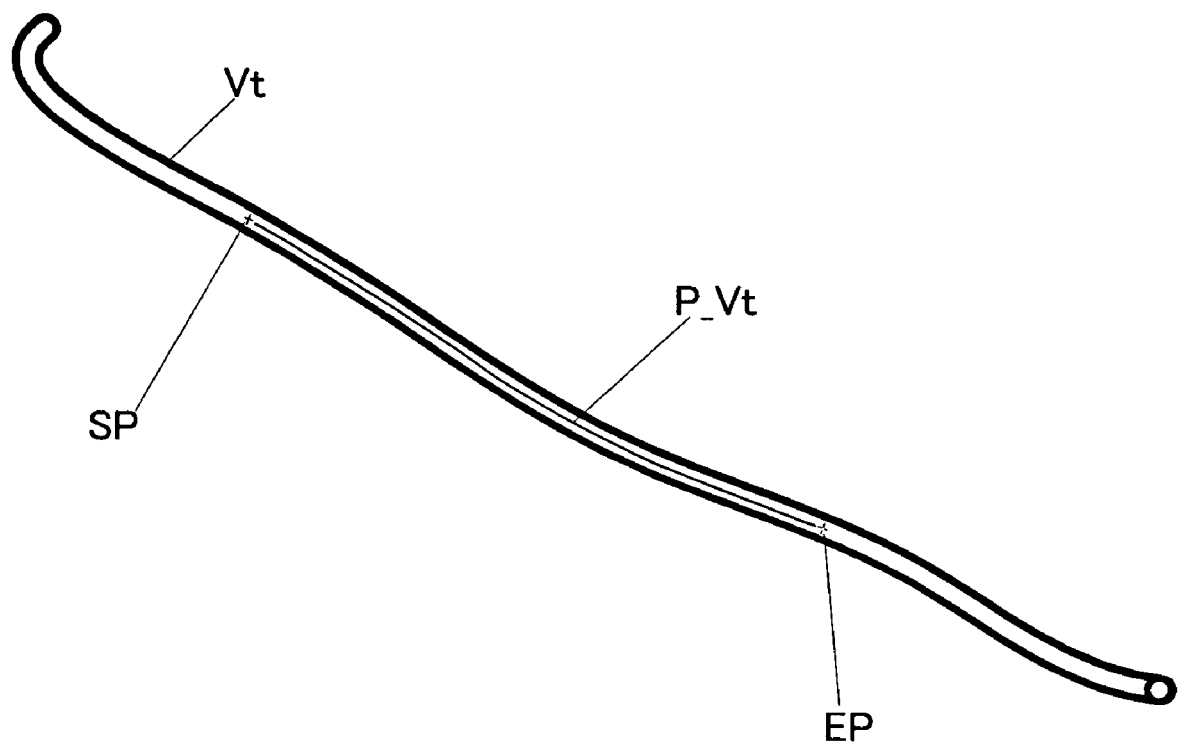
FIG. 27 is a diagram exemplarily showing a three-dimensional path obtained in the cross section clarifying process shown in FIG. 21.

As a result of sequentially performing the above processes, the center of the target vessel in the orthogonal cross sectional region SR_n at the end point EP which is designated in step S302 is determined (step S306: Yes). Due to this, the control unit 310 obtains a three-dimensional path representing the center line of the target vessel Vt in its longitudinal direction, based on the coordinate information representing the center of the target vessel obtained in each orthogonal cross sectional region (step S307). That is, since the center position of the cross section in each orthogonal cross sectional region SR has been obtained as coordinate information, the center line of the target vessel Vt can be specified as a path connecting each obtained center. Accordingly, a path (hereinafter referred to as "path P_Vt") of the center line from the start point SP to the end point EP shown in FIG. 27 can be obtained. The control unit 310 of the image processing apparatus 300 performs generation and display of various medical images, using the obtained path P_Vt (step S500: FIG. 6).

Figure 28:
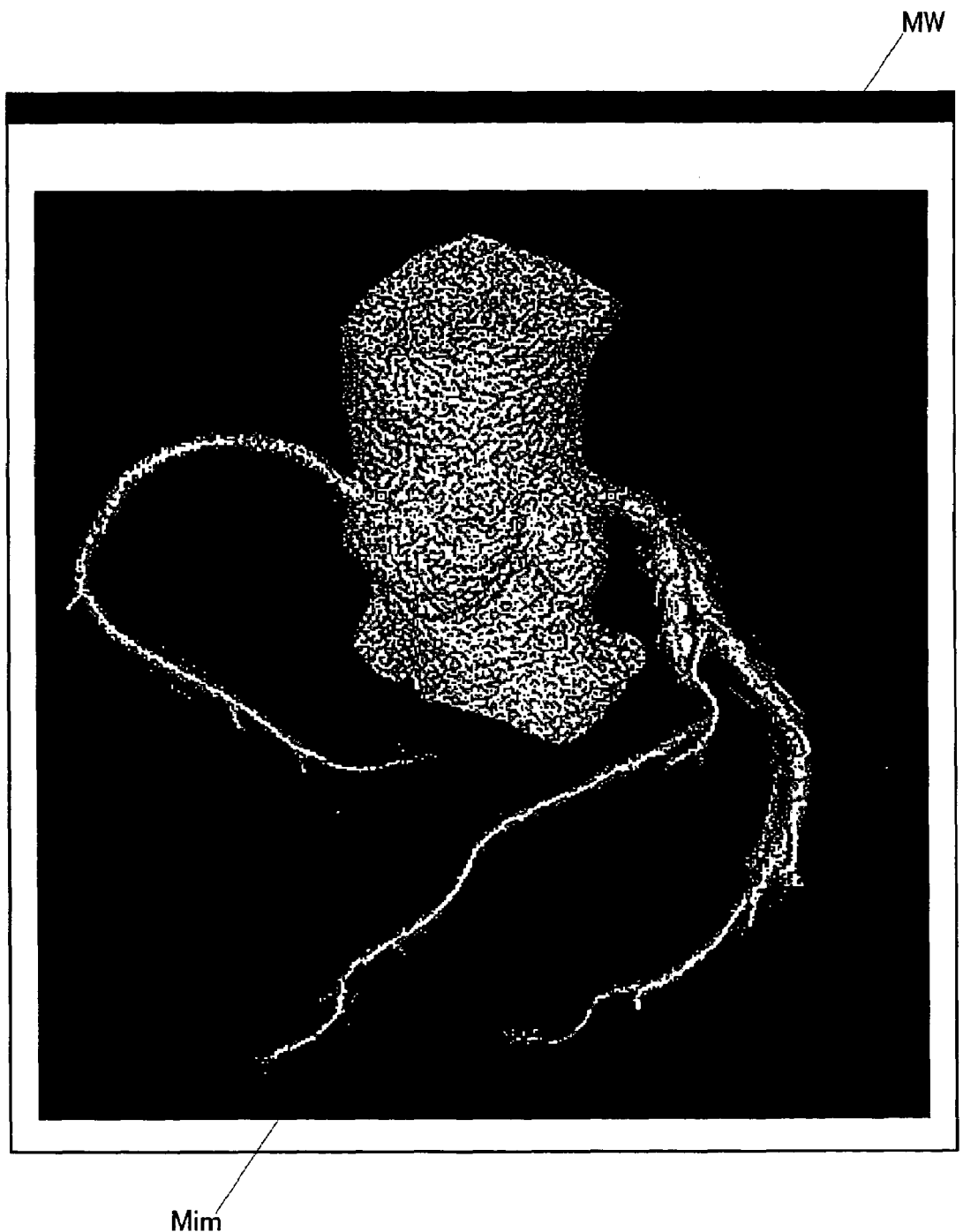
FIG. 28 is a diagram showing an example of a three-dimensional image generated in a "medical image generating/outputting process" shown in FIG. 6.

In the above-described "vessel image extracting process", the path P_Vt, which is vector information representing the center line of the target vessel Vt is obtained. The control unit 310 of the image processing apparatus 300 can generate a three-dimensional image shown in FIG. 28 representing a coronary vessel, by performing an arbitrary three-dimensional image processing (for example, volume rendering, etc.) along the path P_Vt. That is, since the path data representing the center line has been obtained in the above-described "vessel image extracting process", even a portion at which the vessel diameter is narrowed can be three-dimensionally imaged without the vessel being discontinuous. Further, as described above, according to the "vessel image extracting process", even if a heart or another vessel closely exists, the center line of the target vessel can be accurately detected. Therefore, even with a coronary vessel, which has been difficult to three-dimensionally image accurately, such an accurate three-dimensional image as shown in FIG. 28 can be generated.

Further, since the path P_Vt obtained in the above-described "vessel image extracting process" is vector data, various conversion or processing can be applied thereto. That is, the path P_Vt is "three-dimensional path data" derived from three-dimensional coordinate data. However, the control unit 310 of the image processing apparatus 300 can convert it into "two-dimensional path data" by performing predetermined calculations, etc., and can display the vessel as a linear two-dimensional image (tree view). Further, the control unit 310 can associate the path data with a medical image in another format which is generated with the use of the three-dimensional volume data acquired by the modality 100. That is, the control unit 310 can display at the same time a plurality of medical images in different display formats (coordinate systems) concerning the same target, and can mutually associate the positions of the target in the respective images.

Figure 29:
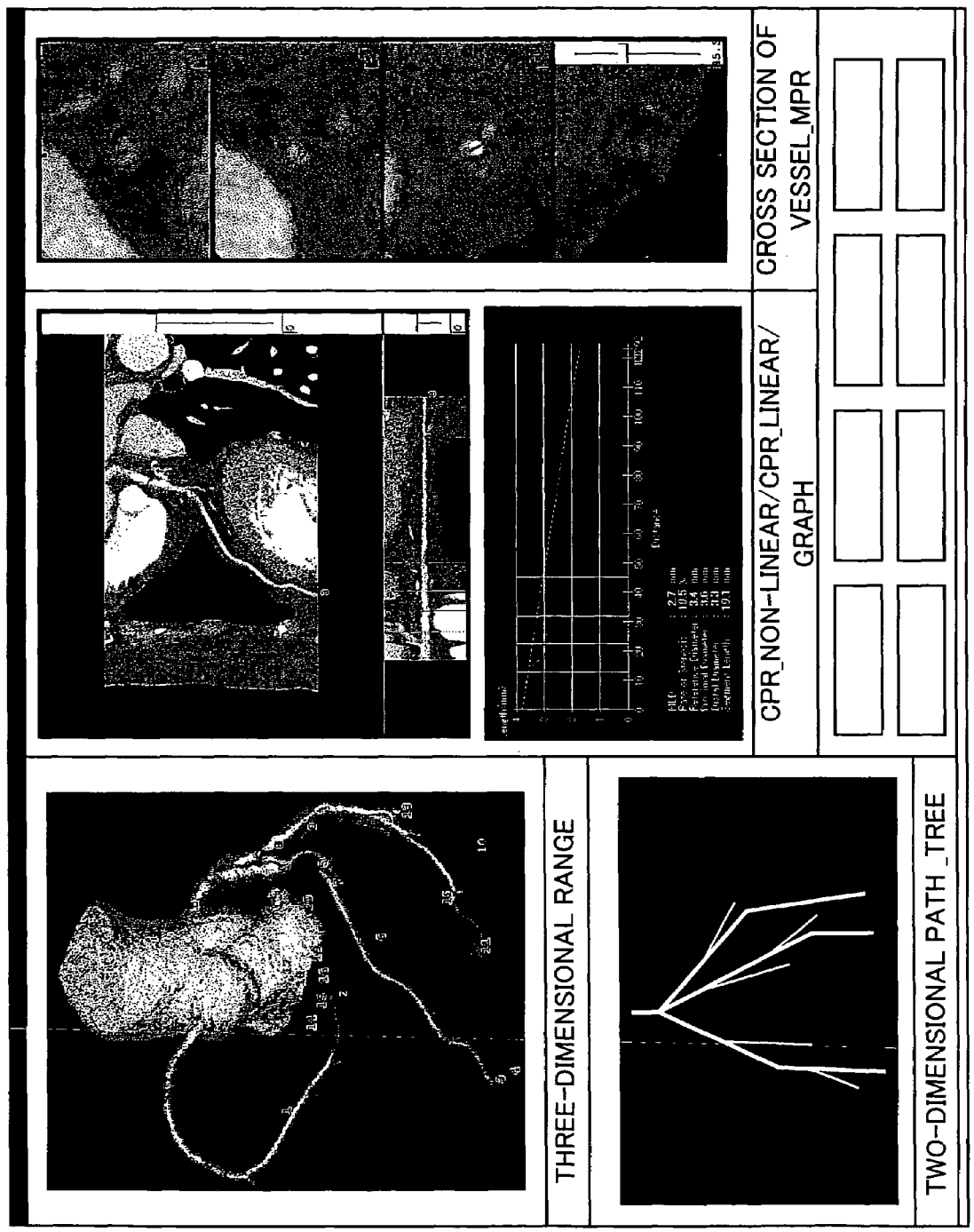
FIG. 29 is a diagram showing a display example of images generated in the "medical image generating/outputting process" shown in FIG. 6.

FIG. 29 shows an example of such image display. The display screen of this example has a plurality of display areas (left, center, right) as shown in FIG. 29. Due to this, medical images in different display formats (coordinate systems) are displayed on the output device 34 (in this case, a display device), under the control of the control unit 310 and output control unit 340. For example, in the left area, a "three-dimensional image" of a heart and a coronary vessel is displayed in the upper section, and "two-dimensional path data" converted from three-dimensional path data is displayed in the lower section. Here, it is assumed that an image representing a three-dimensional path can be displayed while being overlaid on a three-dimensional image. That is, when a vessel displayed as a three-dimensional image is designated by a pointer such as a cursor, the three-dimensional path of this vessel is displayed over the three-dimensional image of the designated vessel.

The conversion of the three-dimensional path data into the two-dimensional path data is for making a tree view by converting the three-dimensional path data into the two-dimensional path data while maintaining the topology (connection/branch relation). In this conversion, for example, a coronary vessel can be represented as a so-called non-cyclic graph having branch points. Accordingly, in a case where a coronary vessel is represented as a two-dimensional path, the coronary vessel can be expressed without the branches intersecting with each other. Further, the three-dimensional path and the two-dimensional path can be easily associated with each other positionally, by calculating the vessel length based on the three-dimensional path data.

Accordingly, if an arbitrary vessel is designated on the three-dimensional image displayed in the upper section of the screen, the three-dimensional path of this vessel is displayed on the three-dimensional image. Meanwhile, in the lower section of the screen, the two-dimensional path representing this vessel is emphatically displayed. That is, by the calculations of the control unit 310, positional information (nodes) in both the images are associated with each other relatively. Due to this, a pointer displayed on the three-dimensional image and a pointer displayed on the two-dimensional path image are linked with each other, making possible such a display that one pointer moves in accordance with the move of the other pointer.

The three-dimensional volume data acquired by the modality 100 may be able to include, for example, various measurement data, other than coordinate information and CT values. Using such measurement data, numerical value data such as bloodstream amount and vessel diameter, etc. can be obtained. These data can not only be associated with the three-dimensional path data, but also associated with two-dimensional path data that is obtained by converting the three-dimensional path data. Accordingly, by the control unit 310 obtaining these measurement data as parameters, the vessel diameter and differences in the bloodstream amounts can be visibly displayed. For example, a portion where the vessel diameter is equal to or less than a predetermined threshold in the two-dimensional path image can be displayed in a color different from the color of other portions.

It is generally said that the probability that an abnormality occurs at a portion where the vessel diameter is narrowed is high. A three-dimensional image has a defect that an abnormality that occurs in a vessel or a portion where the diameter is narrowed is difficult to spot, although it is suitable for grasping the spatial positional relation of a vessel. Thus, the two-dimensional path data in the above-described display format is displayed together with the three-dimensional image. This makes it possible to confirm the abnormality or the portion where the diameter is narrowed on the two-dimensional path image as to in which part of which vessel such abnormality, etc. is located, and to confirm the location in the three-dimensional image, as the actual location.

Further, as shown in FIG. 29, a CPR (Curved-Planer Reconstruction) image or the like representing the target vessel is displayed in the lower and middle sections of the center display area. CPR is for designating an arbitrary curved region in three-dimensional volume data. For example, by designating a curved region along a vessel, a cross section of the vessel in the longitudinal direction can be displayed in one screen. In the example of FIG. 29, an image in a "CPR non-linear mode" is displayed in the upper section, and an image in a "CPR linear mode" is displayed in the lower section. The "non-linear mode" is for data-converting the designated curved region without any special processing. The "linear mode" is for simulatively expanding the designated curved region and displaying the target vessel as a linear image.

The coordinate information of the displayed CPR image can also be associated with three-dimensional path data and two-dimensional path data by calculations of the control unit 310. Accordingly, if a desired vessel is designated from either of the three-dimensional image or the two-dimensional path, a CPR image of the designated vessel is displayed in the center area. If the pointer is moved on the three-dimensional image, the pointer on the CPR image is also moved in response to this. Since various information can be included in the volume data as described above, the control unit 310 generates a graph based on these information and displays the graph in the lower section. Various information regarding a position designated from the above-described three-dimensional image or the like can be shown by this graph. For example, if a plurality of points on a vessel are designated from a CPR image, information such as vessel diameter, constriction degree, etc. regarding the respective designated point is graphed and displayed so that the generated graphs can be compared.

In the right area, an MPR image representing a cross section of a vessel is displayed. The coordinate information of this MPR image is also associated with coordinate information of other types of images by calculations of the control unit 310. Accordingly, if a plurality of points on a vessel are designated from the MPR image, the cross sections of the vessel at the designated points are displayed.

Since positional information of these kinds of displayed images is mutually linked, if any point is designated from any image, a corresponding position is visibly displayed on the other kinds of images. Due to this, a plurality of images in different display formats (coordinate systems) can be displayed in one screen, and can be seen parallely, making it possible to grasp the positional relationship between the images correspondingly. Accordingly, spotting of an abnormal portion can be carried out by using two-dimensional path data or an MPR image, while the operation of the abnormal portion can be carried out by seeing a three-dimensional image to confirm the actual location of the abnormal portion. This contributes to improvement of accuracy of diagnosis and medical treatment.

As explained above, according to the image diagnosis system 1, in generating an image of a tubular tissue such as a vessel, the cross section of the vessel is clarified by changing a threshold in each orthogonal cross sectional region. Therefore, even in a case where, for example, CT values suddenly fluctuate in the middle of a vessel because of a change in the vessel diameter or an abnormal portion, the center line of the vessel can be accurately extracted. Accordingly, a good image with no discontinuation, etc. can be obtained. Further, the center of a cross section is detected by clarifying a cross section of a vessel in each orthogonal cross sectional region. Therefore, even in a case where other organs, etc. having similar CT values closely exist, the center line of the target vessel can be accurately extracted. Furthermore, the center line of the target vessel can be obtained as path data. The obtained path data can be mutually linked with a plurality of medical images in different display formats, and these medical images can be displayed at the same time. Consequently, medical image display that is quite helpful for diagnosis and treatment for a coronary vessel around a heart can be realized.

In the above described explanation, the orthogonal cross sectional region SR_ex1, the orthogonal cross sectional region SR_ex2 and their median points are obtained to obtain the median point of the tubular tissue in each micro-area. However, the method of obtaining the median point is not limited to this. For example, it can be directly obtained by obtaining directly the coordinates of the median point from voxel data.

(Second Process Method)

Next, the vessel image extracting process employing the continuous region specifying method will be explained with reference to a flowchart shown in FIG. 30. In the present process, the image processing apparatus 300 extracts a three-dimensional image of a desired vessel by using acquired image data obtained in the "image acquiring process". In the present embodiment, explanation will be made by employing as an example, a case where the target of extraction is a coronary vessel around a heart.

First, the image processing apparatus 300 obtains process target three-dimensional volume data (acquired image data) from the control terminal 200 via the communication network 10 (step S401).

Next, the control unit 310 displays a two-dimensional image based on the acquired image (three-dimensional volume data) obtained in step S401 on the output device 34 (display device). Then, the control unit 310 receives designation of an extraction start point and extraction end point of a vessel regarded as a target of extraction (hereinafter referred to as "target vessel Vt") (step S402). In this step, an operator such as a doctor, etc. operates the input device 33 and designates the extraction start point and extraction end point on the displayed two-dimensional image.

Figure 31A:
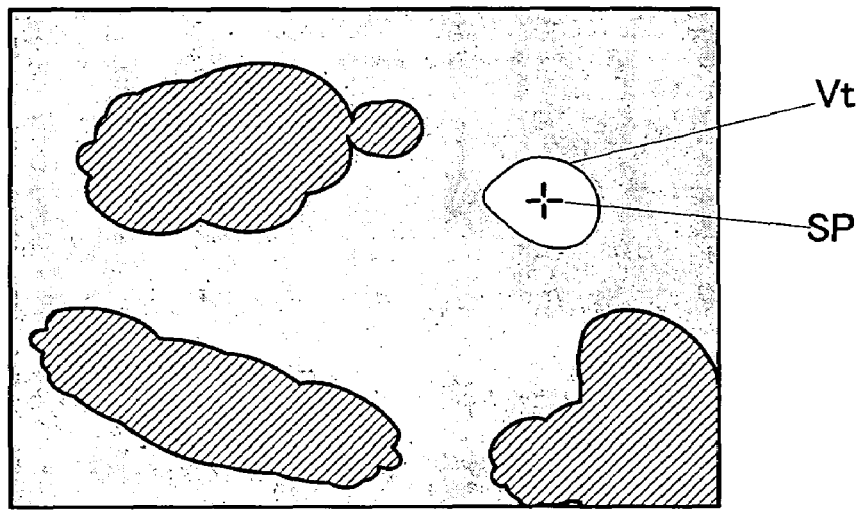
FIG. 31A shows an example of a two-dimensional image displayed for designation of a start point, and FIG. 31B exemplarily shows a positional relationship between a designated start point and end point and a target vessel.
Figure 31B:
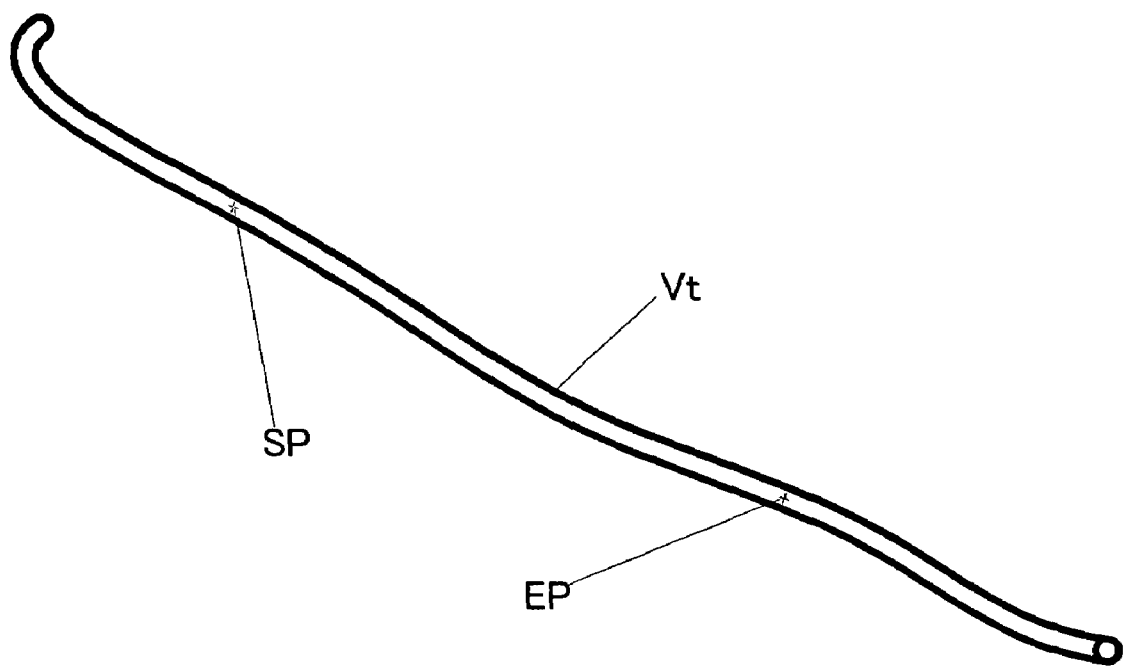
FIG. 31 are diagrams for explaining a process included in the "vessel image extracting process" shown in FIG. 30, where

FIG. 31A shows an example of the two-dimensional image displayed herein. An image representing a cross section of the target vessel Vt, which is acquired by the above-described MPR, etc. is displayed on the output device 34. That is, an image of a cross section of the target vessel Vt is displayed by data-conversion darkness and brightness based on differences in the CT values included in three-dimensional volume data. The image processing apparatus 300 arbitrarily changes the display such that the position or angle of display is changed, by data-converting the three-dimensional volume data corresponding to a position or direction designated by the operator by operating the input device 33. In a case where the target of image acquiring is a vessel, a contrast medium is usually used to raise the CT values of blood. Due to this, as shown in FIG. 31A, the vessel portion is displayed relatively brightly. The operator operates the input device 33, and changes the display screen so that a cross section of the target vessel Vt at the extraction start point will be displayed. The operator designates the center of the displayed cross section (hereinafter the center will be referred to as "start point SP"), by using the input device 33. Likewise, the operator designates the center of a cross section at the extraction end point (the center will hereinafter be referred to as "end point EP").

When the start point SP is designated in step S402, the control unit 310 of the image processing apparatus 300 specifies the three-dimensional coordinates (x,y,z) of the start point SP. When the three-dimensional coordinate of the start point SP are specified, the control unit 310 specifies a three-dimensional region having a cubic shape whose center (median point) is the start point SP (hereinafter the region will be referred to as "three-dimensional region TDR" and the center of the three-dimensional region TDR will be referred to as "center CP") (step S403). In this step, the control unit 310 specifies a three-dimensional region by, for example, combining planer regions designated by the above-described MPR.

When the three-dimensional region TDR is specified, the control unit 310 obtains three-dimensional data for the specified three-dimensional region TDR (step S404). That is, the control unit 310 extracts data corresponding to the three-dimensional region TDR in the three-dimensional volume data obtained in step S401.

Next, the control unit 310 generates a three-dimensional image by using the obtained three-dimensional volume data for the three-dimensional region TDR (step S405). In this step, the control unit 310 generates a three-dimensional image by using the three-dimensional volume data in accordance with Flood Fill method, Region Growing method, etc.

Figure 33:
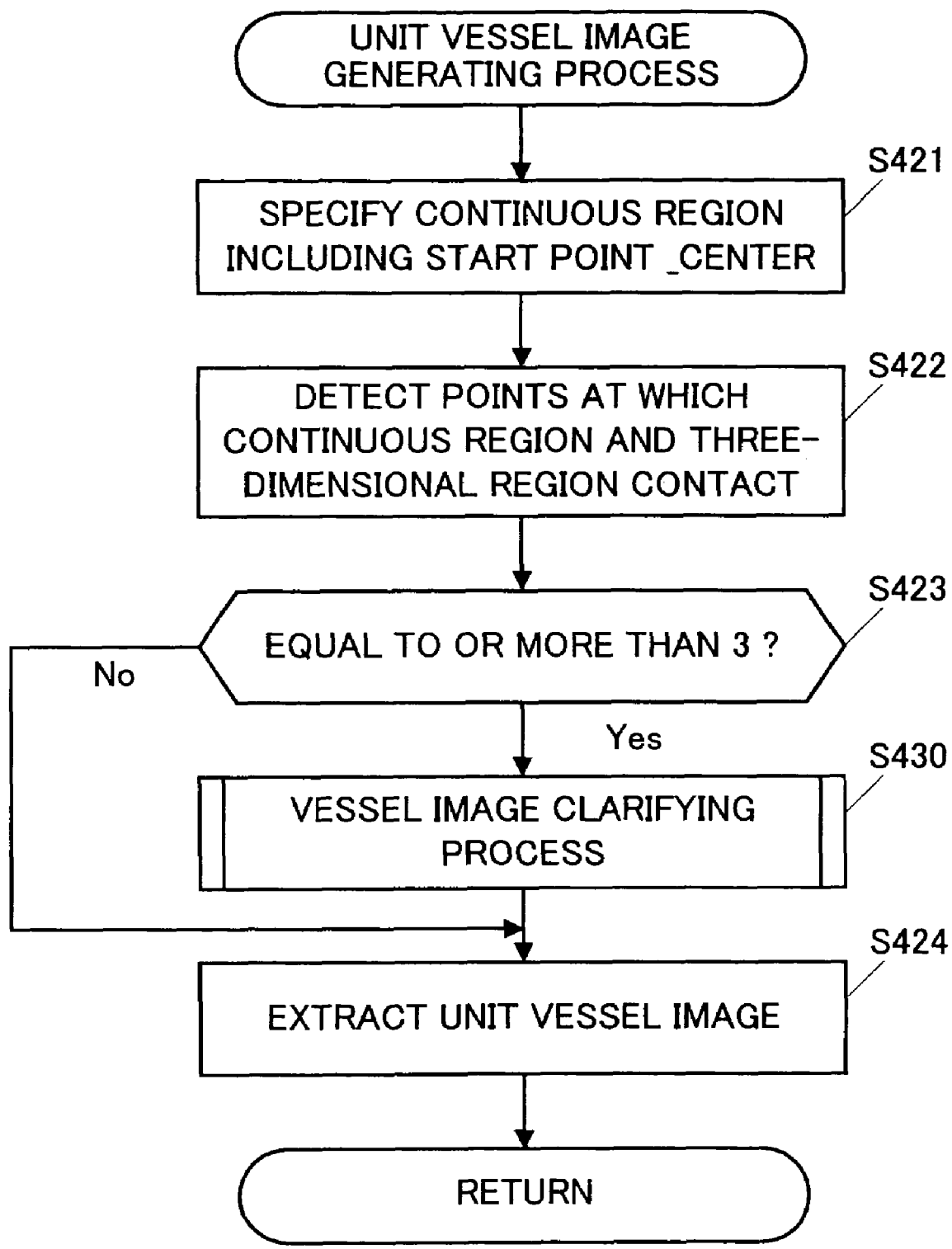
FIG. 33 is a flowchart for explaining a "unit vessel image generating process" performed in the "vessel image extracting process" shown in FIG. 30.

According to the present embodiment, such three-dimensional regions TDR as described above will be sequentially specified along the target vessel Vt (from the start point SP to the end point EP). Then, a three-dimensional vessel image covering a range from the start point SP to the end point EP will be generated by connecting three-dimensional vessel images (hereinafter referred to as "unit vessel image") in the respective three-dimensional regions TDR. Therefore, the control unit 310 performs a "unit vessel image generating process" (step S420) for generating such a "unit vessel image". The "unit vessel image generating process" will be explained with reference to a flowchart shown in FIG. 33.

First, the control unit 310 specifies a continuous region including the start point SP (center CP) from the three-dimensional image generated in step S405 (step S421). A "continuous region" is a closed image having the same outline (limited closed image) which is obtained by, for example, Flood Fill method, or the like. In step S421, the control unit 310 specifies a range of a continuous region within the generated three-dimensional image and including the coordinates of the center CP of the three-dimensional region TDR (hereinafter this continuous region will be referred to as "continuous region CIM").

Next, the control unit 310 specifies positions at which the specified continuous region CIM and a surface of the three-dimensional region TDR (one surface of the cube) contact with each other (step S422). Then, the control unit 310 determines whether the number of such positions is equal to or greater than 3 (step S423). In this step, it is determined whether or not the continuous region CIM is a three-dimensional image representing only the target vessel Vt (such a continuous region CIM will hereinafter be referred to as "unit vessel image IMv").

Figure 32A:
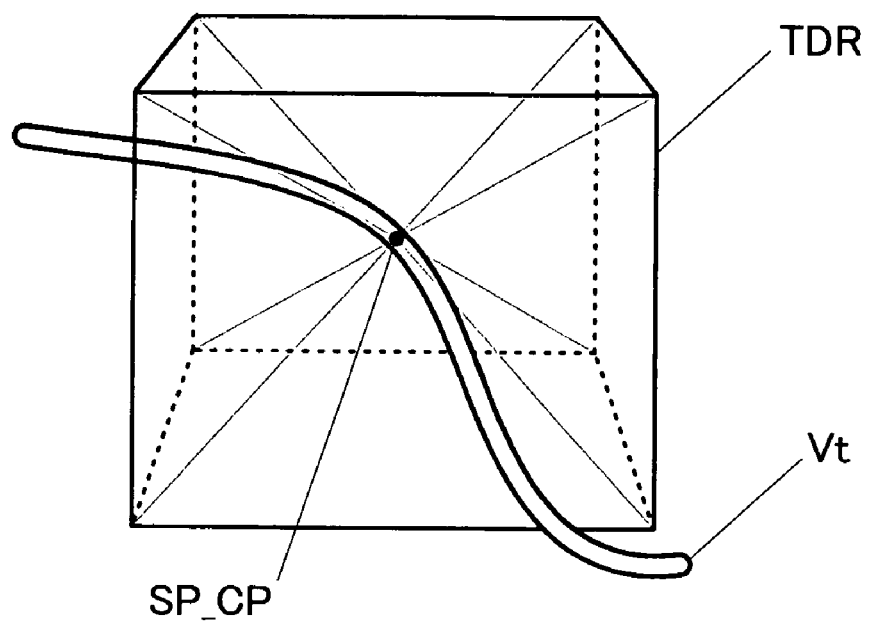
FIG. 32A is a diagram for explaining a positional relationship between a designated start point and a spatial region to be specified.
Figure 32B:
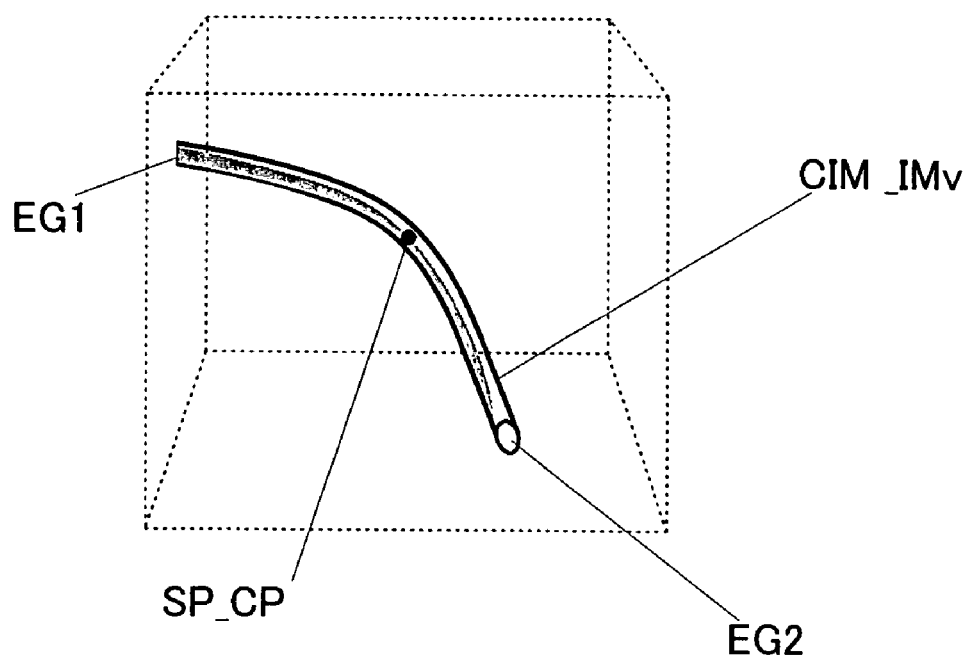
FIG. 32B is a diagram showing an example of a unit vessel image extracted from the specified spatial region.

That is, in a case where only the target vessel Vt exists in the specified three-dimensional region TDR as shown in FIG. 32A, the continuous region CIM obtained by data-converting the three-dimensional region TDR in step 405 should be such a vessel image IMv as shown in FIG. 32B.

Figure 34:
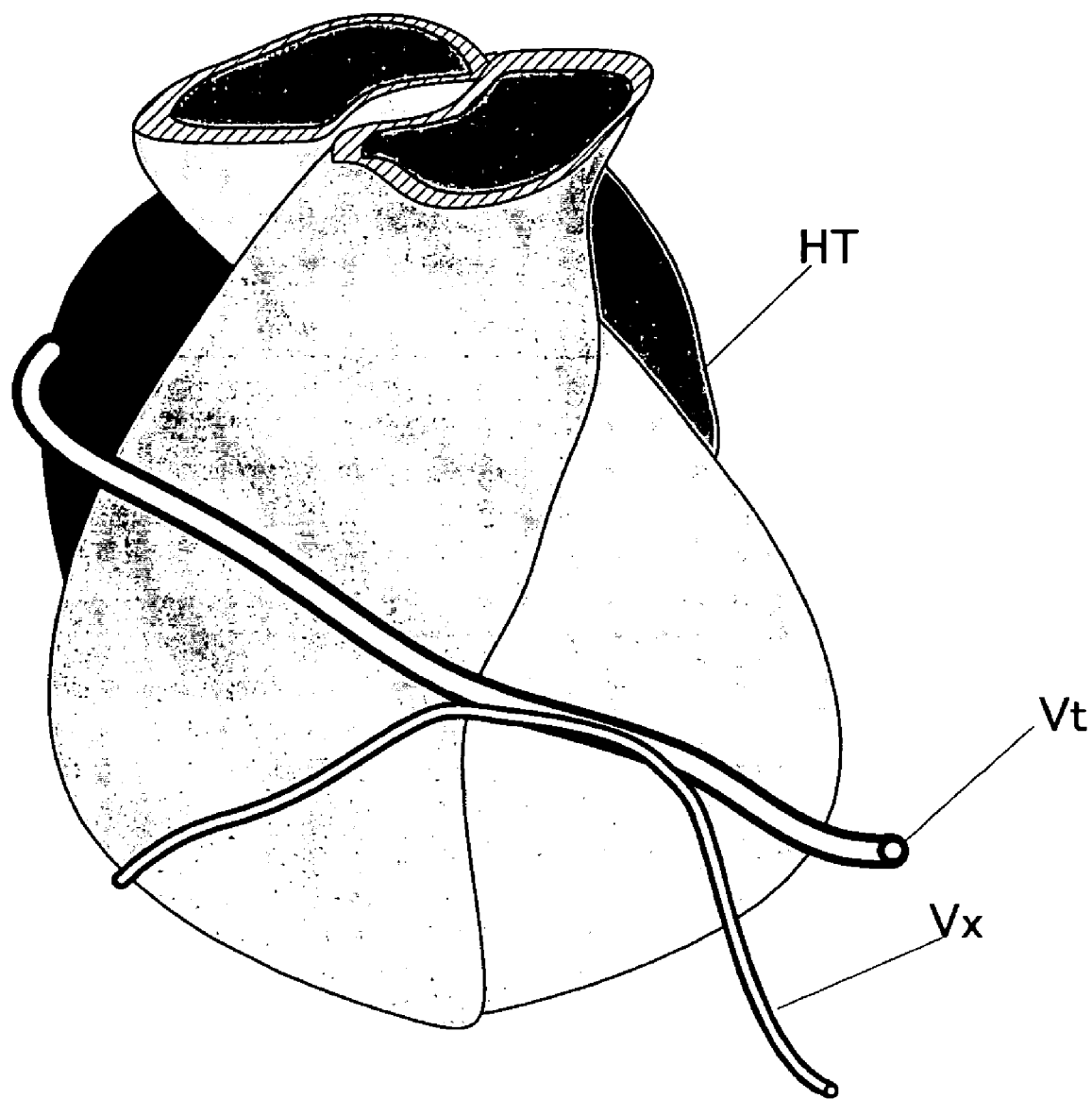
FIG. 34 is a diagram for explaining a positional relationship between a target vessel and a heart and another vessel which are close to the target vessel.
Figure 35A:
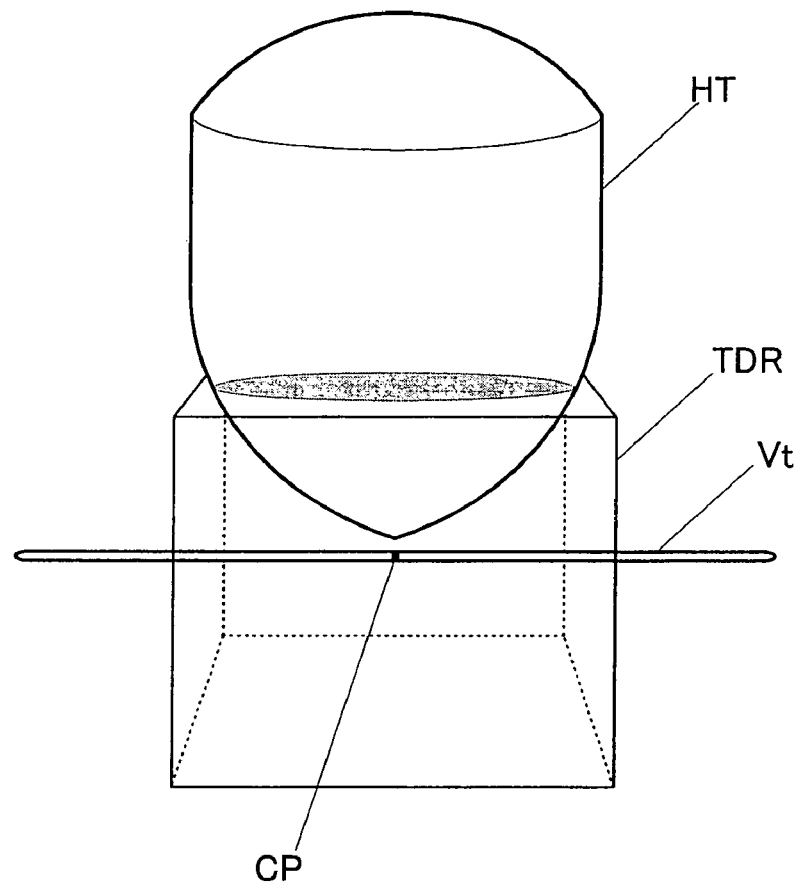
FIG. 35A shows an example of a positional relationship among a target vessel, a heart close to the target vessel, and a spatial region to be specified.

However, in a case where a coronary vessel around a heart is the target, a heart HT or another vessel Vx are close to the target vessel Vt as shown in FIG. 34. If the start point SP on the target vessel Vt is designated in a case where the heart HT is close to the target vessel Vt, a part of the heart HT is included in the three-dimensional region TDR as shown in FIG. 35A.

Figure 35B:
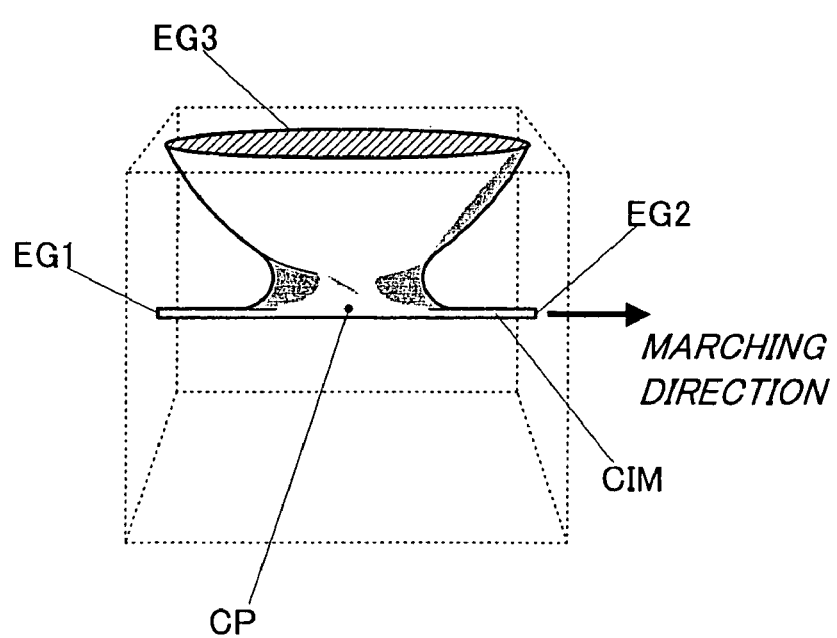
FIG. 35B shows an example of a three-dimensional image when this spatial region is converted.

If such a three-dimensional region TDR is imaged, the generated image will be as shown in FIG. 35B. As described above, according to the present embodiment, data-conversion is carried out by using CT values included in the three-dimensional volume data. CT values represent X-ray absorption factors acquired by the modality 100 (CT scanner), and any materials have their own fixed CT values such as, for example, "water: 0", "air: −1000", etc. Accordingly, in a case where the target vessel Vt is to be imaged, only the target vessel Vt can be imaged by displaying only the picture elements (pixels, voxels) having CT values corresponding to the substances constituting the vessel (blood, vessel wall, contrast medium, etc.). Here, since substances constituting the target vessel Vt and substances constituting the heart HT and another vessel Vx are almost the same, differences in the CT values representing those substances are small. As a result, if the three-dimensional region TDR (FIG. 35A) wherein the heart HT is close to the target vessel Vt is imaged, the generated image will be such that the target vessel Bt and a part of the heart HT are combined, as shown in FIG. 35B. Therefore, the target vessel Vt can not be accurately recognized. Since the start point SP (center CP) is designated upon the target vessel Vt, an image representing the target vessel Vt and heart HT combined together is specified as the continuous region CIM.

Hence, it is necessary to determine whether the continuous region CIM represents only the target vessel Vt, or also includes the heart HT or the like. In step 423, the determination is performed based on the number of contact points shared by the continuous region CIM and the three-dimensional region TDR.

That is, since the target vessel Vt is tubular, there are two points at which the continuous region CIM generated in a case where only the target vessel Vt exists in the three-dimensional region TDR (i.e. such a continuous region CIM is a unit vessel image IMv) and the surface of the three-dimensional region TDR contact each other. Such points will hereinafter be referred to as "contact point EG". In this case, the two points are namely a contact point EG1 and a contact point EG2 shown in FIG. 32B. (Hereinafter, concerning "contact points EG" of a "unit vessel image IMv", a contact point EG in the upstream of a marching (advancing, progressing) direction will be referred to as "EG1" and a contact point EG in the downstream of the marching (advancing, progressing) direction will be referred to as "EG2". The marching (advancing, progressing) direction will be determined based on the start point SP and the end point EP.)

On the other hand, as shown in FIG. 35B, contact points EG at which the continuous region CIM generated in a case where the heart HT or another vessel Vx is close to the target vessel Vt and the three-dimensional region TDR include at least three contact points, namely a contact point EG1, a contact point EG2, and a contact point EG3 (hereinafter, a contact point EG of other than the target vessel Vt will be referred to as "EG3"). In step S423, it is determined whether or not there are three or more contact points EG, in accordance with this principle. Due to this, it is possible to determine whether the continuous region CIM is a three-dimensional image representing only the target vessel Vt or a three-dimensional image including also the heart HT or the like.

In a case where the number of contact points EG is not equal to or greater than 3 (step S423: No), the continuous region CIM is an image representing only the target vessel Vt. Accordingly, the control unit 310 extracts this continuous region CIM as a unit vessel image IMv (step S424).

Figure 36:
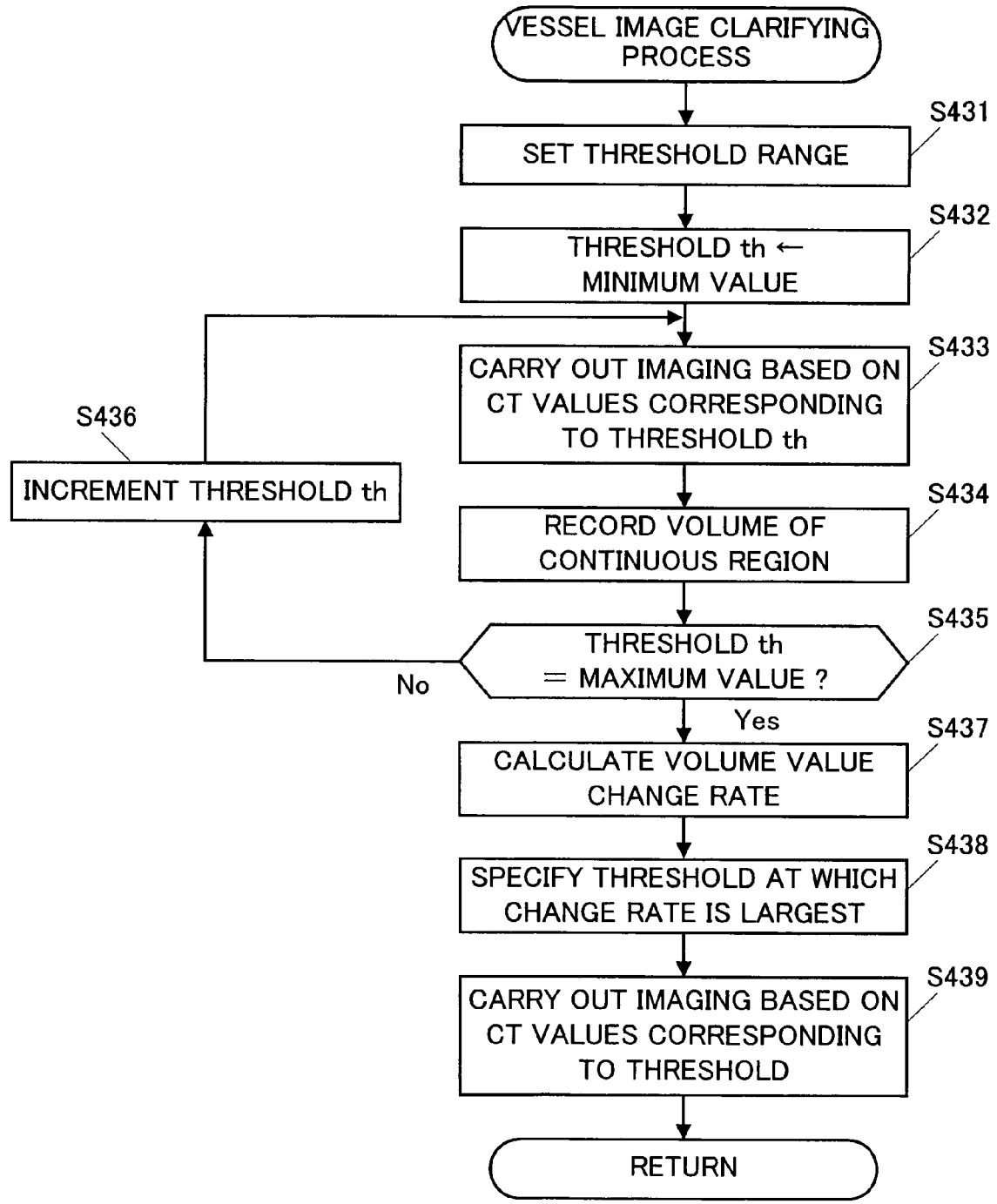
FIG. 36 is a flowchart for explaining a "vessel image clarifying process" performed in the "unit vessel image generating process" shown in FIG. 33.

On the contrary, in a case where the number of contact points EG is equal to or greater than 3 (step S423: Yes), the continuous region CIM includes the heart HT, etc. in addition to the target vessel Vt. Accordingly, in this case, the control unit 310 performs a "vessel image clarifying process" (step S430) for extracting a unit vessel image IMv from the continuous region CIM. This "vessel image clarifying process" will be explained with reference to a flowchart shown in FIG. 36. In this process, an image representing only the target vessel Vt is clarified by changing a range of CT values used for data-converting the three-dimensional region TDR (hereinafter referred to as "target CT value range").

First, the control unit 310 sets a range of "threshold" (hereinafter referred to as "threshold range") used for changing the target CT value range (step S431). In the present embodiment, the target CT value range is changed by changing the threshold representing the lower limit of the "target CT value range". For this purpose, the change range (minimum threshold th_min to maximum threshold th_max) of the threshold is first defined.

The "target CT value range" is a range of CT values which are the target when data-converting the target portion inside a biological body (human body). In the present embodiment, since an inner portion of a human body is the target of data-conversion, the target of data-conversion is, for example, an organ, blood (contrast medium), bone, etc. As described above, each material has its own fixed CT value. Therefore, a range of CT values corresponding to such a target of data-conversion can be defined as the "target CT value range". And since the threshold is changed within the thusly defined "target CT value range", the "threshold range" shares the same range as the "target CT value range".

Further, as described above, the "threshold" according to the present embodiment indicates the lower limit value of the CT value range that is displayed as an image (the target CT value range). That is, in a case where a certain threshold is designated, all the CT values that are equal to or larger than the CT value corresponding to this threshold are the target of displaying as an image. On the other hand, the CT values that are smaller than the CT value corresponding to this threshold are ignored for the target of the displaying (treated as a transparent color). Accordingly, coordinates having characteristic information representing a CT value included in the "target CT value range" in the three-dimensional volume data constituting the concerned three-dimensional region TDR are the target of data-conversion. For example, in a case where the threshold range (target CT value range) is "0 to 1000" and then the threshold is set to "100", coordinates having characteristic information representing a CT value included in the range of "100 to 1000" are imaged.

Further, in a case where data-conversion is carried out based on CT values which are the X-ray absorption factors, differences in the CT values are expressed as differences in the brightness. Picture elements (pixels, voxels) having characteristic information representing an data-converting target CT value are imaged. According to the present embodiment, it is assumed that CT values of blood are raised by using a contrast medium at the time of image acquiring.

First, the control unit 310 sets the minimum threshold th_min set in step S431 as the threshold th (step S432). Then, the control unit 310 images picture elements (pixels, voxels) in the three-dimensional region TDR that have characteristic information representing a CT value which is equal to or larger than the threshold value th (step S433). In a case where the threshold th is the minimum threshold th_min, all the CT values corresponding to the threshold range (minimum threshold th_min) to maximum threshold_max) are the target of data-conversion. Here, a range of CT values at which an internal portion of a biological body can be imaged is set as a threshold range in step S431. Therefore, the result of data-conversion in case of the threshold th being the minimum threshold th_min is such a continuous region CIM as shown in FIG. 35B.

The control unit 310 specifies a boundary of the continuous region CIM obtained by the data-conversion in step S433. Then, the control unit 310 records it in a predetermined storage unit (for example, the work area, the image storage unit 360, etc.) (step S434). For specifying the "boundary of the continuous region", an arbitrary parameter can be used. For example, volume value, surface area or the three-dimensional object represented by the continuous region CIM, coordinate values of the outline of the three-dimensional object, etc. can be used as the parameter. The boundary of the continuous region CIM is specified by any of these parameters or combination of these parameters. In the present embodiment, explanation will be made by employing as an example, a case where "volume value" is used as a parameter.

Afterwards, the control unit 310 sequentially changes the threshold th until it reaches the maximum threshold th_max, and performs the procedures in steps S433 to S434 at each threshold th (step S435: No, S436). That is, the control unit 310 increments the threshold th sequentially from the minimum threshold th_min to the maximum threshold th_max, and performs (1) data-conversion, and (2) calculating and recording of the volume value of the continuous region, at each threshold th. As a result, the boundary of the continuous region CIM specified in step S434 at each threshold th is recorded in the predetermined storage unit. The incrementing rate for the threshold th (i.e. the lower limit of the target CT value range) is arbitrary, and thus arbitrarily set in accordance with the process capacity of the image processing apparatus 300 and a desired accuracy. In the present embodiment, it is assumed that the threshold th is incremented by "+1", for easier understanding.

Figure 37:
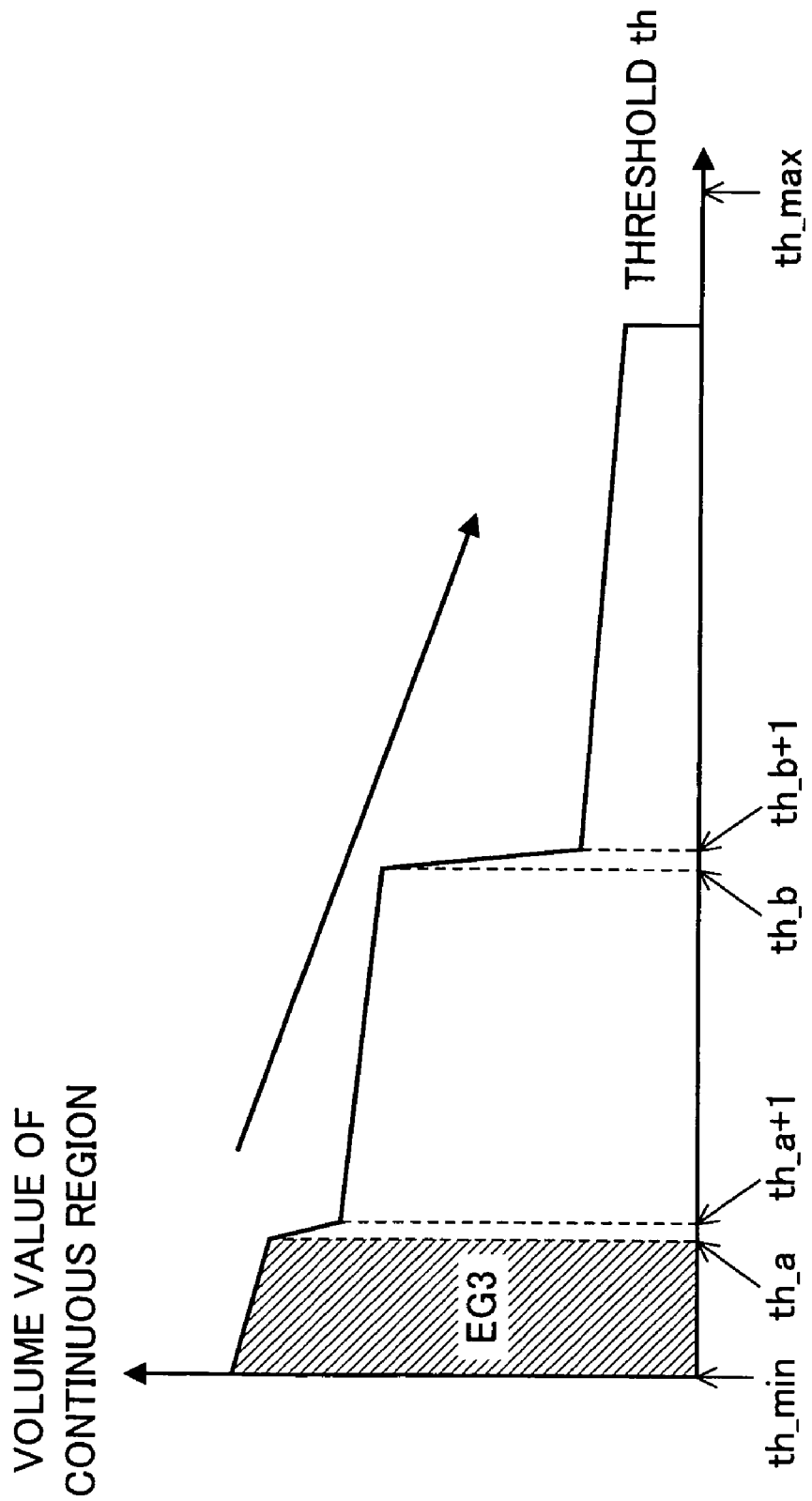
FIG. 37 is a graph showing changes in the volume of a continuous region in accordance with changes in threshold in the "vessel image clarifying process" shown in FIG. 36.

The control unit 310 calculates a volume value change rate in the range of minimum threshold th_min to maximum threshold th_max based on the volume values recorded for the respective thresholds th (step S437). That is, the control unit 310 can obtain a graph representing volume distribution as shown in FIG. 37 by plotting each volume value of the continuous region CIM of each threshold th. In this graph, the horizontal axis represents the threshold th (minimum threshold th_min to maximum threshold th_max), and the vertical axis represents the volume value of the continuous region CIM. As shown in FIG. 37, as the threshold th changes from the minimum threshold th_min to the maximum threshold th_max, the volume value of the continuous region CIM decreases. This is because the imaging target CT value range is narrowed in accordance with the change of the threshold th, and thereby the volume of the region to be imaged is reduced.

In the graph shown in FIG. 37, the thresholds at which there appear three or more contact points EG are excluded from the process target (the portion EG3 covered with slanted lines in FIG. 37). The target vessel is tubular and the center CP of the three-dimensional region TDR is on the target vessel Vt. Therefore, when the target vessel Vt is clarified (when an image representing the target vessel Vt and an image representing the heart HT are separated from each other), the continuous region CIM including the center CP represents only the target vessel Vt. Accordingly, the number of contact points EG at which the three-dimensional region TDR and the continuous region CIM contact can not be three or more.

During the process of incrementing the threshold th (i.e. the process of narrowing the target CT value range), there are some cases where the volume value of the continuous region CIM sharply drops, as shown by the graph of FIG. 37. According to this graph, the volume value sharply drops when the threshold th changes from th_a to th_a+1, and when the threshold th changes from th_b to th_b+1. The time when the threshold th changes "from th_a to th_a+1" is the time when the contact point EG3 at which the continuous region CIM and the three-dimensional region TDR have been contacting each other, disappears along with the reduction of the target CT value range. At this time, the volume value of the continuous region CIM sharply drops.

Figure 38A:
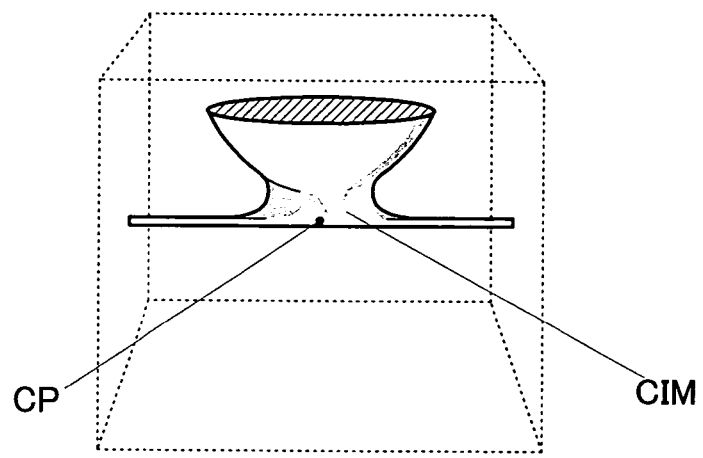
FIG. 38A shows an example of a continuous region when the number of a contact points at which the continuous region and a spatial region contact decreases.
Figure 38B:
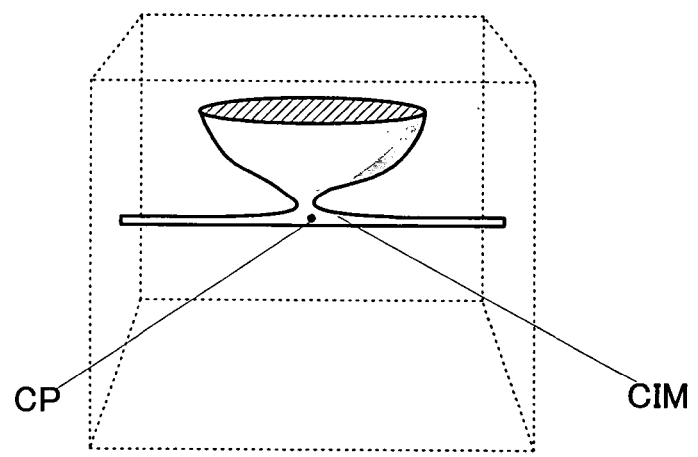
FIG. 38B shows an example of the continuous region when the volume of the continuous region is decreasing.

The time when the threshold changes "from th_b to th_b+1" is the time when the continuous region CIM is clarified to represent only the target vessel Vt. That is, in accordance with that the threshold th changes from th_a+1 to th_b, the volume value of the continuous region CIM decreases, as shown in FIG. 38B. Due to this, when the threshold th changed from th_b to th_b+1, the continuous region CIM is separated into a "continuous region CIM1" representing only the target vessel Vt and a "continuous region CIM2" representing a part of the heart HT. Here, the target of detection for boundary change is the continuous region that includes the center CP. Therefore, the continuous region CIM1 is the target of detection of boundary change. Accordingly, concerning the volume value of the continuous region CIM1, it sharply drops from the volume value at the threshold th_b at which the continuous region CIM1 is integrated with the continuous region CIM2.

This process is for detecting that the target vessel Vt is clarified in the image. Accordingly, it is possible to determine whether or not the target vessel Vt is clarified, by detecting a sharp decrease in the volume value (i.e. the boundary of the continuous region CIM). However, the change occurring when the contact point EG3 disappears may be larger than the change occurring when the target vessel Vt is clarified, depending on variation of conditions such as the location where the three-dimensional region TDR is specified, the shape of the continuous region, etc. Therefore, even if the threshold at which the volume value change rate is the largest is detected in the threshold range, the clarification of the vessel can not necessarily be detected. Hence, the control unit 310 excludes the thresholds at which the contact value EG3 remains. Then, the control unit 310 specifies the threshold at which the volume value change is the largest (that is, the change in the boundary of the continuous region CIM is the largest) among thresholds remaining after the exclusion (step S438).

The control unit 310 images picture elements (pixels, voxels) that are within the CT value range whose lower limit is the threshold specified in step S438 and whose upper limit is the threshold th_max (step S439). Then, the control unit 310 returns to the flow of the "unit vessel image generating process" shown in FIG. 33 to continue this process.

Figure 38C:
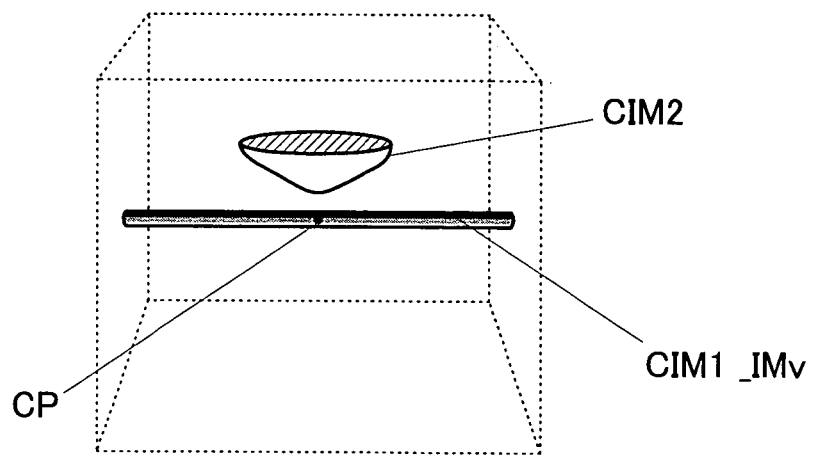
FIG. 38C shows an example of the continuous region when the continuous region is separated.

In the unit vessel image generating process, such a unit vessel image IMv as shown in FIG. 38C can be obtained by the data-conversion in step S439 (step S424).

Figure 30:
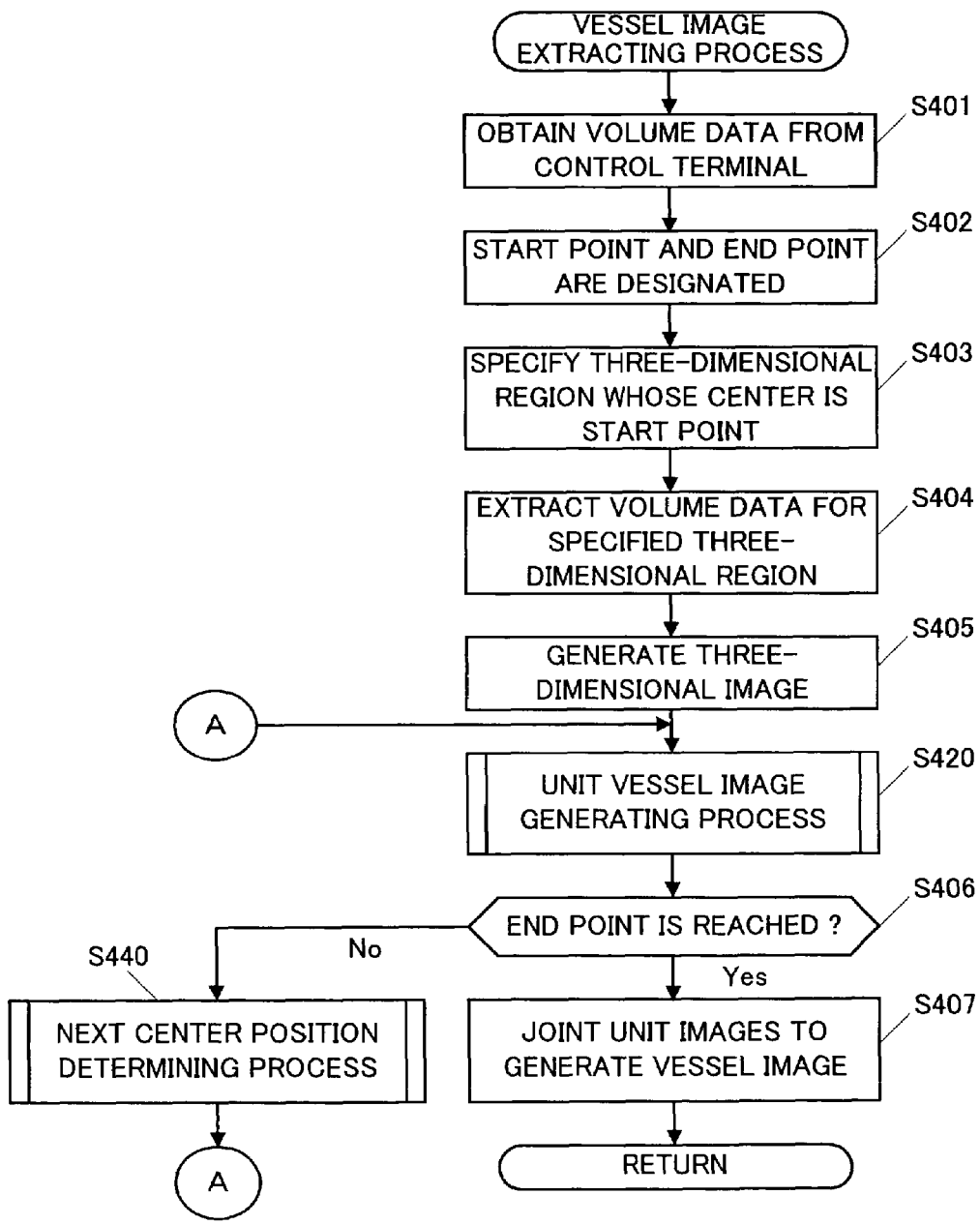
FIG. 30 is a flowchart for explaining a "vessel image extracting process" shown in FIG. 6.

When obtaining the unit vessel image IMv of the concerned three-dimensional region TDR, the control unit 310 stores the obtained image IMv in a predetermined storage area such as the work area, and returns to the flow of the "vessel image extracting process" shown in FIG. 30. In the present embodiment, the three-dimensional region TDR is specified for the start point SP to the end point EP sequentially along the target vessel Vt. Then, a three-dimensional image of the target vessel Vt is generated using the unit vessel images obtained from the respective three-dimensional regions TDR. Accordingly, when a unit vessel image is obtained in one three-dimensional region TDR, a "next center position determining process" (step S440) for specifying the next three-dimensional region TDR is performed until the end point EP is reached (step S406: No).

Figure 39A:
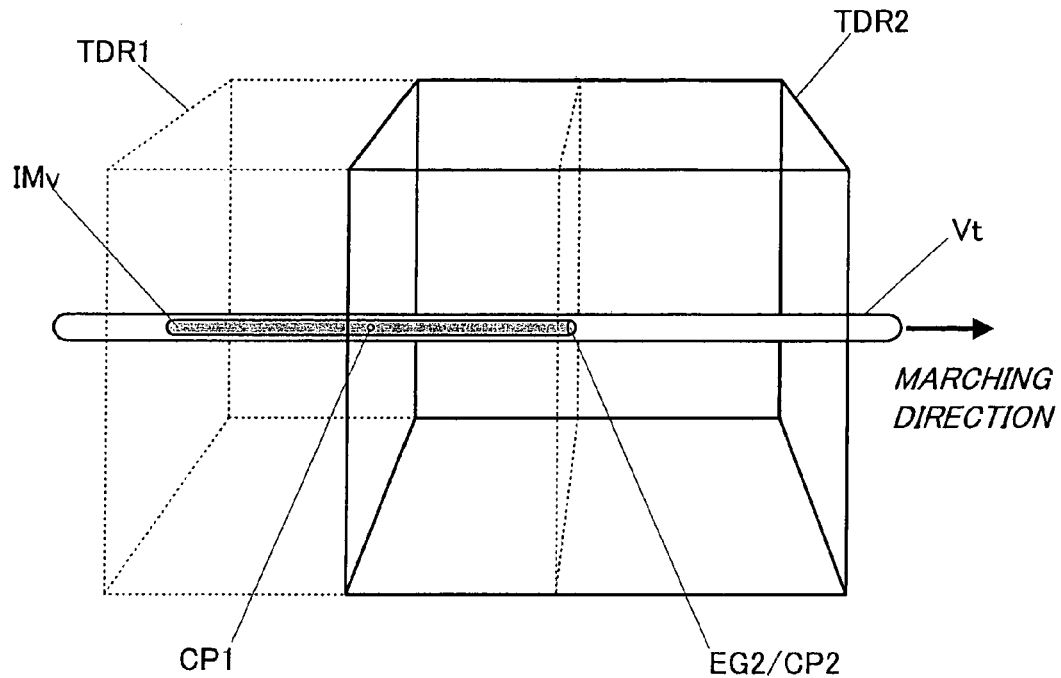
FIG. 39A is an exemplary diagram for explaining a case where an end of a unit vessel image is determined as the next center.

In the "next center position determining process", the position of the center CP of a three-dimensional region TDR to be specified next (hereinafter, this position will be referred to as "next center position") is determined. In this case, for example, the end position of the generated unit vessel image IMv can be determined as the next center position. More specifically, as shown in FIG. 39A, the next three-dimensional region TDR2 is specified by regarding as the center CP2, the end of the unit vessel image IMv generated in the three-dimensional region TDR1 (center CP1) which is specified before (i.e. the end is the contact point EG2 at which the unit vessel image IMv and the three-dimensional region TDR1 contact with each other).

Figure 39B:
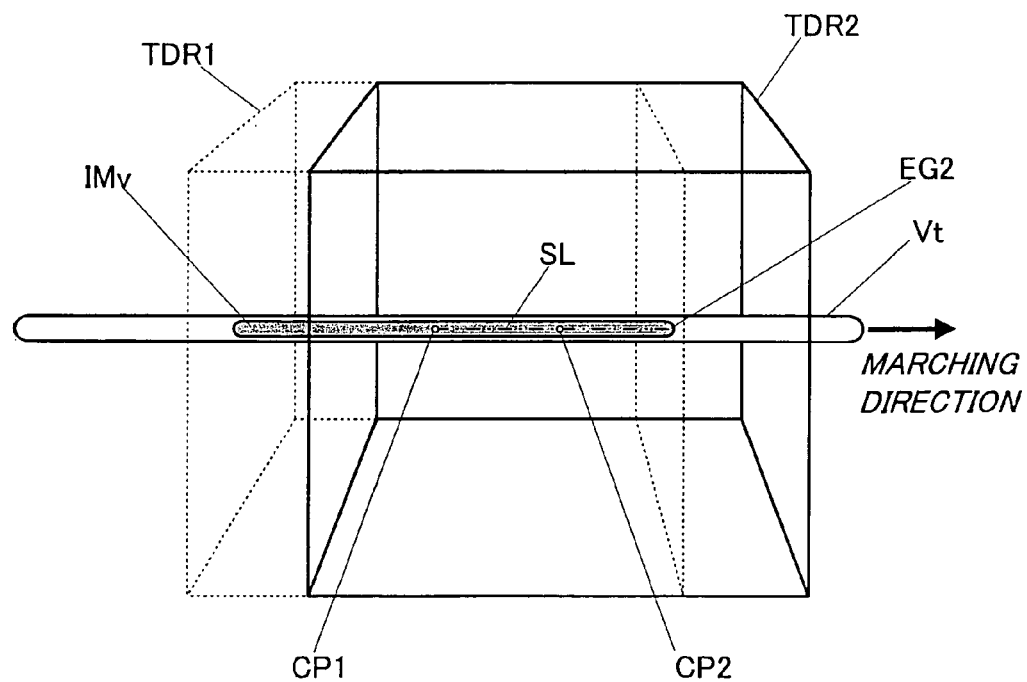
FIG. 39B is an exemplary diagram for explaining a case where a midpoint between an end of a unit vessel image and a former center is determined as the next center.

Or, as shown in FIG. 39B, a line segment PL (for example, three-dimensional path data) that connects the center CP1 of the formerly specified three-dimensional region TDR1 and the end of the unit vessel image IMv generated in the three-dimensional region TDR1 (i.e. the end is the contact point EG2 at which the unit vessel image IMv and the three-dimensional region TDR1 contact with each other) is obtained. Then, the middle point of this line segment PL is seen as the center CP2 for specifying the next three-dimensional region TDR2. Or, the continuous region may be subjected to Skeltonization, and a point on a line which is obtained by Skeltonization may be seen as the center for specifying the next spatial region.

In any of these manners, the three-dimensional region TDR is specified sequentially along the target vessel Vt (step S406 (No)→S440→S420: FIG. 30). When the end point EP is reached (step S406: Yes), the unit vessel images IMv in the respective three-dimensional regions TDR that are stored in the work area or the like are jointed. Thereby, a three-dimensional image representing the target vessel Vt from the start point SP to the end point EP is generated, and the "vessel image extracting process" is completed (step S407).

In the "image diagnosis process" (FIG. 6), the "medical image generating/outputting process" (step S500) for generating and outputting a predetermined medical image by using a vessel image generated in the above-described "vessel image extracting process" (FIG. 30) is performed. In this step, a medical image Mim shown in FIG. 28 representing a coronary vessel around a heart is generated and displayed in a predetermined window MW which is displayed on the output device 34 (display device).

As explained above, according to the image diagnosis system of the present embodiment, in generating a three-dimensional image of a tubular tissue such as a vessel, the vessel is clarified by changing the threshold in each three-dimensional region TDR. Therefore, even if, for example, CT values fluctuate in the middle of a vessel due to a change in the vessel diameter or presence of an abnormal portion, a three-dimensional image of the target vessel Vt can be accurately extracted. Accordingly, a good image having no discontinuation, etc. can be obtained. Further, in a case where other organs, etc. having similar CT values exist closely, the center line of the target vessel can be accurately extracted. Accordingly, medical image display which is very helpful for diagnosis and treatment for a coronary vessel around a heart can be realized.

The present invention is not limited to the above-described embodiment, but modifications and applications in various ways are available.

In the above-described embodiment, an operator operates the input device 33 and designates the start point SP and end point EP (arbitrary points) on a two-dimensional image representing a cross section of a vessel. However, a way of designating arbitrary points is not limited to this. For example, arbitrary points may be designated on various images generated in the above-described "medical image generating/outputting process" (i.e. three-dimensional image, CPR image, etc.). Or, arbitrary points may be designated not by the operation of the operator, but by an instruction, etc. from a program executed by the image processing apparatus 300 or from another apparatus connected to the image processing apparatus 300. Further, in the above-described embodiment, both of the start point SP and the end point EP are designated. However, either one of the start point SP and the end point EP may be designated. In this case, the "marching (advancing, progressing) direction (extracting direction)" may be designated by the operator or an instruction of a program, etc. In the above-described embodiment, extraction is terminated when the orthogonal cross sectional region SR at the end point EP is specified. However, the present invention is not limited to this, but for example, a threshold for a vessel diameter may be set, so that extraction is terminated when a vessel diameter which is equal to or smaller than a predetermined value is detected.

In the above-described embodiment, the threshold representing the lower limit of the "target CT value range" is changed. However, setting of the threshold may be arbitrary. For example, the threshold may represent the upper limit of the "target CT value range". In the above-described embodiment, the threshold is changed from the minimum threshold th_min to the maximum threshold th_max. However, the manner of changing the threshold may be arbitrary. For example, it may be changed from the maximum threshold th_max to the minimum threshold th_min. Further, in the above-described embodiment, the "target CT value range" is gradually narrowed by changing the threshold. However, the present invention is not limited to this pattern, but clarification may be detected by gradually expanding the "target CT value range".

In the above-described embodiment, a CT scanner is employed as the modality 100. Therefore, explanation has been made by employing a case where a CT image is used as an example. However, as described above, a modality 100 that can be employed is arbitrary. Accordingly, images corresponding to the modality to be employed (for example, MR image, ultrasonic image, etc.) may be used.

In the above-described embodiment, particularly, a vessel such as a coronary vessel is the target of extraction. However, any tubular tissue (tubular organ, luminal organ) may be the target of extraction. For example, the trachea, the intestines, etc. may be the target of extraction.

The image processing apparatus 300 in the above-described embodiment may be constituted by a dedicated apparatus, or may be constituted by a general-purpose computer apparatus such as a personal computer, etc. In the latter case, if some parts or all parts of a program for realizing the above-described processes are installed in a general-purpose computer apparatus, the image processing apparatus 300 can be realized by executing the installed program under the control of an OS, etc. The manner of distributing the program in this case is arbitrary. For example, the program can be distributed while being stored in a recording medium such as a CD-ROM or the like, or can be distributed via a communication medium (such as the Internet) if the program is embedded in a carrier wave.

The vessel image extracting process using the first process method has been explained by employing the orthogonal cross sectional region SR_ex2 shown in FIG. 15 (the case where another vessel Vs is close to the target vessel Vx) as an example. However, also in case of the orthogonal cross sectional region SR_ex1 shown in FIG. 15 (i.e., a case where the heart HT is close to the target vessel Vx), the cross section of the target vessel Vt can be accurately extracted. This is because the present invention is for changing the target CT value range in each specified orthogonal cross sectional region and detecting the center of the vessel when the cross section of the vessel is clarified as a result of changing the target CT value range. Due to this characteristic, similar CT values can be accurately distinguished from each other. Therefore, not only the illustrated orthogonal cross sectional regions SR_ex1 and _ex2, but also any region that includes the cross section of the target vessel Vt may be the target of extraction. For example, if other organs or tissues are close to the target vessel Vt, the center of the cross section of the target vessel Vt can be accurately detected.

Figure 40A:
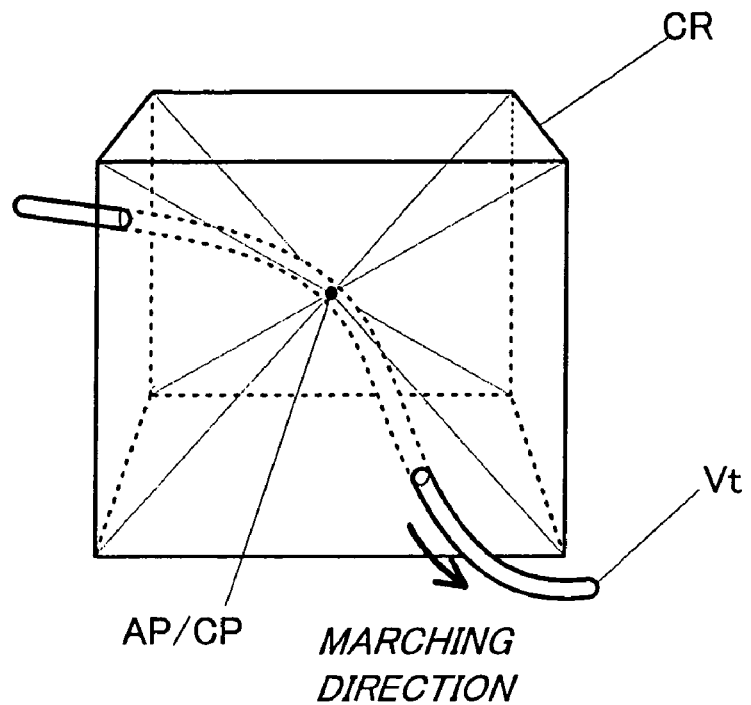
FIG. 40A shows an example of a positional relationship between an arbitrary point on a target vessel and a cubic region to be specified.

In this case, a manner of specifying the region that includes the cross section of the target vessel Vt is arbitrary. For example, the region including the cross section of the target vessel Vt may be specified by specifying a predetermined three-dimensional region (spatial region). In this case, as shown in FIG. 40A, an arbitrary point AP on the target vessel Vt (for example, the "start point SP", etc. designated in step S302 of the "vessel image extracting process" (FIG. 8)) is designated. Then, the three-dimensional coordinates of this arbitrary point AP are specified, and also a three-dimensional region having a cubic shape (hereinafter referred to as "cubic region CR") whose median point CP coincides with the arbitrary point AP is specified. Since the target vessel Vt has a tubular shape, it should contact the surfaces of the cubic region CR at two points (of these, one contact point in the upstream of the marching (advancing, progressing) direction will hereinafter be referred to as "contact point EG1", and the other in the downstream "contact point EG2"). Of the surfaces constituting the cubic region CR, the surface that includes the contact point EG1 is referred to as "cross sectional region SRa" and the surface that includes the contact point EG2 is referred to as "cross sectional region SRb". Then, extraction of the cross section of the vessel in these cross sectional regions and specification of the center of the cross section are performed. That is, by performing the "vessel center detecting process" (FIG. 17) for the cross sectional regions SRa and SRb, the three-dimensional coordinates representing the center of the cross section of the target vessel Vt at the contact point EG1 and contact point EG2 can be specified.

Figure 40B:
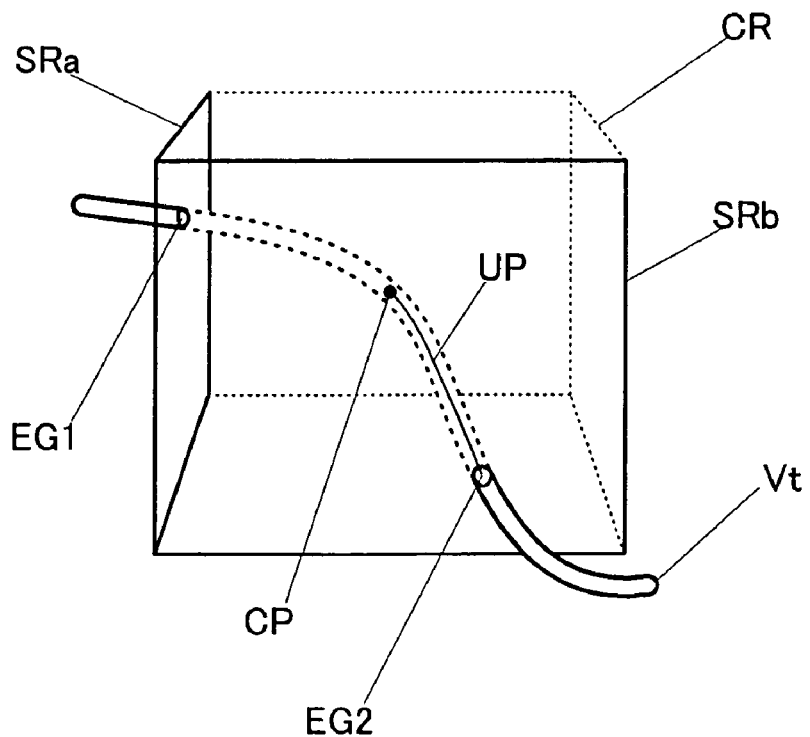
FIG. 40B shows an example of a cross sectional region in the specified cubic region and an example of an obtained unit path.

As a result, the three-dimensional coordinates of the median point CP and the contact points EG1 and EG2 are specified. Accordingly, such unit three-dimensional path data (hereinafter referred to as "unit path UP") as shown in FIG. 40B that connects the median point CP to the contact point EG2 in the cubic region CR can be obtained. That is, three-dimensional path data of the target vessel Vt, which is included in the cubic region CR can be obtained. The unit path UP may be one that connects two points, namely the contact point EG1 and the contact point EG2, or three points, namely the contact point EG1, the median point CP, and the contact point EG2.

Figure 41A:
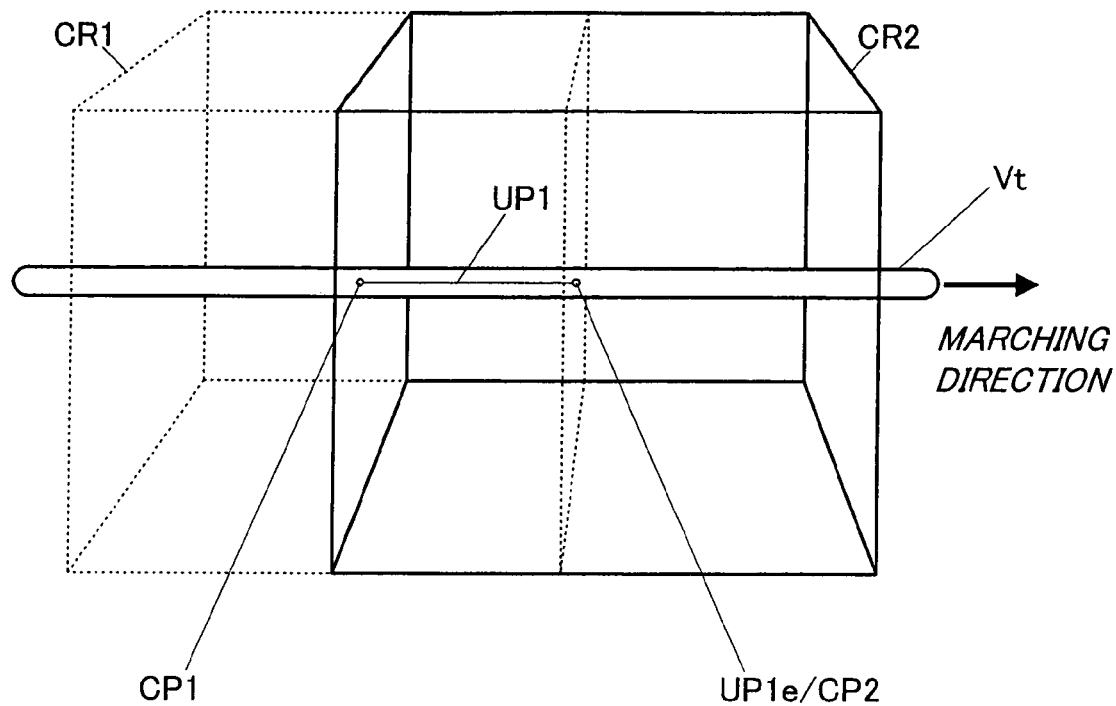
FIG. 41 are diagrams for explaining a method of sequentially specifying a cubic region shown in FIG. 40, where FIG. 41A exemplarily shows an example where an end of a unit path is the median point of the next cubic region, and FIG. 41B exemplarily shows an example where a midpoint of unit path is the median point of the next cubic region.
Figure 41B:
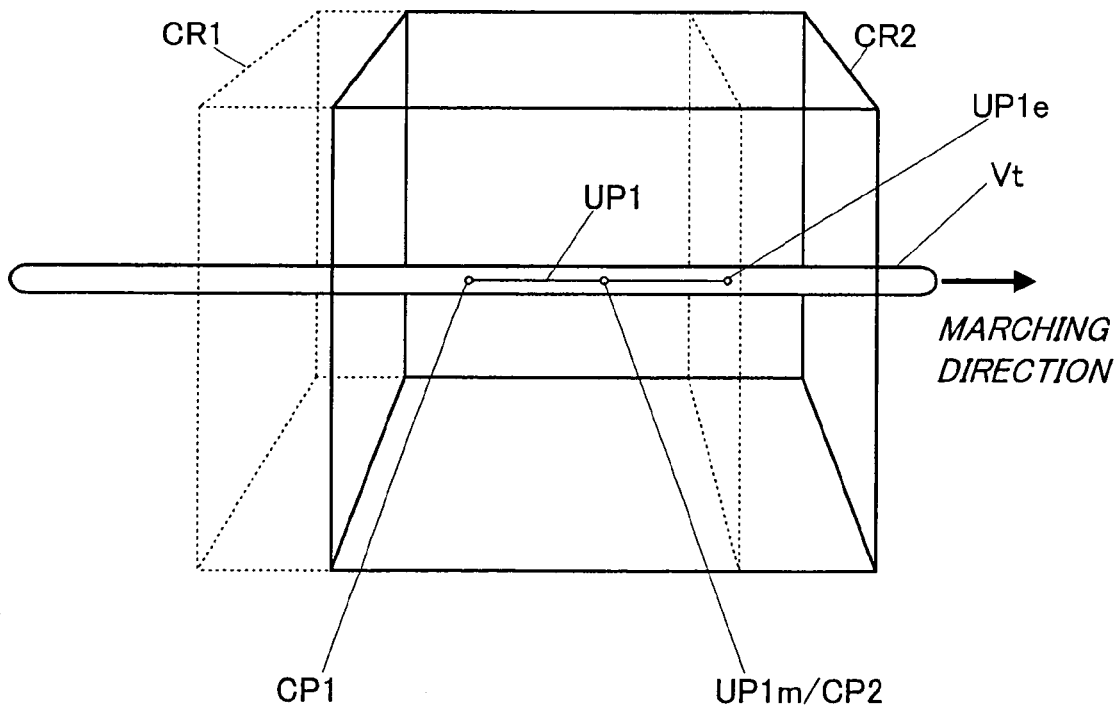

Using the "unit path UP" obtained in this manner, the following three-dimensional region can be specified. For example, as shown in FIG. 41A, by regarding an end UP1e of the unit path UP1 in the formerly specified cubic region CR1 as a median point CP2, the next cubic region CR2 may be specified. Or, as shown in FIG. 41B, by regarding a midpoint UP1m between the median point CP1 of the formerly specified cubic region CR1 and the end UP1e of the unit path UP1 as a median point CP2, the next cubic region CR2 may be specified. By sequentially specifying cubic regions CR in this manner, a plurality of unit paths UP can be obtained. Thus, a path P_Vt representing the center line of the vessel from the start point SP to the end point EP can be obtained based on the plurality of unit paths UP.

Figure 42A:
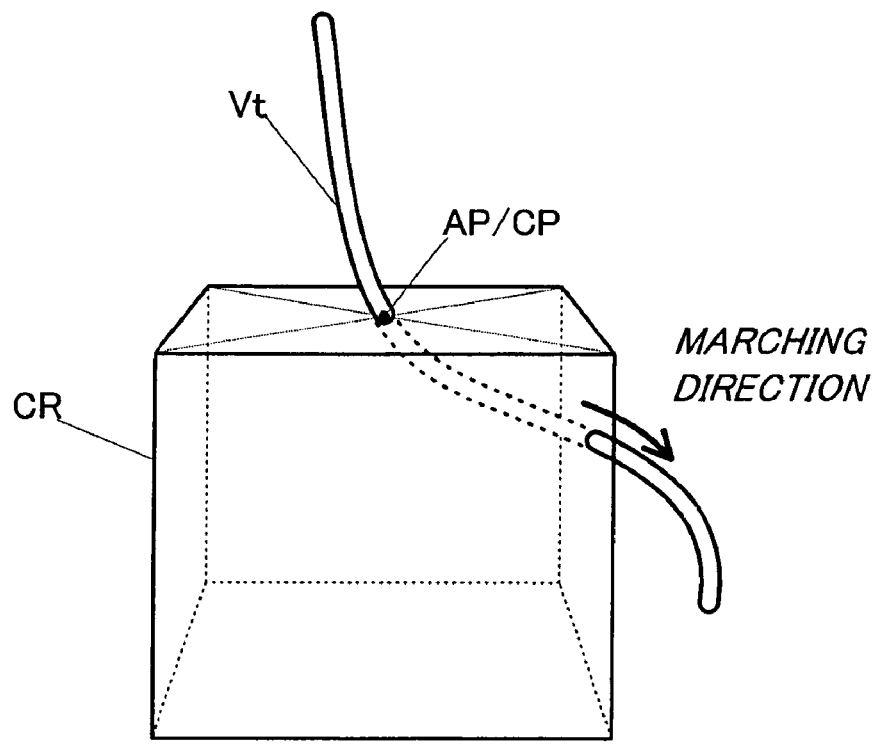
FIG. 42A shows an example of a positional relationship between an arbitrary point n a target vessel and a cubic region to be specified.
Figure 42B:
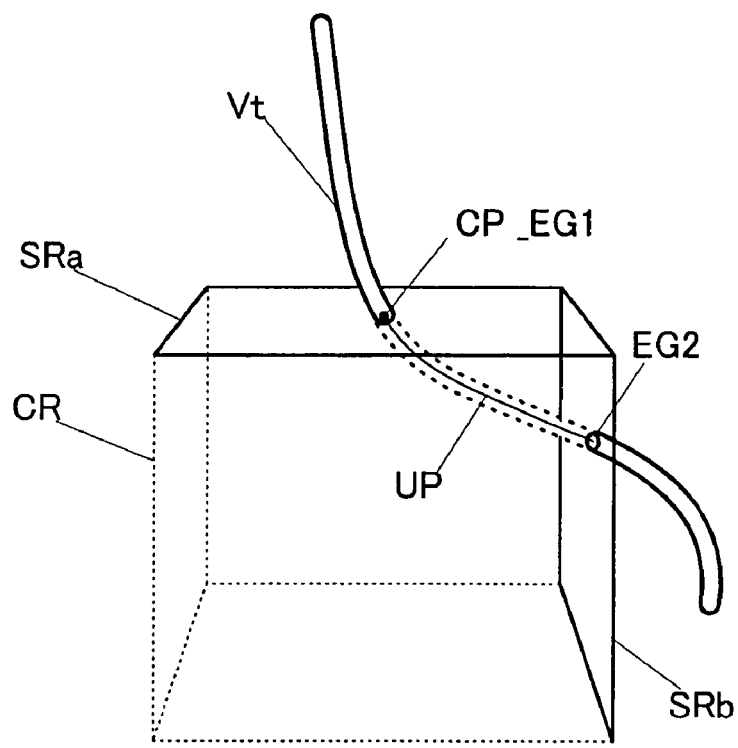
FIG. 42B shows an example of a cross sectional region in the specified cubic region and an example of an obtained unit path.

The arbitrary point AP may not be the median point of the cubic region CR, but may be, for example, the center of one surface of the cubic region CR (hereinafter the center will be referred to as "center CP") as shown in FIG. 42A, and the cubic region CR may be specified based on this center CP. In this case, among the surfaces constituting the cubic region CR, the surfaces that are contacted by the target vessel Vt may be regarded as a cross sectional regions SRa and SRb as shown in FIG. 42B, and the cross section of the vessel and the center of the cross section can be specified. Since the contact point EG1 in this case coincides with the arbitrary point AP (center CP), "extraction of the cross section of the vessel" and "specification of the center of the cross section" may be performed for the contact point EG2. As a result, a three-dimensional path that connects the center CP and the contact point EG2 can be obtained as a "unit path UP".

Figure 43A:
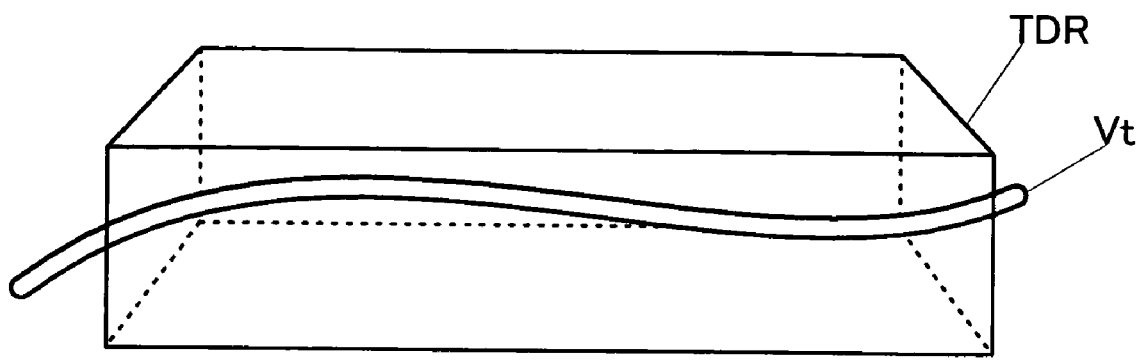
FIG. 43A shows a spatial region having a rectangular parallelepiped shape.
Figure 43B:
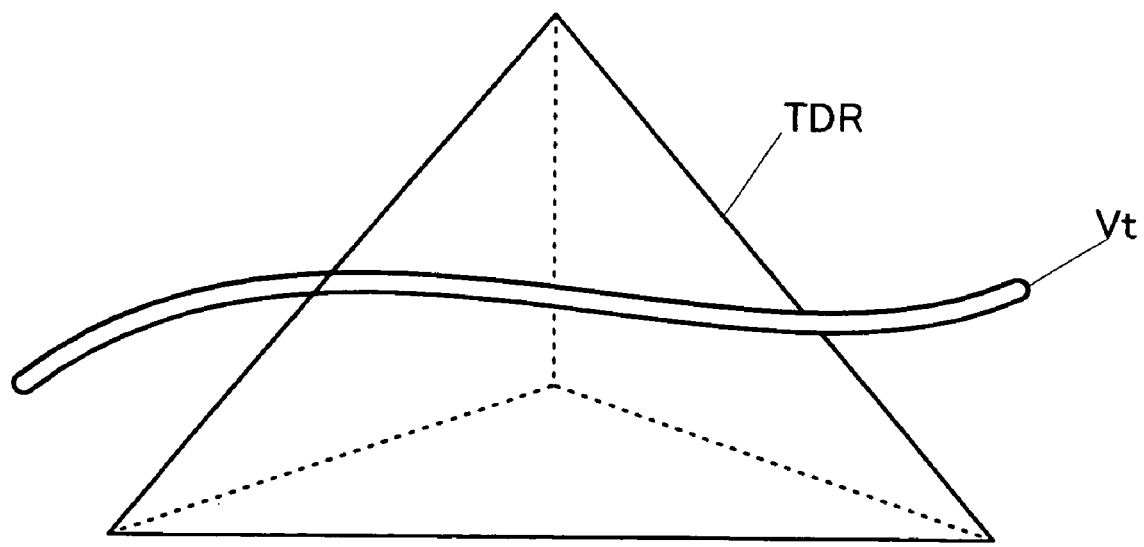
FIG. 43B shows a spatial region having a triangular pyramid shape.
Figure 44A:
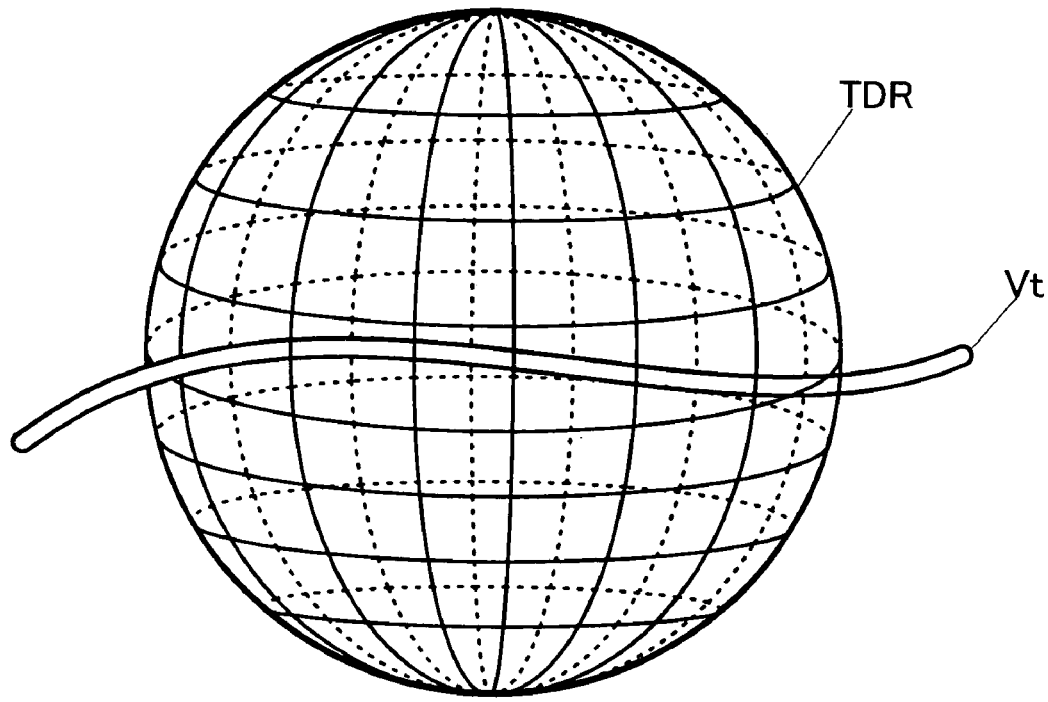
FIG. 44A shows a spatial region having a sphere shape.
Figure 44B:
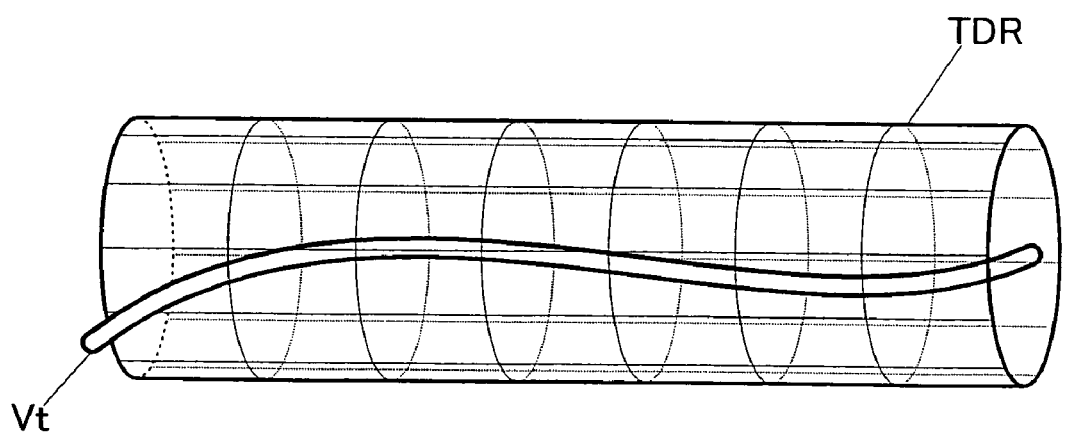
FIG. 44B shows a spatial region having a circular cylinder shape.

The shape of the three-dimensional region (spatial region) to be specified is not limited to a cube as described above, but may be an arbitrary shape. For example, a rectangular parallelepiped shown in FIG. 43A, a triangular pyramid shown in FIG. 43B, a sphere shown in FIG. 44A, a circular cylinder shown in FIG. 44B, etc. may be used. Other than these, an oval sphere, a barrel shape, a torous shape (tubular ring surface) may be used.

Further, specification of such a "three-dimensional region" and specification of the "orthogonal cross sectional region" illustrated in the above-described embodiment may be combined. For example, the "orthogonal cross sectional region" may be used at the start point SP and the end point EP, and the "three-dimensional region" may be used between the start point SP and end point EP exclusive of these points.

In the "cross section clarifying process" employing the first process method, the threshold at which area change is the largest in the threshold range from which NG values are excluded in advance is detected. However, the method of detecting the threshold at which the cross section of a vessel is clarified is not limited to this. For example, in a case where major area change occurs more than once, the circularlity of the center unit image obtained at each time is obtained. The threshold at which the center unit image having the highest circularlity is obtained may be specified as the "threshold at which the cross section of the vessel is clarified".

At this time, clarification of the cross section of the vessel is detected by observing changes in the area. However the target of observation is not limited to area change, but may be changes in circularlity, median point, length of circumference, etc.

In the "marching (advancing, progressing) direction settling process" employing the first process method, the marching (advancing, progressing) direction is settled by specifying two parallel cross sectional regions for each orthogonal cross sectional region. However, the method of settling the marching (advancing, progressing) direction is not limited to this. Any method can be used if it can appropriately settle the direction to march. Even if the method explained in the above-described embodiment is employed, the number of the parallel cross sectional regions to specify is not limited to "2", but is arbitrary. That is, the marching (advancing, progressing) direction may be corrected or settled based on a longitudinal direction image in only one parallel cross sectional region. Or, the marching (advancing, progressing) direction may be corrected or settled based on longitudinal direction images in three or more parallel cross sectional regions. Even for obtaining such a longitudinal direction image, the target clarifying method used in the above-described "cross section clarifying process" may be used. In a case where another tissue is close to the target vessel Vt, this tissue is included also in a parallel cross sectional region. By clarifying a longitudinal direction cross section in the same way as the above-described clarification of a cross section of a vessel, the center position of the longitudinal direction cross section can be accurately detected.

In the "medical image generating/outputting process" employing the first process method, a case wherein a three-dimensional image, a two-dimensional path, a CPR image, a graph, an MPR image are displayed on the same screen has been explained. However, the types of images to generate and output, the number of images to display at a time, etc. are arbitrary. The image processing apparatus 300 according to the above-described embodiment may have only a function for, for example, obtaining a center line path of a tubular tissue. In this case, the image processing apparatus 300 may provide obtained tree-dimensional path data to another image generating apparatus, so that various images are generated by this image generating apparatus. Further, for example, the modality 100 or the control terminal 200 may have some or all of the functions possessed by the image processing apparatus 300 for performing the above-described processes in the above-described embodiment. That is, each function of the image processing apparatus 300 may be realized by a single apparatus, or may be realized by a plurality of apparatuses working together.

In the process employing the second process method, a case where a three-dimensional region having a cubic shape is specified as the three-dimensional region TDR has been illustrated. However, likewise the case of the first process method, the shape of the three-dimensional region TDR is not limited to this. For example, a rectangular parallelepiped shown in FIG. 43A, a triangular pyramid shown in FIG. 43B, a sphere shown in FIG. 44A, and a circular cylinder shown in FIG. 44B may be used. Other than these, an arbitrary shape, for example, an oval sphere, a barrel shape, and a torous shape (tubular ring surface) may be specified the three-dimensional region TDR. In the above-described embodiment, it is determined whether a continuous region represents only the target vessel or not, by determining whether the number of contact points at which the three-dimensional region and the continuous region contact with each other is equal to or greater than three. However, the number of contact points used for determination is not limited to three but is arbitrary, as long as clarification of the target vessel can be detected by such an arbitrary number.

In the process employing the second process method, a three-dimensional region whose center is an arbitrary point on the target vessel Vt is specified. However, the manner of specifying a three-dimensional region is not limited to this, as long as an alternative manner can extract the target vessel Vt. For example, a three-dimensional region may be specified so that an arbitrary point on the target vessel Vt coincides with a predetermined vertex of the three-dimensional region to be specified. Or, a three-dimensional region may be specified so that an arbitrary point on the target vessel Vt coincides with the center of one surface constituting the three-dimensional region to be specified.

In the process employing the second process method, a case where clarification of an image of a vessel is detected by observing changes in the volume of the continuous region CIM has been illustrated. However, what is observed is not limited to the volume. For example, detection may be performed based on, for example, changes in the shape of the continuous region CIM. Further, in the above-described embodiment, a closed continuous region such as a "limited closed image" is used for detecting a clarified image of a vessel. However, an open region having some continuity may be used as long as clarification can be detected, that is, the boundary of an image representing only the target vessel Vt can be identified.

Furthermore, an arbitrary "threshold" can be used. For example, in a case where "Region Growing" method is used for generating a three-dimensional image, a region may be changed by changing a parameter (for example, "threshold for gradient"). In this case, there may exist a plurality of parameters.

Various embodiments and changes may be made thereunto without departing from the broad spirit and scope of the invention. The above-described embodiment is intended to illustrate the present invention, not to limit the scope of the present invention. The scope of the present invention is shown by the attached claims rather than the embodiment. Various modifications made within the meaning of an equivalent of the claims of the invention and within the claims are to be regarded to be in the scope of the present invention.

What is claimed is:

1. A medical image processing apparatus for generating a medical image of a target vessel by using three-dimensional volume data representing a portion in a living body, said apparatus comprising:
   a volume data obtaining unit which obtains predetermined three-dimensional volume data including a tubular tissue of the target vessel;
   a region specifying unit which specifies a region including a position on the tubular tissue in the three-dimensional volume data at each of a plurality of such positions as said region specifying unit specifies a planar region which orthogonally intersects with the longitudinal direction of the tubular tissue, said region specifying unit establishing an orthogonal cross sectional region orthogonal to the longitudinal direction of the target vessel by marching along the target vessel in a marching direction;
   an extraction unit which extracts information on the tubular tissue in each of the specified regions;
   a parallel region specifying unit which specifies a first parallel region and a second parallel region along the target vessel at each of said positions wherein the parallel regions are perpendicular with each other and perpendicular with the orthogonal cross sectional region at each position;
   a parallel region extraction unit which extracts information on the tubular tissue in each of the specified parallel regions;
   a marching direction determination unit for determining the marching direction based on the information on the tubular tissue extracted from each of the specified parallel regions;
   a center specifying unit of said extraction unit for specifying a center position of a cross section of the tubular tissue in each of the plurality of regions specified by said region specifying unit; and
   a medical image generating unit which generates a medical image representing the tubular tissue, based on the information extracted by said extraction unit.

2. The medical image processing apparatus according to claim 1, wherein:
   each of the plurality of regions are specified by said region specifying unit based on the three-dimensional volume data obtained by the volume data obtaining unit; and
   a center line specifying unit which specifies a center line of the tubular tissue in a longitudinal direction of the tubular tissue, based on the plurality of center positions specified by said center specifying unit.

3. The medical image processing apparatus according to claim 2, wherein:
   said region specifying unit sequentially specifies regions along the tubular tissue; and
   said center specifying unit specifies a center of a cross section of the tubular tissue in each of the regions sequentially specified by said region specifying unit.

4. The medical image processing apparatus according to claim 2, wherein:
   said center specifying unit specifies a center position of a cross section of the tubular tissue in the planar region specified by said region specifying unit.

5. The medical image processing apparatus according to claim 2, wherein said extraction unit includes:
   a unit which obtains a median point represented by the three-dimensional volume data, of the tubular tissue in each of the plurality of regions specified by said region specifying unit;
   a cross sectional image generation unit which generates a cross sectional image representing a cross section of the tubular tissue at a position of the median point obtained by said unit for obtaining a median point; and
   a center specifying unit which specifies a center position of the cross section in the three-dimensional volume data, based on the generated cross sectional image.

6. The medical image processing apparatus according to claim 2, further comprising a designation reception unit which receives designation for two arbitrary points on the tubular tissue represented by the three-dimensional volume data, wherein:
   said region specifying unit sequentially specifies planar regions which orthogonally intersect with the longitudinal direction of the tubular tissue, at a plurality of positions between the two points along the tubular tissue; and
   said center specifying unit specifies a center of a cross section of the tubular tissue in each of the plurality of planar regions specified by said region specifying unit.

7. The medical image processing apparatus according to claim 6, wherein:
   said designation reception unit receives designation for a planar region which orthogonally intersects with the longitudinal direction of the tubular tissue, at one of the two designated points;
   said region specifying unit sequentially specifies points which are apart from one another by a predetermined distance in a direction heading from the one point to the other point of the two points along the tubular tissue, and sequentially specifies planar regions orthogonally intersecting with the longitudinal direction of the tubular tissue at each of the specified points;

said center specifying unit specifies a center position of a cross section of the tubular tissue in each of the plurality of planar regions specified by said region specifying unit; and said center line specifying unit specifies a center line of the tubular tissue in the longitudinal direction of the tubular tissue, based on the plurality of center positions specified by said center specifying unit.

8. The medical image processing apparatus according to claim 5, wherein:

the three-dimensional volume data includes three-dimensional coordinate information and characteristic information representing a characteristic unique to a substance at each position represented by the three-dimensional coordinate information; and said cross sectional image generation unit generates an image based on information representing a three-dimensional coordinate position having the characteristic information which satisfies a predetermined condition in the three-dimensional volume data, and clarifies the cross section of the tubular tissue in the image.

9. The medical image processing apparatus according to claim 8, wherein said imaging unit comprises:

a condition changing unit which changes the predetermined condition;

an image attribute detecting unit which detects an image attribute which changes in accordance with changes in the predetermined condition; and a clarification determining unit which determines whether or not the cross section of the tubular tissue is clarified in an image, based on detected changes in the image attribute.

10. The medical image processing apparatus according to claim 9, wherein:

the image attribute represents an area of an image;

said image attribute detecting unit detects an image area which changes in accordance with changes in the predetermined condition, and detects a change in the image area corresponding to the changes in the predetermined condition; and said clarification determining unit determines whether or not the cross section of the tubular tissue is clarified, based on the detected change in the image area.

11. The medical image processing apparatus according to claim 10, wherein said clarification determining unit determines that the cross section of the tubular tissue is clarified in the image, when an image appearing in a center of the region including the cross section become fit inside the region, and the change in the image area becomes the largest.

12. The medical image processing apparatus according to claim 5, wherein said region specifying unit determines a position of a three-dimensional region to be specified next, based on the three-dimensional volume data which is specified by said center line specifying unit and which represents the center line of the tubular tissue.

13. The medical image processing apparatus according to claim 5, wherein:

said center line specifying unit specifies the center line of the tubular tissue as three-dimensional path data; and said medical image processing apparatus further comprises an image generating unit which generates an image representing the tubular tissue based on the three-dimensional path data specified by said center line specifying unit.

14. The medical image processing apparatus according to claim 13, wherein said image generating unit comprises:

an image calculating unit which generates plural kinds of images each representing the tubular tissue, and calculates relative positional relationships between the images; and a display control unit which displays the generated plural kinds of images all at once on a predetermined display device, and displays positional relationships on the displayed images by associating the relations based on the relative positional relationships between the images calculated by said image calculating unit.

15. The medical image processing apparatus according to claim 1, wherein:

said region specifying unit specifies a predetermined three-dimensional region whose center is an arbitrary point on the predetermined tubular tissue represented by the three-dimensional volume data;

said region specifying unit also specifies a continuous region at least partially defined within the predetermined three-dimensional region and including the coordinates of the arbitrary point and detects a number of positions at which the continuous region and a surface of the three-dimensional region contact each other;

said medical image processing apparatus further comprises an image clarifying unit which, when the number of positions of contact exceeds a predetermined value, clarifies a three-dimensional image representing only the predetermined tubular tissue in the specified three-dimensional region, by changing predetermined characteristic information included in the three-dimensional volume data which constitutes a three-dimensional image obtained by data-conversion of said imaging unit; and said medical image generating unit generates a predetermined medical image representing the predetermined tubular tissue, by using the three-dimensional image clarified by said image clarifying unit.

16. The medical image processing apparatus according to claim 15, wherein:

said image clarifying unit comprises a closed region detecting unit which detects a closed region which constitutes the three-dimensional image obtained by data-conversion of said imaging unit and which includes a center of the three-dimensional region, and a clarification determining unit which determines based on the closed region detected by said closed region detecting unit and the three-dimensional region whether or not the closed region represents only the predetermined tubular tissue; and the closed region which is determined by said clarification determining unit as representing only the predetermined tubular tissue is regarded as the clarified three-dimensional image.

17. The medical image processing apparatus according to claim 16, wherein:

said closed region detecting unit detects a change in the closed region corresponding to changes in the characteristic information; and said clarification determining unit determines whether or not the closed region represents only the predetermined tubular tissue, based on changes in the closed region.

18. The medical image processing apparatus according to claim 15, wherein:
said region specifying unit specifies a plurality of three-dimensional regions by setting a center of a three-dimensional region to be specified next based on the arbitrary point and/or the clarified three-dimensional image; and
said medical image generating unit generates the predetermined medical image representing the predetermined tubular tissue, by using three-dimensional images clarified in the plurality of three-dimensional regions.

19. A medical image processing method for generating an image representing a tubular tissue of a target vessel in a living body by using a computer, said method comprising:
a step of obtaining predetermined three-dimensional volume data including a tubular tissue of the target vessel;
a step of specifying a region including a position on the tubular tissue of the target vessel in the three-dimensional volume data at a plurality of such positions as a planar region which orthogonally intersects with the longitudinal direction of the tubular tissue by marching along the target vessel in a marching direction, said step of specifying a region further including establishing a region threshold and excluding areas beyond said threshold from said planar region thereby distinguishing adjacent vessels from said target vessel;
a step of specifying a first parallel region and a second parallel region along the target vessel at each of said positions wherein the parallel regions are perpendicular with each other and perpendicular with the planar region at each position;
a step of extracting information on the tubular tissue in each of the plurality of specified orthogonal regions and in each of the specified parallel regions;
a step of determining the marching direction along said target vessel based on the information on the tubular tissue extracted from each of the specified parallel regions;
a step of specifying a center position of a cross section of the tubular tissue in each of the plurality of regions specified by a region specifying unit; and
a step of generating a medical image representing the tubular tissue, based on the extracted information.

20. The medical image processing method according to claim 19, wherein said step of extracting information on the tubular tissue includes:
a step of specifying a center position of a cross section of the tubular tissue in each of the plurality of specified regions; and
a step of specifying a center line of the tubular tissue in a longitudinal direction of the tubular tissue, based on the plurality of specified center positions.

21. The medical image processing method according to claim 20, wherein:
in said step of specifying a region, the regions are sequentially specified along the tubular tissue; and
in said step of specifying a center position, a center position of a cross section of the tubular tissue in each of the regions sequentially specified is specified.

22. The medical image processing method according to claim 20, wherein:
in said step of specifying a region, a planar region which orthogonally intersects with the longitudinal direction of the tubular tissue is specified; and
in said step of specifying a center position, a center position of a cross section of the tubular tissue in the specified planar region is specified.

23. The medical image processing method according to claim 20, wherein said step of extracting information includes:
a step of obtaining a median point of the tubular tissue represented by the three-dimensional volume data in each of the plurality of specified regions;
a step of generating a cross sectional image representing a cross section of the tubular tissue at a position of the median point obtained in said step of obtaining a median point; and
a step of specifying a center position of the cross section in the three-dimensional volume data, based on the generated cross sectional image.

24. The medical image processing method according to claim 20, further comprising a step of receiving designation for two arbitrary points on the tubular tissue represented by the three-dimensional volume data,
wherein:
in said step of specifying a region, planar regions orthogonally intersecting with the longitudinal direction of the tubular tissue are sequentially specified at a plurality of positions between the two points along the tubular tissue; and
in said step of specifying a center position, a center position of a cross section of the tubular tissue in each of the plurality of specified planar regions is specified.

25. The medical image processing method according to claim 24, wherein:
in said step of receiving designation, designation for a planar region orthogonally intersecting with the longitudinal direction of the tubular tissue at one of the two designated points is received;
in said step of specifying a region, points apart from one another by a predetermined distance are sequentially specified along the tubular tissue in a direction heading from the one point to the other point of the two points, and planar regions orthogonally intersecting with the longitudinal direction of the tubular tissue at the specified points are sequentially specified;
in said step of specifying a center position, a center position of a cross section of the tubular tissue in each of the specified planar regions is specified; and
in said step of specifying a center line, a center line of the tubular tissue in the longitudinal direction of the tubular tissue is specified based on the specified center positions.

26. The medical image processing method according to claim 23, wherein:
the three-dimensional volume data includes three-dimensional coordinate information and characteristic information representing a characteristic unique to a substance at each position represented by the three-dimensional coordinate information; and
in said step of generating a cross sectional image, an image is generated based on information representing a three-dimensional coordinate position having the characteristic information satisfying a predetermined condition in the three-dimensional volume data, and the cross section of the tubular tissue is clarified in the image.

27. The medical image processing method according to claim 26, wherein said step of generating a cross sectional image includes:
a step of changing the predetermined condition;
a step of detecting an image attribute which changes in accordance with changes in the predetermined condition; and a step of determining whether or not the cross section of the tubular tissue is clarified in an image, based on detected changes in the image attribute.

28. The medical image processing method according to claim 27, wherein:

the image attribute represents an area of an image (image area);

in said step of detecting an image area which changes in accordance with changes in the predetermined condition, and detects a change in the image area corresponding to the changes in the predetermined condition; and in said step of determining whether or not the cross section of the tubular tissue is clarified, based on the detected change in the image area.

29. The medical image processing method according to claim 28, wherein said step of determining that the cross section of the tubular tissue is clarified in the image, when an image appearing in a center of the region including the cross section become fit inside the region, and the change in the image area becomes the largest.

30. The medical image processing method according to claim 23, wherein said step of determining a position of a three-dimensional region to be specified next, based on the three-dimensional volume data which is specified in said step of specifying the center line of the tubular tissue.

31. The medical image processing method according to claim 23, wherein:

said step of specifying the center line of the tubular tissue as three-dimensional path data; and said step of generating an image representing the tubular tissue based on the three-dimensional path data specified in said step of specifying the center line of the tubular tissue.

32. The medical image processing method according to claim 31, wherein said step of generating an image comprises:

a step of generating plural kinds of images each representing the tubular tissue, and calculates relative positional relationships between the images; and a step of displaying the generated plural kinds of images all at once on a predetermined display device, and displays positional relationships on the displayed images by associating the relations based on the relative positional relationships between the images calculated in said step of generating plural kinds of images.

33. The medical image processing method according to claim 19, wherein:

said step of specifying a predetermined three-dimensional region whose center is an arbitrary point on the predetermined tubular tissue represented by the three-dimensional volume data;

said step of clarifying a three-dimensional image representing only the predetermined tubular tissue in the specified three-dimensional region, by changing predetermined characteristic information included in the three-dimensional volume data which constitutes a three-dimensional image obtained by data-conversion; and said step of generating a predetermined medical image representing the predetermined tubular tissue, by using the three-dimensional image clarified in said step of clarifying an image.

34. The medical image processing method according to claim 33, wherein:

said step of clarifying an image a step of detecting a closed region which constitutes the three-dimensional image obtained by data-conversion and which includes a center of the three-dimensional region, and a step of determining based on the detected closed region and the three-dimensional region whether or not the closed region represents only the predetermined tubular tissue; and the closed region which is determined as representing only the predetermined tubular tissue is regarded as the clarified three-dimensional image.

35. The medical image processing method according to claim 34, wherein:

said step of detecting a change in the closed region corresponding to changes in the characteristic information; and said step of determining whether or not the closed region represents only the predetermined tubular tissue, based on changes in the closed region.

36. The medical image processing method according to claim 33, wherein:

said step of specifying a plurality of three-dimensional regions by setting a center of a three-dimensional region to be specified next based on the arbitrary point and/or the clarified three-dimensional image; and said step of generating the predetermined medical image representing the predetermined tubular tissue, by using three-dimensional images clarified in the plurality of three-dimensional regions.

* * * * *

UNITED STATES PATENT AND TRADEMARK OFFICE
CERTIFICATE OF CORRECTION

PATENT NO. : 7,639,855 B2
APPLICATION NO. : 10/816978
DATED : December 29, 2009
INVENTOR(S) : Kazuhiko Matsumoto Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1224 days.

Signed and Sealed this

Ninth Day of November, 2010

David J. Kappos
*Director of the United States Patent and Trademark Office*